United States Patent
Covey

(10) Patent No.: US 10,202,413 B2
(45) Date of Patent: Feb. 12, 2019

(54) NEUROACTIVE ENANTIOMERIC 15-, 16- AND 17-SUBSTITUTED STEROIDS AS MODULATORS FOR GABA TYPE-A RECEPTORS

(71) Applicant: Washington University, St. Louis, MO (US)

(72) Inventor: Douglas Covey, St. Louis, MO (US)

(73) Assignee: Washington University, St. Louis, MO (US)

( * ) Notice: Subject to any disclaimer, the term of this patent is extended or adjusted under 35 U.S.C. 154(b) by 101 days.

(21) Appl. No.: 14/767,235

(22) PCT Filed: Feb. 14, 2014

(86) PCT No.: PCT/US2014/016405
§ 371 (c)(1),
(2) Date: Aug. 11, 2015

(87) PCT Pub. No.: WO2014/127201
PCT Pub. Date: Aug. 21, 2014

(65) Prior Publication Data
US 2015/0361125 A1 Dec. 17, 2015
US 2016/0251391 A9 Sep. 1, 2016

Related U.S. Application Data

(60) Provisional application No. 61/765,228, filed on Feb. 15, 2013.

(51) Int. Cl.
| | |
|---|---|
| *A61K 31/56* | (2006.01) |
| *A61K 31/566* | (2006.01) |
| *A61K 31/568* | (2006.01) |
| *A61K 31/5685* | (2006.01) |
| *C07J 1/00* | (2006.01) |
| *C07J 21/00* | (2006.01) |
| *C07J 15/00* | (2006.01) |
| *C07J 41/00* | (2006.01) |
| *C07C 35/42* | (2006.01) |
| *C07J 13/00* | (2006.01) |
| *C07J 31/00* | (2006.01) |
| *C07J 51/00* | (2006.01) |
| *C07J 61/00* | (2006.01) |
| *C07J 63/00* | (2006.01) |
| *C07J 71/00* | (2006.01) |
| *C07J 75/00* | (2006.01) |
| *C07C 43/307* | (2006.01) |

(52) U.S. Cl.
CPC ............ *C07J 1/00* (2013.01); *C07J 15/005* (2013.01); *C07J 21/00* (2013.01); *C07J 41/0094* (2013.01); *C07C 35/42* (2013.01); *C07C 43/307* (2013.01); *C07C 2603/26* (2017.05); *C07C 2603/40* (2017.05); *C07J 13/002* (2013.01); *C07J 21/008* (2013.01); *C07J 31/006* (2013.01); *C07J 51/00* (2013.01); *C07J 61/00* (2013.01); *C07J 63/008* (2013.01); *C07J 71/001* (2013.01); *C07J 75/005* (2013.01)

(58) Field of Classification Search
CPC ......... C07J 1/00; C07J 15/005; C07J 41/0094
USPC ........ 552/614, 615, 624, 633, 642, 649, 502
See application file for complete search history.

(56) References Cited

U.S. PATENT DOCUMENTS

| | | |
|---|---|---|
| 4,179,336 A | 12/1979 | Weber et al. |
| 5,925,630 A | 7/1999 | Upasani et al. |

FOREIGN PATENT DOCUMENTS

| | | |
|---|---|---|
| DE | 2632677 A1 | 1/1978 |
| WO | 2012083090 A2 | 6/2012 |

OTHER PUBLICATIONS

Fajkos, et al., "Steroids. XXIII. Synthesis and configuration of the two stereoisomeric 3β-hydroxy-16-acetylandrostanes," Chemicke Listy pro Vedu a Prumysl, vol. 50, pp. 791-799 (1956).
Heard, et al., "Steroids. VII. Preparation of androstan-3(β)-ol-7-one from dehydroisoandrosterone," Journal of Biological Chemistry, vol. 165, pp. 677-685 (1946).
Ruzicka, et al., "Steroids and sex hormones. CXXXIX. The relation between constitution and odor of steroids. Methylandrostane and allopregnane derivatives," Helvetica Chimica Acta, vol. 30, pp. 867-878 (1947).
International Search Report and Written Opinion for International Application No. PCT/US2014/016405 dated Jul. 16, 2014.
Hu et al., "Neurosteroid analogues. Part 5. Enantiomers of neuroactive steroids and benz[e]indenes: total synthesis, electrophysiological effects on GABAA receptor function and anesthetic actions in tadpoles", Journal of the Chemical Society, Jan. 1, 1997, No. 24, pp. 3665-3671.
Jacobs et al., "Studies on Vitamin D and Related Compounds XIX: Optical rotatory dispersion of some 9,10,13-stereoisomeric steroid 5,7-dienes", Recueil Des Travaux Chimiques Des Pays-Bas, 1965, vol. 84, No. 7, pp. 932-941.
Jennings et al., "Optical Ratatory Dispersion. Part XLIV. Steroid Acetates", Journal of the Chemical Society, Jan. 1, 1967, No. 11, pp. 1102-1108.
Katona et al., "Neurosteroid analogues. 12. Potent enhancement of GAB-mediated chloride currents at GABAA receptors by ent-androgens", European Journal of Medicinal Chemistry, Jan. 1, 2008, vol. 43, No. 1, pp. 107-113.
Katona et al., "Synthesis, Characterization, and Receptor Interaction Profiles of Enantiomeric Bile Acids", Journal of Medicinal Chemistry, Nov. 1, 2007, vol. 50, No. 24, pp. 6048-6058.

(Continued)

*Primary Examiner* — Barbara P Badio
(74) *Attorney, Agent, or Firm* — Armstrong Teasdale LLP

(57) ABSTRACT

The present disclosure is generally directed to neuroactive enantiomeric 15-, 16- and 17-substituted steroids with additional optional substituents at carbons 3, 4, 6, 7, 10 and 13, and pharmaceutically acceptable salts thereof, for use as, for example, modulators for GABA type-A receptors. The present disclosure is further directed to pharmaceutical compositions comprising such compounds.

16 Claims, 1 Drawing Sheet

(56) References Cited

OTHER PUBLICATIONS

Krishnan et al., "Neurosteroid Analogues. 17. Inverted Binding Orientations of Androsterone Enantiomers at the Steroid Potentiation Site on γ-Aminobutyric Acid Type A Receptors", Journal of Medicinal Chemistry, Feb. 9, 2012, vol. 55, No. 3, pp. 1334-1345.
Li et al., "Natural and Enantiomeric Etiocholanolone Interact with Distinct Sites on the Rat alpha1beta2gamma2L GABAA Receptor", Molecular Pharmacology, Jan. 1, 2007, vol. 71, No. 6, pp. 1582-1590.
Ohloff et al., "Structural and Configurational Dependence of the Sensory Process in Steroids", Helvetica Chimica Acta, Jan. 1, 1983, vol. 66, No. 20, pp. 192-217.
Paradiso et al., "Steroid Inhibition of Rat Neuronal Nicotinic α4β2 Receptors Expressed in HEK 293 Cells", Molecular Pharmacology, Jan. 1, 2000, vol. 58, No. 2, pp. 341-351.
Qian et al., "Neurosteroid Analogues. 18. Structure-Activity Studies of ent-Steroid Potentiators of γ-Aminobutyric Acid Type A Receptors and Comparison of Their Activities with Those of Alphaxalone and Allopregnanolone", Journal of Medicinal Chemistry, Jan. 9, 2014, vol. 57, No. 1, pp. 171-190.
Westover et al., "First synthesis of ent-desmosterol and its conversion to ent-deuterocholesterol", Steroids, Elsevier Science Publishers, vol. 68, No. 2, Feb. 1, 2003, vol. 28, No. 2, pp. 159-166.
European Search Report for EP 14 75 1289 dated Sep. 29, 2016, 15 pages.

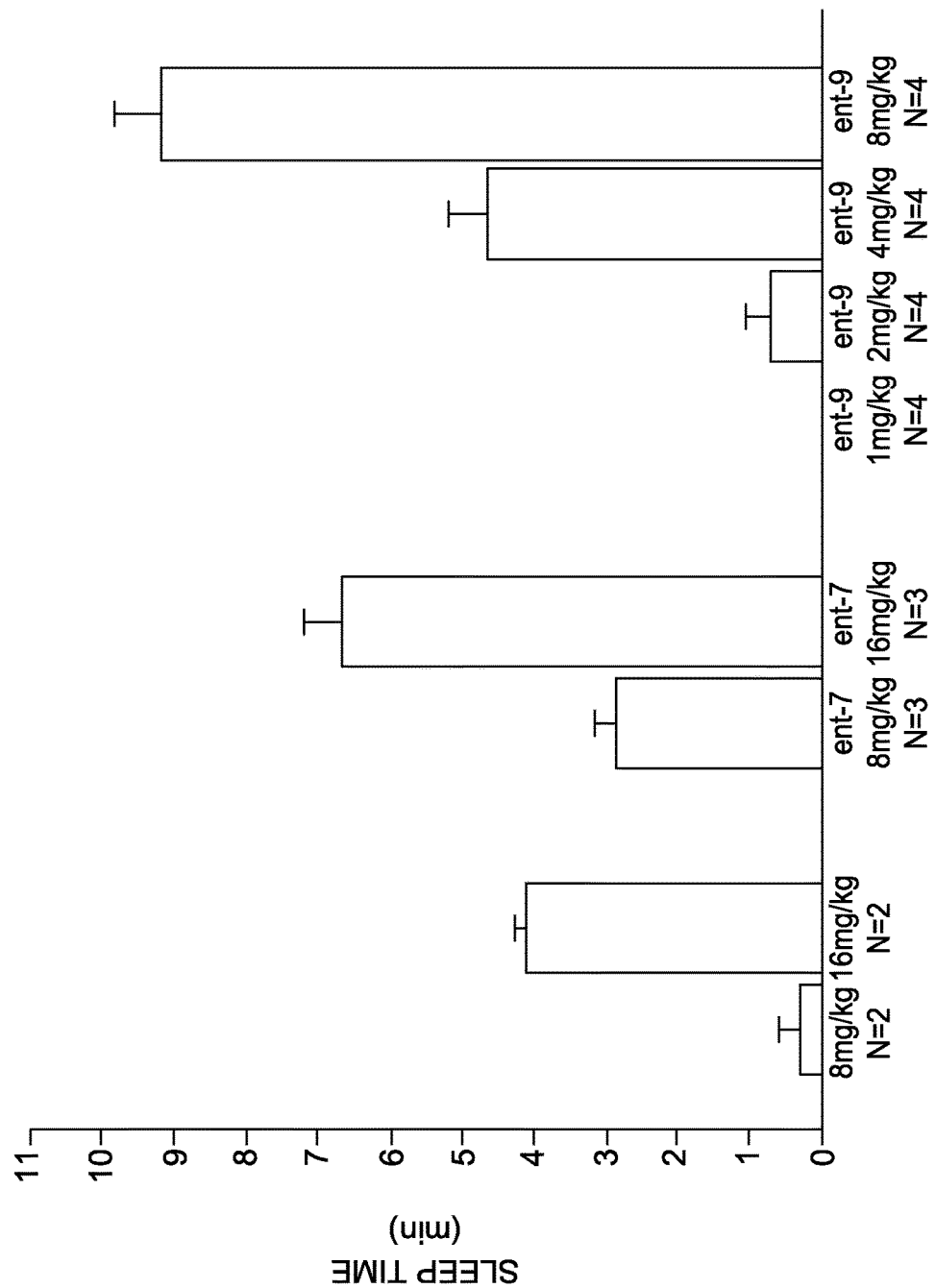

NEUROACTIVE ENANTIOMERIC 15-, 16- AND 17-SUBSTITUTED STEROIDS AS MODULATORS FOR GABA TYPE-A RECEPTORS

CROSS-REFERENCE TO RELATED APPLICATIONS

This application is a U.S. National Phase Patent Application of International Application Serial Number PCT/US2014/016405, filed Feb. 14, 2014, which is incorporated herein in its entirety, and which claims priority benefit of U.S. Provisional Patent Application Ser. No. 61/765,228, filed on Feb. 15, 2013, the entire contents of which are also incorporated herein by reference.

GOVERNMENT SUPPORT

The claimed subject matter was developed with Government support under NIH Grant #GM47969, awarded by the National Institute of Health. Accordingly, the Government has certain rights in the claimed subject matter.

BACKGROUND OF THE DISCLOSURE

The present disclosure is generally directed to novel compounds having utility as an anesthetic and/or in the treatment of disorders relating to GABA function and activity. More specifically, the present disclosure is directed to neuroactive enantiomeric 15-, 16- and 17-substituted steroids, and more specifically ent-steroids, with additional optional substituents at carbons 3, 4, 6, 7, 10 and 13, and pharmaceutically acceptable salts thereof for use as, for example, an anesthetic, as well as pharmaceutically acceptable salts thereof, and pharmaceutical compositions containing them. The present disclosure is generally directed to, for use as, for example, modulators for GABA type-A receptors. The present disclosure is further directed to pharmaceutical compositions comprising such compounds.

Gamma-aminobutyric acid (GABA) is the major inhibitory neurotransmitter of the central nervous system. GABA activates two types of receptors, the inotropic $GABA_A$ and the metabotropic $GABA_B$ receptor. Activation of the $GABA_B$ receptor by GABA causes hyperpolarization and a resultant inhibition of neurotransmitter release. The $GABA_A$ receptor subtype regulates neuronal excitability and rapid mood changes, such as anxiety, panic, and stress response. $GABA_A$ receptors are chloride ion channels; as a result, activation of the receptor induces increased inward chloride ion flux, resulting in membrane hyperpolarization and neuronal inhibition. Drugs that stimulate $GABA_A$ receptors, such as benzodiazepines and barbiturates, have anticonvulsive effects (by reducing neuronal excitability and raising the seizure threshold), as well as anxiolytic and anesthetic effects.

The effect of certain steroids on $GABA_A$ receptors has been well-established. As a result, researchers continue to pursue the discovery and synthesis of neuroactive steroids that may act as anesthetics and/or that may serve to provide treatment for disorders related to GABA function. In addition to anesthetic properties, neuroactive steroids may be used to treat disorders related to GABA function. For example, neuroactive steroids, such as progesterone, may be used as sedative-hypnotics, exhibiting benzodiazepine-like actions, inducing reduced sleep latency and increased non-REM sleep with only small changes in slow wave and REM sleep. Further, drugs that enhance GABA responses are often used to treat anxiety in humans. Thus, it might be expected that GABA-potentiating steroids would exhibit anxiolytic effects. Neuroactive steroids may also be used to treat depression, given that accumulating evidence suggests that patients with major depression have decreased levels of GABAergic neurosteroids and that certain treatments for depression alter levels of these steroids. Although GABA is not typically thought to play a critical role in the biology of depression, there is evidence that low GABAergic activity may predispose one to mood disorders. Finally, inhibition of NMDA receptors and enhancement of $GABA_A$ receptors appear to play important roles in mediating the acute effects of ethanol in the nervous system, while related studies suggest that GABAergic neurosteroids may be involved in some of the pharmacological effects of ethanol and that neuroactive steroids may be useful in treating ethanol withdrawal.

For example, the steroids nat-allopregnanolone (nat-1) and pregnanolone (nat-2) are known to function as allosteric modulators of $GABA_A$ receptor that enhance the actions of the neurotransmitter GABA.

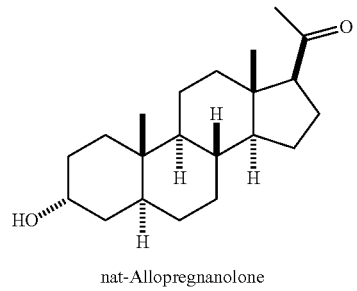

nat-Allopregnanolone

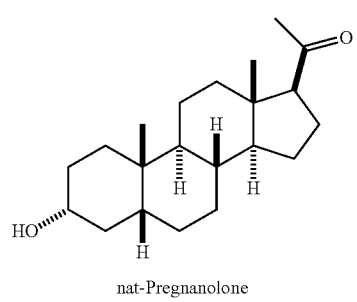

nat-Pregnanolone

The allosteric modulation of this receptor by the mirror images (enantiomers) of these compounds, ent-allopregnanolone (ent-1) and ent-pregnanolone (ent-2) are known to be weaker.

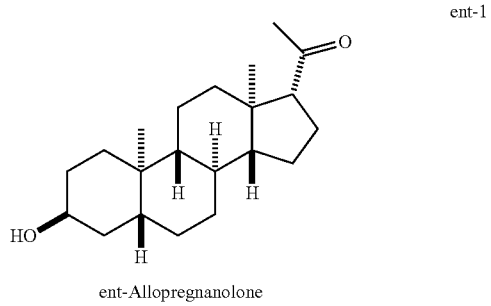

ent-Allopregnanolone

-continued

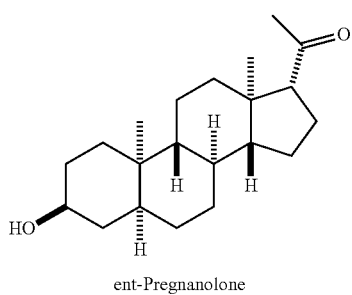

ent-Pregnanolone

Similarly, the steroids androsterone (nat-3) and etiocholanolone (nat-4) are also allosteric modulators of $GABA_A$ receptors.

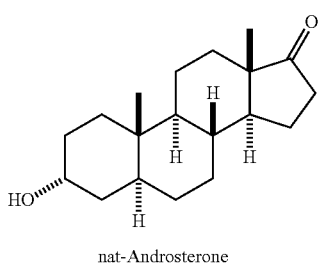

nat-Androsterone

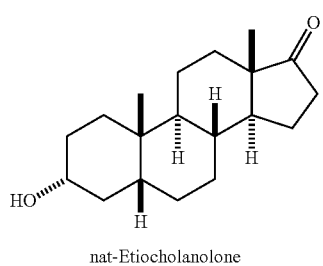

nat-Etiocholanolone

Surprisingly, the enantiomers of these two compounds, ent-androsterone (ent-3) and ent-etiocholanolone (ent-4), have greater activity than steroids nat-3 and nat-4. Androsterone and ent-androsterone are aligned at a common binding site on $GABA_A$ receptors.

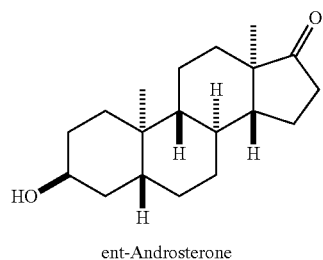

ent-Androsterone

-continued

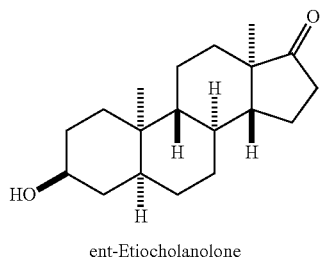

ent-Etiocholanolone

Because ent-3 and ent-4 are effective allosteric enhancers of GABA action at $GABA_A$ receptors, there is a need to research whether additional compounds having the absolute configuration of ent-3 and ent-4 could be effective allosteric modulators of $GABA_A$ receptor function.

In view of the foregoing, it is clear that there are a number of potentially advantageous uses for neurosteroids. As a result, there is a continuing need for the further synthesis and understanding of new neuroactive steroids, particularly those having utility as an anesthetic and/or in the treatment of a disorder relating to GABA function and activity.

The present disclosure has found previously unknown ent-steroids having this activity that are effective enhancers of $GABA_A$ receptor function.

SUMMARY OF THE DISCLOSURE

In one aspect, the present disclosure is directed to a compound having a structure of Formula (I):

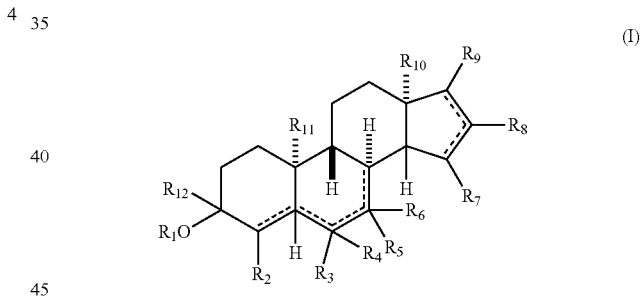

or a pharmaceutically acceptable salt thereof; wherein:

$R_1$ is H or —C(O)—$R_z$, where $R_z$ is optionally substituted $C_1$-$C_{20}$ alkyl;

$R_2$ is H, optionally substituted $C_1$-$C_4$ alkoxy, aryloxy, morpholinyl, optionally substituted $C_2$-$C_4$ alkenoxy, optionally substituted $C_2$-$C_4$ alkynoxy, or —O—C(O)—$R_x$, where $R_x$ is optionally substituted $C_1$-$C_{20}$ alkyl;

$R_3$ is H, OH, optionally substituted $C_1$-$C_4$ alkoxy, optionally substituted $C_2$-$C_4$ alkenoxy, optionally substituted $C_2$-$C_4$ alkynoxy, aryloxy, acetyl, substituted acetyl, cyano, nitro, spiroepoxide or —O—C(O)—$R_u$, where $R_u$ is optionally substituted $C_1$-$C_{20}$ alkyl;

$R_4$ is H, $C_1$-$C_4$ alkyl, $C_2$-$C_4$ alkenyl, $C_2$-$C_4$ alkynyl or —O—C(O)—$R_t$, where $R_t$ is optionally substituted $C_1$-$C_{20}$ alkyl;

with the proviso that when $R_3$ and $R_4$ are taken together, $R_3$ and $R_4$ combine to form =O or =$CR_y$, (where $R_y$ is CN, $CH_2NH_2$, C(O)—O—$R_w$ (where $R_w$ is H, optionally substituted $C_1$-$C_{10}$ or optionally substituted phenyl), or $CH_2OR_v$ (where $R_v$ is H, optionally substituted $C_1$-$C_{10}$, optionally substituted phenyl, or optionally substituted napthyl));

$R_5$ is H, OH, optionally substituted $C_1$-$C_4$ alkoxy, optionally substituted $C_2$-$C_4$ alkenoxy, optionally substituted $C_2$-$C_4$ alkynoxy, aryloxy, acetyl, substituted acetyl, cyano, nitro, spiroepoxide or —O—C(O)—$R_s$, where $R_s$ is optionally substituted $C_1$-$C_{20}$ alkyl;

$R_6$ is H, $C_1$-$C_4$ alkyl, $C_2$-$C_4$ alkenyl, $C_2$-$C_4$ alkynyl or —O—C(O)—$R_r$, where $R_r$ is optionally substituted $C_1$-$C_{20}$ alkyl;

with the proviso that when $R_5$ and $R_6$ are taken together, $R_5$ and $R_6$ combine to form =O or =$CR_q$, (where $R_q$ is CN, $CH_2NH_2$, C(O)—O—$R_p$ (where $R_p$ is H, optionally substituted $C_1$-$C_{10}$ or optionally substituted phenyl), or $CH_2OR_o$ (where $R_o$ is H, optionally substituted $C_1$-$C_{10}$, optionally substituted phenyl, or optionally substituted napthyl));

$R_7$ is H, optionally substituted $C_1$-$C_4$ alkoxy, optionally substituted $C_2$-$C_4$ alkenoxy, optionally substituted $C_2$-$C_4$ alkynoxy, spirooxirane, cyano, =O, nitro or optionally substituted $COCH_3$;

$R_8$ is H, optionally substituted $C_1$-$C_4$ alkoxy, optionally substituted $C_2$-$C_4$ alkenoxy, optionally substituted $C_2$-$C_4$ alkynoxy, spirooxirane, cyano, =O, =CHCN, nitro or optionally substituted $COCH_3$;

$R_9$ is H, optionally substituted $C_1$-$C_4$ alkoxy, spiroepoxide or =O;

$R_{10}$ is H, optionally substituted $C_1$-$C_4$ alkyl, optionally substituted $C_2$-$C_4$ alkenyl, or optionally substituted $C_2$-$C_4$ alkynyl;

$R_{11}$ is H, optionally substituted $C_1$-$C_4$ alkyl, optionally substituted $C_2$-$C_4$ alkenyl, or optionally substituted $C_2$-$C_4$ alkynyl;

$R_{12}$ is H, optionally substituted $C_1$-$C_4$ alkyl, optionally substituted $C_2$-$C_4$ alkenyl, or optionally substituted $C_2$-$C_4$ alkynyl; and,

- - - denotes an optional, additional C—C bond, resulting in a C=C bond between $C_4$-$C_5$, $C_5$-$C_6$, $C_6$-$C_7$, $C_7$-$C_8$, $C_{15}$-$C_{16}$, and/or $C_{16}$-$C_{17}$;

with the provisos that:

when $R_5$ is benzyloxy in the alpha configuration and $R_6$ is H, $R_9$ is other than =O or spiroepoxide;

when $R_1$-$R_8$ and $R_{12}$ are H, $R_{10}$ and $R_{11}$ are $CH_3$, $R_9$ is other than =O or spiroepoxide;

when $R_1$-$R_8$ and $R_{11}$-$R_{12}$ are H, $R_{10}$ is $CH_3$, and the $C_5$—H is in the alpha position, $R_9$ is other than =O; or, when a double bond is present between $C_5$-$C_6$, $R_1$ is other than H or $R_9$ is other than =O.

The present disclosure is still further directed to a pharmaceutical composition comprising a therapeutically effective amount of one or more of the above-noted enantiomeric steroids or pharmaceutically acceptable salts thereof, and optionally a pharmaceutically acceptable carrier. The present disclosure also provides kits comprising ent-steroids, salts thereof, and/or pharmaceutical compositions thereof.

The present disclosure further provides methods of inducing anesthesia in a subject in need thereof, the method comprising administering to the subject a therapeutically effective amount of one or more of the above-noted enantiomeric steroids, or pharmaceutically acceptable salts thereof, or a pharmaceutical composition thereof.

The present disclosure further provides methods of treating disorders related to GABA function in a subject in need thereof, the method comprising administering to the subject a therapeutically effective amount of one or more of the above-noted enantiomeric steroids, or pharmaceutically acceptable salts thereof, or a pharmaceutical composition thereof. In certain embodiments, the disorder is selected from the group consisting of insomnia, mood disorders, convulsive disorders, Fragile X syndrome, anxiety, or symptoms of ethanol withdrawal.

BRIEF DESCRIPTION OF THE DRAWING

FIG. 1 discloses graphical data of the duration of anesthesia induced by tail vein injections of compounds of the present disclosure relative to an anesthetic steroid.

DETAILED DESCRIPTION OF CERTAIN EMBODIMENTS

In accordance with the present disclosure, it has been discovered that compounds having an enantiomeric 15-, 16- and 17-substituted steroid, more specifically an ent-steroid, with additional optional substituents at carbons 3, 4, 6, 7, 10 and 13 structure are neuroactive and are also suitable for use as anesthetics and in the treatment of disorders associated with GABA function, as well as pharmaceutically acceptable salts thereof. The compounds may be used, for example, as an effective continuous infusion sedative for non-surgical procedures (e.g., colonoscopy). The compounds also offer advantages over anesthetics known in the art, such as a lower likelihood for bacterial contamination, as well as an improved relationship with solubilizing agents.

1. Steroid Structure

Generally speaking, the enantiomeric steroids (ent-steroids) of the present disclosure have the opposite absolute configuration of any naturally occurring steroids. The ent-steroid of the present disclosure has a tetracyclic, fused ring structure, such as a cyclopenta[a]phenanthrene ring system (an embodiment of which is illustrated and discussed in greater detail below), wherein the $C_3$, $C_4$, $C_6$, $C_7$, $C_{10}$ and $C_{13}$ positions have optional substituents in conjunction with an optional substituent at the $C_{15}$, $C_{16}$ and $C_{17}$ positions.

More particularly, however, the present disclosure is directed, in certain embodiments, to an ent-steroid having the structure of Formula (I):

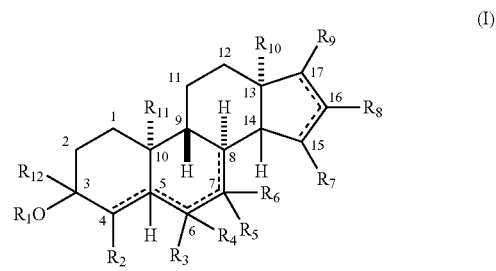

or a pharmaceutically acceptable salt thereof; wherein:

$R_1$ is H or —C(O)—$R_z$, where $R_z$ is optionally substituted $C_1$-$C_{20}$ alkyl;

$R_2$ is H, optionally substituted $C_1$-$C_4$ alkoxy, aryloxy, morpholinyl, optionally substituted $C_2$-$C_4$ alkenoxy, optionally substituted $C_2$-$C_4$ alkynoxy, or —O—C(O)—$R_x$, where $R_x$ is optionally substituted $C_1$-$C_{20}$ alkyl;

$R_3$ is H, OH, optionally substituted $C_1$-$C_4$ alkoxy, optionally substituted $C_2$-$C_4$ alkenoxy, optionally substituted $C_2$-$C_4$ alkynoxy, aryloxy, acetyl, substituted acetyl, cyano, nitro, spiroepoxide or —O—C(O)—$R_u$, where $R_u$ is optionally substituted $C_1$-$C_{20}$ alkyl;

$R_4$ is H, $C_1$-$C_4$ alkyl, $C_2$-$C_4$ alkenyl, $C_2$-$C_4$ alkynyl or —O—C(O)—$R_t$, where $R_t$ is optionally substituted $C_1$-$C_{20}$ alkyl;

with the proviso that when $R_3$=$R_4$, $R_3$ and $R_4$ are =O or =$CR_y$, (where $R_y$ is CN, $CH_2NH_2$, C(O)—O—$R_w$ (where $R_w$ is H, optionally substituted $C_1$-$C_{10}$ or optionally substituted phenyl), or $CH_2OR_v$ (where $R_v$ is H, optionally substituted $C_1$-$C_{10}$, optionally substituted phenyl, or optionally substituted napthyl));

$R_5$ is H, OH, optionally substituted $C_1$-$C_4$ alkoxy, optionally substituted $C_2$-$C_4$ alkenoxy, optionally substituted $C_2$-$C_4$ alkynoxy, aryloxy, acetyl, substituted acetyl, cyano, nitro, spiroepoxide or —O—C(O)—$R_s$, where $R_s$ is optionally substituted $C_1$-$C_{20}$ alkyl;

$R_6$ is H, $C_1$-$C_4$ alkyl, $C_2$-$C_4$ alkenyl, $C_2$-$C_4$ alkynyl or —O—C(O)—$R_r$, where $R_r$ is optionally substituted $C_1$-$C_{20}$ alkyl;

with the proviso that when $R_5$=$R_6$, $R_5$ and $R_6$ are =O or =$CR_q$, (where $R_q$ is CN, $CH_2NH_2$, C(O)—O—$R_p$ (where $R_p$ is H, optionally substituted $C_1$-$C_{10}$ or optionally substituted phenyl), or $CH_2OR_o$ (where $R_o$ is H, optionally substituted $C_1$-$C_{10}$, optionally substituted phenyl, or optionally substituted napthyl));

$R_7$ is H, optionally substituted $C_1$-$C_4$ alkoxy, optionally substituted $C_2$-$C_4$ alkenoxy, optionally substituted $C_2$-$C_4$ alkynoxy, spirooxirane, cyano, =O, nitro or optionally substituted $COCH_3$;

$R_8$ is H, optionally substituted $C_1$-$C_4$ alkoxy, optionally substituted $C_2$-$C_4$ alkenoxy, optionally substituted $C_2$-$C_4$ alkynoxy, spirooxirane, cyano, =O, =CHCN, nitro or optionally substituted $COCH_3$;

$R_9$ is H, optionally substituted $C_1$-$C_4$ alkoxy, spiroepoxide or =O;

$R_{10}$ is H, optionally substituted $C_1$-$C_4$ alkyl, optionally substituted $C_2$-$C_4$ alkenyl, or optionally substituted $C_2$-$C_4$ alkynyl;

$R_{11}$ is H, optionally substituted $C_1$-$C_4$ alkyl, optionally substituted $C_2$-$C_4$ alkenyl, or optionally substituted $C_2$-$C_4$ alkynyl;

$R_{12}$ is H, optionally substituted $C_1$-$C_4$ alkyl, optionally substituted $C_2$-$C_4$ alkenyl, or optionally substituted $C_2$-$C_4$ alkynyl; and,

- - - denotes an optional, additional C—C bond, resulting in a C=C bond between $C_4$-$C_5$, $C_5$-$C_6$, $C_6$-$C_7$, $C_7$-$C_8$, $C_{15}$-$C_{16}$, and/or $C_{16}$-$C_{17}$;

with the provisos that:

when $R_5$ is benzyloxy in the alpha configuration and $R_6$ is H, $R_9$ is other than =O or spiroepoxide;

when $R_1$-$R_8$ and $R_{12}$ are H, $R_{10}$ and $R_{11}$ are $CH_3$, $R_9$ is other than =O or spiroepoxide;

when $R_1$-$R_8$ and $R_{11}$-$R_{12}$ are H, $R_{10}$ is $CH_3$, and the $C_5$—H is in the alpha position, $R_9$ is other than =O; or, when a double bond is present between $C_5$-$C_6$, $R_1$ is other than H or $R_9$ is other than =O.

As generally defined above, $R_1$ is H or —C(O)—$R_z$, where $R_z$ is optionally substituted $C_1$-$C_{20}$ alkyl. In one embodiment, $R_z$ is optionally substituted $C_1$-$C_{15}$ alkyl, preferably optionally substituted $C_1$-$C_{10}$ alkyl, more preferably optionally substituted $C_1$-$C_4$ alkyl. In a preferred embodiment, $R_1$ is H. In another preferred embodiment, when $R_1$ is H, the OH at $C_3$ is in the beta configuration.

As generally defined above, $R_2$ is H, optionally substituted $C_1$-$C_4$ alkoxy, optionally substituted $C_2$-$C_4$ alkenoxy, optionally substituted $C_2$-$C_4$ alkynoxy, aryloxy, morpholinyl or —O—C(O)—$R_x$, where $R_x$ is optionally substituted $C_1$-$C_{20}$ alkyl. In one embodiment, $R_x$ is optionally substituted $C_1$-$C_{15}$ alkyl, preferably optionally substituted $C_1$-$C_{10}$ alkyl, more preferably optionally substituted $C_1$-$C_4$ alkyl. In one embodiment, $R_2$ is selected from the group consisting of H and methoxy (i.e., —$OCH_3$). In certain embodiments, $R_2$ is H. In other certain embodiments, $R_2$ is methoxy. In certain embodiments, $R_2$, when not H and no double bond is present between $C_4$-$C_5$, is in the alpha configuration. In certain embodiments, when $R_2$ is methoxy, $R_2$ is in the alpha configuration.

As generally defined above, $R_3$ is H, OH, optionally substituted $C_1$-$C_4$ alkoxy, optionally substituted $C_2$-$C_4$ alkenoxy, optionally substituted $C_2$-$C_4$ alkynoxy, aryloxy, acetyl, substituted acetyl, cyano, nitro, spiroepoxide or —O—C(O)—$R_u$, where $R_u$ is optionally substituted $C_1$-$C_{20}$ alkyl. In one embodiment, $R_u$ is optionally substituted $C_1$-$C_{15}$ alkyl, preferably optionally substituted $C_1$-$C_{10}$ alkyl, more preferably optionally substituted $C_1$-$C_4$ alkyl. In a preferred embodiment, $R_3$ is H, or, alternatively, $R_3$ is taken together with $R_4$ to be =O.

As generally defined above, $R_4$ is H, $C_1$-$C_4$ alkyl, $C_2$-$C_4$ alkenyl, $C_2$-$C_4$ alkynyl or —O—C(O)—$R_t$, where $R_t$ is optionally substituted $C_1$-$C_{20}$ alkyl. In one embodiment, $R_t$ is optionally substituted $C_1$-$C_{15}$ alkyl, preferably optionally substituted $C_1$-$C_{10}$ alkyl, more preferably optionally substituted $C_1$-$C_4$ alkyl. In a preferred embodiment, $R_4$ is H, or, alternatively, as noted above $R_4$ is taken together with $R_3$ to be =O.

As generally defined above, with respect to $R_3$ and $R_4$, when taken together, $R_3$ and $R_4$ combine to form =O or =$CR_y$, (where $R_y$ is CN, $CH_2NH_2$, C(O)—O—$R_w$ (where $R_w$ is H, optionally substituted $C_1$-$C_{10}$ or optionally substituted phenyl), or $CH_2OR_v$ (where $R_v$ is H, optionally substituted $C_1$-$C_{10}$, optionally substituted phenyl, or optionally substituted napthyl)).

As generally defined above, $R_5$ is H, OH, optionally substituted $C_1$-$C_4$ alkoxy, optionally substituted $C_2$-$C_4$ alkenoxy, optionally substituted $C_2$-$C_4$ alkynoxy, aryloxy, acetyl, substituted acetyl, cyano, nitro, spiroepoxide or —O—C(O)—$R_s$, where $R_s$ is optionally substituted $C_1$-$C_{20}$ alkyl. In one embodiment, $R_s$ is optionally substituted $C_1$-$C_{15}$ alkyl, preferably optionally substituted $C_1$-$C_{10}$ alkyl, more preferably optionally substituted $C_1$-$C_4$ alkyl. In a preferred embodiment, $R_5$ is H.

As generally defined above, $R_6$ is H, $C_1$-$C_4$ alkyl, $C_2$-$C_4$ alkenyl, $C_2$-$C_4$ alkynyl or —O—C(O)—$R_r$, where $R_r$ is optionally substituted $C_1$-$C_{20}$ alkyl. In one embodiment, $R_r$ is optionally substituted $C_1$-$C_{15}$ alkyl, preferably optionally substituted $C_1$-$C_{10}$ alkyl, more preferably optionally substituted $C_1$-$C_4$ alkyl. In a preferred embodiment, $R_6$ is H.

As generally defined above, with respect to $R_5$ and $R_6$, when taken together, $R_5$ and $R_6$ combine to form =O or =$CR_q$, (where $R_q$ is CN, $CH_2NH_2$, C(O)—O—$R_p$ (where $R_p$ is H, optionally substituted $C_1$-$C_{10}$ or optionally substituted phenyl), or $CH_2OR_o$ (where $R_o$ is H, optionally substituted $C_1$-$C_{10}$, optionally substituted phenyl, or optionally substituted napthyl)).

As generally defined above, $R_7$ is H, optionally substituted $C_1$-$C_4$ alkoxy, optionally substituted $C_2$-$C_4$ alkenoxy, optionally substituted $C_2$-$C_4$ alkynoxy, spirooxirane, cyano, =O, nitro or optionally substituted $COCH_3$. In a preferred embodiment, $R_7$ is H, or, alternatively, $R_7$ is —$OCH_3$. In certain embodiments, $R_7$, when not =O, is in the alpha configuration (e.g., when $R_7$ is —$OCH_3$).

As generally defined above, $R_8$ is H, optionally substituted $C_1$-$C_4$ alkoxy, optionally substituted $C_2$-$C_4$ alkenoxy, optionally substituted $C_2$-$C_4$ alkynoxy, spirooxirane, cyano, =O, =CHCN, nitro or optionally substituted $COCH_3$. In a preferred embodiment, $R_8$ is =O, or, alternatively, $R_8$ is —OCH$_3$, COCH$_3$, CN, or =CHCN. In certain embodiments, R$_8$, when not =O, is in the alpha configuration.

As generally defined above, R$_9$ is H, optionally substituted C$_1$-C$_4$ alkoxy, spiroepoxide or =O. In a preferred embodiment, R$_9$ is =O. In certain embodiments, R$_9$, when not =O, is in the alpha configuration.

As generally defined above, R$_{10}$ is H, optionally substituted C$_1$-C$_4$ alkyl, optionally substituted C$_2$-C$_4$ alkenyl, or optionally substituted C$_2$-C$_4$ alkynyl. In certain embodiments, R$_{10}$ is selected from the group consisting of H and methyl. In one embodiment, R$_{10}$ is H. In another embodiment, R$_{10}$ is methyl. R$_{10}$ is preferably in the alpha configuration.

As generally defined above, R$_{11}$ is H, optionally substituted C$_1$-C$_4$ alkyl, optionally substituted C$_2$-C$_4$ alkenyl, or optionally substituted C$_2$-C$_4$ alkynyl. In certain embodiments, R$_{11}$ is selected from the group consisting of H and methyl. In one embodiment, R$_{11}$ is H. In another embodiment, R$_{11}$ is methyl. R$_{11}$ is preferably in the alpha configuration.

As generally defined above, R$_{12}$ is H, optionally substituted C$_1$-C$_4$ alkyl, optionally substituted C$_2$-C$_4$ alkenyl, or optionally substituted C$_2$-C$_4$ alkynyl. In certain embodiments, R$_{12}$ is selected from the group consisting of H and methyl. In one embodiment, R$_{12}$ is H. In another embodiment, R$_{12}$ is methyl. In a preferred embodiment, when R$_{12}$ is methyl, R$_{12}$ is in the alpha configuration.

As generally defined above, - - - denotes an optional, additional C—C bond, resulting in either a C=C bond between C$_4$-C$_5$, C$_5$-C$_6$, C$_6$-C$_7$, C$_7$-C$_8$, C$_{15}$-C$_{16}$, and/or C$_{16}$-C$_{17}$ with the proviso that when present at C$_4$-C$_5$ or C$_5$-C$_6$, the C$_5$—H substituent is not present; when present at C$_5$-C$_6$ or C$_6$-C$_7$, one of R$_3$ and R$_4$ are not present; when present at C$_6$-C$_7$ or C$_7$-C$_8$, one of R$_5$ and R$_6$ are not present; and, when present at C$_7$-C$_8$, the C$_8$—H substituent is not present. When a C=C bond is present between C$_{15}$-C$_{16}$ or C$_{16}$-C$_{17}$, it is to be understood that a H (not shown) is absent from the carbon atoms between which the C=C is present.

In certain embodiments, the additional C—C bond(s) are absent, and the hydrogen at C$_5$ is in the alpha or beta position. In certain embodiments, the additional C—C bond is absent, and the hydrogen at C$_5$ is in the alpha (down) position. In certain embodiments, the additional C—C bond is absent, and the hydrogen at C$_5$ is in the beta (up) position.

In certain embodiments, the additional C—C bond(s) are absent, and the hydrogen at C$_8$ is in the alpha position. In other certain embodiments, the C$_9$—H substituent is in the beta configuration. In other certain embodiments, the C$_{14}$—H is in the beta configuration. In other certain embodiments, C$_{14}$—H is in the alpha configuration.

As generally defined above, when R$_5$ is benzyloxy in the alpha configuration and R$_6$ is H, R$_9$ is other than =O or spiroepoxide. Further, when R$_1$-R$_8$ and R$_{12}$ are H, R$_{10}$ and R$_{11}$ are CH$_3$, R$_9$ is other than =O or spiroepoxide. Additionally, when R$_1$-R$_8$ and R$_{11}$-R$_{12}$ are H, R$_{10}$ is CH$_3$, and the C$_5$—H is in the alpha position, R$_9$ is other than =O. Additionally, when a double bond is present between C$_5$-C$_6$, R$_1$ is other than H or R$_9$ is other than =O.

It is to be noted that the present disclosure contemplates and is intended to encompass all of the various combinations and permutations (i.e., combinations of substituent options, locations and stereochemical configurations) possible here, with the exception of those structures noted above.

Accordingly, as noted, the ent-steroid of Formula (I) may encompass a number of various structures in accordance with the present disclosure.

Exemplary compounds of Formula (I) include, but are not limited to, the following:

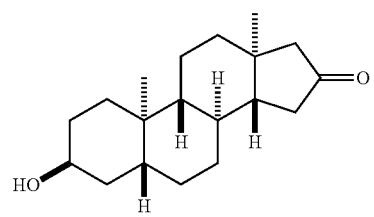
(MQ-35)

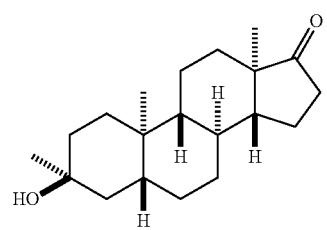
(KK-23)

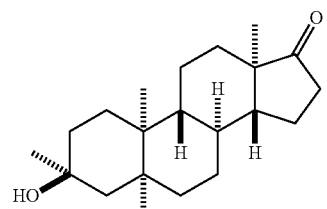
(KK-26)

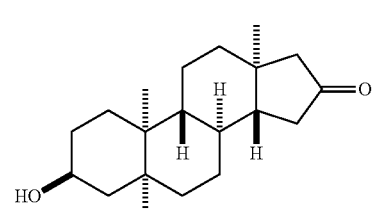
(KK-97)

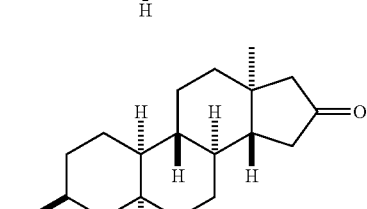
(KK-102)

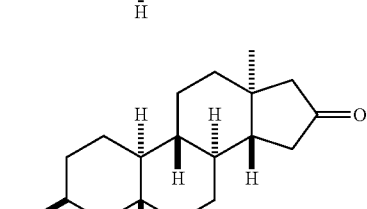
(KK-103)

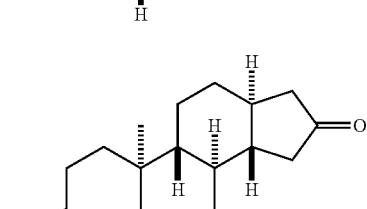
(KK-114)

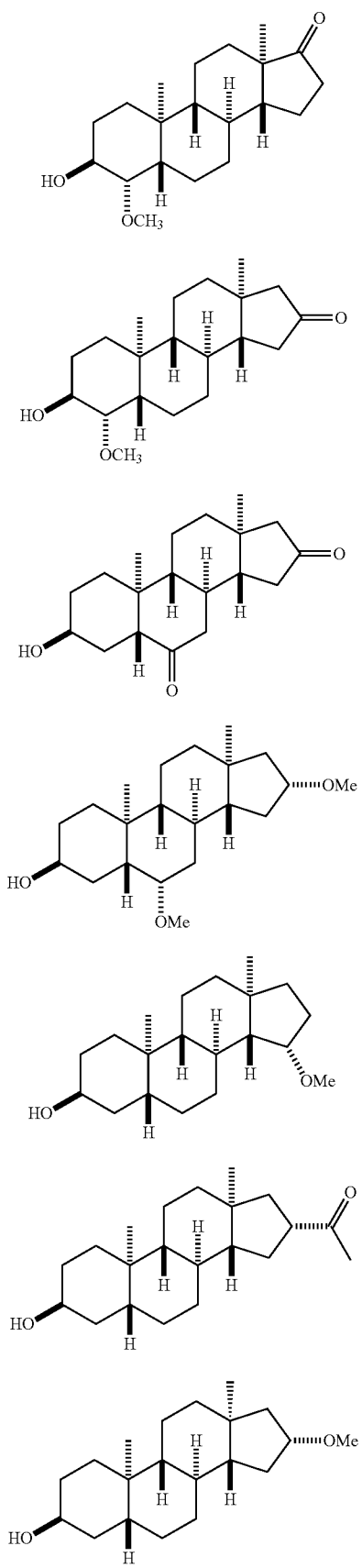

and pharmaceutically acceptable salts thereof.

In this regard it is to be noted that the structures provided above are of various exemplary embodiments. As such, they should not be viewed in a limiting sense.

2. Methods of Preparation and Pharmaceutical Compositions

It is to be noted that the compounds or ent-steroids of the present disclosure may in various embodiments be prepared or used in accordance with means generally known in the art. For example, in certain embodiments, the ent-steroids of the present disclosure may be prepared or used in a pharmaceutically acceptable salt form. Suitable salt forms include, for example, citrate or chloride salt forms.

In various embodiments of the present disclosure, a pharmaceutical composition is disclosed that may comprise an ent-steroid in accordance with the formulas of the present disclosure. The compounds or ent-steroids of the present disclosure, as well as the various salt forms and other pharmaceutically acceptable forms, e.g., solvates and/or hydrates of compounds described herein, and pharmaceutical compositions containing them, may in general be prepared using methods and techniques known in the art, and/or as described in the Examples provided herein.

Without wishing to be bound by any particular theory, the compounds or ent-steroids of the present disclosure are useful for potentiating GABA at $GABA_A$ receptors thereby inducing anesthesia or treating disorders related to GABA function (e.g., insomnia, mood disorders, Fragile X syndrome, convulsive disorders, anxiety disorders, or symptoms of ethanol withdrawal) in a subject, e.g., a human subject, and are preferably administered in the form of a pharmaceutical composition comprising an effective amount of a compound of the instant disclosure and optionally a pharmaceutically or pharmacologically acceptable carrier.

In one aspect, provided is a method of inducing anesthesia in a subject in need thereof, the method comprising administering to the subject a therapeutically effective amount of one or more of the above-noted ent-steroids, or pharmaceutically acceptable salts thereof, or a pharmaceutical composition thereof.

In another aspect, provided is a method of treating disorders related to GABA function in a subject in need thereof, the method comprising administering to the subject a therapeutically effective amount of one or more of the above-noted ent-steroids, or pharmaceutically acceptable salts thereof, or a pharmaceutical composition thereof. In certain embodiments, the disorder is selected from the group consisting of insomnia, mood disorders, convulsive disorders, Fragile X syndrome, anxiety, or symptoms of ethanol withdrawal.

In one embodiment of the present disclosure, a therapeutically effective amount of compound is from about 5 mg/kg to about 20 mg/kg, about 5 mg/kg to about 18 mg/kg, about 5 mg/kg to about 16 mg/kg, about 5 mg/kg to about 14 mg/kg, about 5 mg/kg to about 12 mg/kg, about 5 mg/kg to about 10 mg/kg, about 6 mg/kg to about 10 mg/kg, about 6 mg/kg to about 9 mg/kg, about 7 mg/kg to about 9 mg/kg, or about 8 mg/kg to about 16 mg/kg. In certain embodiments, a therapeutically effective amount of the compound is about 8 mg/kg. It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

The exact amount of a compound required to achieve an effective amount will vary from subject to subject, depending, for example, on species, age, and general condition of a subject, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations). In other certain embodiments, the compound may be administered via continuous intravenous (IV) infusion, such as used by those commonly skilled in the art of general anesthesia.

It will be also appreciated that a compound or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body.

The compound or composition can be administered concurrently with, prior to, or subsequent to, one or more additional therapeutically active agents. In general, each agent will be administered at a dose and/or on a time schedule determined for that agent. It will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually. Exemplary therapeutically active agents include small organic molecules such as drug compounds (e.g., compounds approved by the US Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells.

The pharmaceutical composition may also be in combination with at least one pharmacologically acceptable carrier. The carrier, also known in the art as an excipient, vehicle, auxiliary, adjuvant, or diluent, is any substance that is pharmaceutically inert, confers a suitable consistency or form to the composition, and does not diminish the therapeutic efficacy of the compounds. The carrier is "pharmaceutically or pharmacologically acceptable" if it does not produce an adverse, allergic, or other untoward reaction when administered to a mammal or human, as appropriate.

The pharmaceutical compositions containing the compounds or ent-steroids of the present disclosure may be formulated in any conventional manner. Proper formulation is dependent upon the route of administration chosen. The compositions of the disclosure can be formulated for any route of administration, so long as the target tissue is available via that route. Suitable routes of administration include, but are not limited to, oral, parenteral (e.g., intravenous, intraarterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual, and intestinal administration. In certain embodiments, the route of administration is oral. In certain embodiments, the route of administration is parenteral. In certain embodiments, the route of administration is intravenous.

Pharmaceutically acceptable carriers for use in the compositions of the present disclosure are well known to those of ordinary skill in the art and are selected based upon a number of factors, including for example: the particular compound used, and its concentration, stability and intended bioavailability; the disease, disorder or condition being treated with the composition; the subject, its age, size and general condition; and/or the route of administration. Suitable carriers may be readily determined by one of ordinary skill in the art. (See, for example, J. G. Nairn, in: Remington's Pharmaceutical Science (A. Gennaro, ed.), Mack Publishing Co., Easton, Pa., (1985), pp. 1492-1517.)

The compositions may be formulated as tablets, dispersible powders, pills, capsules, gelcaps, caplets, gels, liposomes, granules, solutions, suspensions, emulsions, syrups, elixirs, troches, dragees, lozenges, or any other dosage form that can be administered orally. Techniques and compositions for making oral dosage forms useful in the present disclosure are described in the following exemplary references: 7 Modern Pharmaceutics, Chapters 9 and 10 (Banker & Rhodes, Editors, 1979); Lieberman et al., Pharmaceutical Dosage Forms: Tablets (1981); and, Ansel, Introduction to Pharmaceutical Dosage Forms 2nd Edition (1976).

The compositions of the present disclosure designed for oral administration comprise an effective amount of a compound of the disclosure in a pharmaceutically acceptable carrier. Suitable carriers for solid dosage forms include sugars, starches, and other conventional substances including lactose, talc, sucrose, gelatin, carboxymethylcellulose, agar, mannitol, sorbitol, calcium phosphate, calcium carbonate, sodium carbonate, kaolin, alginic acid, acacia, corn starch, potato starch, sodium saccharin, magnesium carbonate, tragacanth, microcrystalline cellulose, colloidal silicon dioxide, croscarmellose sodium, talc, magnesium stearate, and stearic acid. Further, such solid dosage forms may be uncoated or may be coated by known techniques (e.g., to delay disintegration and absorption).

The ent-steroids of the present disclosure may also be formulated for parenteral administration (e.g., formulated for injection via intravenous, intraarterial, subcutaneous, rectal, subcutaneous, intramuscular, intraorbital, intracapsular, intraspinal, intraperitoneal, or intrasternal routes). The compositions of the present disclosure for parenteral administration comprise an effective amount of the compound in a pharmaceutically acceptable carrier. Dosage forms suitable for parenteral administration include solutions, suspensions, dispersions, emulsions or any other dosage form that can be administered parenterally. Techniques and compositions for making parenteral dosage forms are known in the art. Typically formulations for parenteral administration are sterile or are sterilized before administration.

Suitable carriers used in formulating liquid dosage forms for oral or parenteral administration include nonaqueous, pharmaceutically-acceptable polar solvents such as oils, alcohols, amides, esters, ethers, ketones, hydrocarbons and mixtures thereof, as well as water, saline solutions, dextrose solutions (e.g., DW5), electrolyte solutions, or any other aqueous, pharmaceutically acceptable liquid.

Suitable nonaqueous, pharmaceutically-acceptable polar solvents include, but are not limited to, alcohols (e.g., α-glycerol formal, β-glycerol formal, 1,3-butyleneglycol, aliphatic or aromatic alcohols having 2-30 carbon atoms such as methanol, ethanol, propanol, isopropanol, butanol, t-butanol, hexanol, octanol, amylene hydrate, benzyl alcohol, glycerin (glycerol), glycol, hexylene glycol, tetrahydrofurfuryl alcohol, lauryl alcohol, cetyl alcohol, or stearyl alcohol, fatty acid esters of fatty alcohols such as polyalkylene glycols (e.g., polypropylene glycol, polyethylene glycol), sorbitan, sucrose and cholesterol); amides (e.g., dimethylacetamide (DMA), benzyl benzoate DMA, dimethylformamide, N-(β-hydroxyethyl)-lactamide, N,N-dimethylacetamide, 2-pyrrolidinone, 1-methyl-2-pyrrolidinone, or polyvinylpyrrolidone); esters (e.g., 1-methyl-2-pyrrolidinone, 2-pyrrolidinone, acetate esters such as monoacetin, diacetin, and triacetin, aliphatic or aromatic esters such as ethyl caprylate or octanoate, alkyl oleate, benzyl benzoate, benzyl acetate, dimethylsulfoxide (DMSO), esters of glycerin such as mono, di, or tri-glyceryl citrates or tartrates, ethyl benzoate, ethyl acetate, ethyl carbonate, ethyl lactate, ethyl oleate, fatty acid esters of sorbitan, fatty acid derived PEG esters, glyceryl monostearate, glyceride esters such as mono, di, or tri-glycerides, fatty acid esters such as isopropyl myristate, fatty acid derived PEG esters such as PEG-hydroxyoleate and PEG-hydroxystearate, N-methyl pyrrolidinone, pluronic 60, polyoxyethylene sorbitol oleic polyesters such as poly(ethoxylated)$_{30-60}$ sorbitol poly(oleate)$_{2-4}$, poly(oxyethylene)$_{15-20}$ monooleate, poly(oxyethylene)$_{15-20}$ mono 12-hydroxystearate, and poly(oxyethylene)$_{15-20}$ mono-ricinoleate, polyoxyethylene sorbitan esters (such as polyoxyethylene-sorbitan monooleate, polyoxyethylene-sorbitan monopalmitate, polyoxyethylene-sorbitan monolaurate, polyoxyethylene-sorbitan monostearate, and POLYSORBATE® 20, 40, 60 or 80 from ICI Americas, Wilmington, Del.), polyvinylpyrrolidone, alkyleneoxy modified fatty acid esters (such as polyoxyl 40 hydrogenated castor oil, cyclodextrins or modified cyclodextrins (e.g., beta-hydroxypropyl-cyclodextrin)), saccharide fatty acid esters (i.e., the condensation product of a monosaccharide (e.g., pentoses, such as ribose, ribulose, arabinose, xylose, lyxose and xylulose, hexoses such as glucose, fructose, galactose, mannose and sorbose, trioses, tetroses, heptoses, and octoses), disaccharide (e.g., sucrose, maltose, lactose and trehalose) or oligosaccharide or mixture thereof with a $C_4$-$C_{22}$ fatty acid(s)(e.g., saturated fatty acids such as caprylic acid, capric acid, lauric acid, myristic acid, palmitic acid and stearic acid, and unsaturated fatty acids such as palmitoleic acid, oleic acid, elaidic acid, erucic acid and linoleic acid)), or steroidal esters); alkyl, aryl, or cyclic ethers having 2-30 carbon atoms (e.g., diethyl ether, tetrahydrofuran, dimethyl isosorbide, diethylene glycol monoethyl ether); glycofurol (tetrahydrofurfuryl alcohol polyethylene glycol ether); ketones having 3-30 carbon atoms (e.g., acetone, methyl ethyl ketone, methyl isobutyl ketone); aliphatic, cycloaliphatic or aromatic hydrocarbons having 4-30 carbon atoms (e.g., benzene, cyclohexane, dichloromethane, dioxolanes, hexane, n-decane, n-dodecane, n-hexane, sulfolane, tetramethylenesulfone, tetramethylenesulfoxide, toluene, dimethylsulfoxide (DMSO), or tetramethylenesulfoxide); oils of mineral, vegetable, animal, essential or synthetic origin (e.g., mineral oils such as aliphatic or wax-based hydrocarbons, aromatic hydrocarbons, mixed aliphatic and aromatic based hydrocarbons, and refined paraffin oil, vegetable oils such as linseed, tung, safflower, soybean, castor, cottonseed, groundnut, rapeseed, coconut, palm, olive, corn, corn germ, sesame, persic and peanut oil and glycerides such as mono-, di- or triglycerides, animal oils such as fish, marine, sperm, cod-liver, haliver, squalene, squalane, and shark liver oil, oleic oils, and polyoxyethylated castor oil); alkyl or aryl halides having 1-30 carbon atoms and optionally more than one halogen substituent; methylene chloride; monoethanolamine; petroleum benzine; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (SOLUTOL® HS-15, from BASF, Ludwigshafen, Germany); polyoxyethylene glycerol; sodium laurate; sodium oleate; or sorbitan monooleate.

Other pharmaceutically acceptable solvents for use in the disclosure are well known to those of ordinary skill in the art, and are identified in The Handbook of Pharmaceutical Excipients, (American Pharmaceutical Association, Washington, D.C., and The Pharmaceutical Society of Great Britain, London, England, 1968), Modern Pharmaceutics, (G. Banker et al., eds., 3d ed.)(Marcel Dekker, Inc., New York, N.Y., 1995), The Pharmacological Basis of Therapeutics, (Goodman & Gilman, McGraw Hill Publishing), Pharmaceutical Dosage Forms, (H. Lieberman et al., eds.,) (Marcel Dekker, Inc., New York, N.Y., 1980), Remington's Pharmaceutical Sciences (A. Gennaro, ed., 19th ed.)(Mack Publishing, Easton, Pa., 1995), The United States Pharmacopeia 24, The National Formulary 19, (National Publishing, Philadelphia, Pa., 2000), A. J. Spiegel et al., and Use of Nonaqueous Solvents in Parenteral Products, J. of Pharm. Sciences, Vol. 52, No. 10, pp. 917-927 (1963).

Preferred solvents include cyclodextrins or modified cyclodextrins (e.g., beta-hydroxypropyl-cyclodextrin) as well as oils rich in triglycerides, for example, safflower oil, soybean oil or mixtures thereof, and alkyleneoxy modified fatty acid esters such as polyoxyl 40 hydrogenated castor oil. Commercially available triglycerides include INTRALIPID® emulsified soybean oil (Kabi-Pharmacia Inc., Stockholm, Sweden), NUTRALIPID® emulsion (McGaw, Irvine, Calif.), LIPOSYN® II 20% emulsion (a 20% fat emulsion solution containing 100 mg safflower oil, 100 mg soybean oil, 12 mg egg phosphatides, and 25 mg glycerin per ml of solution; Abbott Laboratories, Chicago, Ill.), LIPOSYN® III 2% emulsion (a 2% fat emulsion solution containing 100 mg safflower oil, 100 mg soybean oil, 12 mg egg phosphatides, and 25 mg glycerin per ml of solution; Abbott Laboratories, Chicago, Ill.), natural or synthetic glycerol derivatives containing the docosahexaenoyl group at levels between 25% and 100% by weight based on the total fatty acid content (DHASCO® (from Martek Biosciences Corp., Columbia, Md.), DHA MAGURO® (from Daito Enterprises, Los Angeles, Calif.), SOYACAL®, and TRAVEMULSION®.

Additional minor components can be included in the compositions of the disclosure for a variety of purposes well known in the pharmaceutical industry. These components will for the most part impart properties which enhance retention of the compound at the site of administration, protect the stability of the composition, control the pH, facilitate processing of the compound into pharmaceutical formulations, and the like. Preferably, each of these components is individually present in less than about 15 wt % of the total composition, more preferably less than about 5 wt %, and most preferably less than about 0.5 wt % of the total composition. Some components, such as fillers or diluents, can constitute up to 90 wt % of the total composition, as is well known in the formulation art. Such additives include cryoprotective agents for preventing reprecipitation, surface active, wetting or emulsifying agents (e.g., lecithin, polysorbate-80, TWEEN® 80, Pluronic 60, polyoxyethylene stearate), preservatives (e.g., ethyl-p-hydroxybenzoate), microbial preservatives (e.g., benzyl alcohol, phenol, m-cresol, chlorobutanol, sorbic acid, thimerosal and paraben), agents for adjusting pH or buffering agents (e.g., acids, bases, sodium acetate, sorbitan monolaurate), agents for adjusting osmolarity (e.g., glycerin), thickeners (e.g., aluminum monostearate, stearic acid, cetyl alcohol, stearyl alcohol, guar gum, methyl cellulose, hydroxypropylcellulose, tristearin, cetyl wax esters, polyethylene glycol), colorants, dyes, flow aids, non-volatile silicones (e.g., cyclomethicone), clays (e.g., bentonites), adhesives, bulking agents, flavorings, sweeteners, adsorbents, fillers (e.g., sugars such as lactose, sucrose, mannitol, or sorbitol, cellulose, or calcium phosphate), diluents (e.g., water, saline, electrolyte solutions), binders (e.g., starches such as maize starch, wheat starch, rice starch, or potato starch, gelatin, gum tragacanth, methyl cellulose, hydroxypropyl methylcellulose, sodium carboxymethyl cellulose, polyvinylpyrrolidone, sugars, polymers, acacia), disintegrating agents (e.g., starches such as maize starch, wheat starch, rice starch, potato starch, or carboxymethyl starch, cross-linked polyvinyl pyrrolidone, agar, alginic acid or a salt thereof such as sodium alginate, croscarmellose sodium or crospovidone), lubricants (e.g., silica, talc, stearic acid or salts thereof such as magnesium stearate, or polyethylene glycol), coating agents (e.g., concentrated sugar solutions including gum arabic, talc, polyvinyl pyrrolidone, carbopol gel, polyethylene glycol, or titanium dioxide), and antioxidants (e.g., sodium metabisulfite, sodium bisulfite, sodium sulfite, dextrose, phenols, and thiophenols).

Dosage from administration by these routes may be continuous or intermittent, depending, for example, upon the patient's physiological condition, whether the purpose of the administration is therapeutic or prophylactic, and other factors known to and assessable by a skilled practitioner.

Those with ordinary skill in administering anesthetics can readily determine dosage and regimens for the administration of the pharmaceutical compositions of the disclosure or titrating to an effective dosage for use in treating insomnia, mood disorders, convulsive disorders, anxiety or symptoms of ethanol withdrawal. It is understood that the dosage of the compounds will be dependent upon the age, sex, health, and weight of the recipient, kind of concurrent treatment, if any, frequency of treatment, and the nature of the effect desired. For any mode of administration, the actual amount of compound delivered, as well as the dosing schedule necessary to achieve the advantageous effects described herein, will also depend, in part, on such factors as the bioavailability of the compound, the disorder being treated, the desired therapeutic dose, and other factors that will be apparent to those of skill in the art. The dose administered to an animal, particularly a human, in the context of the present disclosure should be sufficient to affect the desired therapeutic response in the animal over a reasonable period of time. Preferably, an effective amount of the compound, whether administered orally or by another route, is any amount that would result in a desired therapeutic response when administered by that route. The dosage may vary depending on the dosing schedule, which can be adjusted as necessary to achieve the desired therapeutic effect. The most preferred dosage will be tailored to the individual subject, as is understood and determinable by one of ordinary skill in the art without undue experimentation.

In one embodiment, solutions for oral administration are prepared by dissolving the compound in any pharmaceutically acceptable solvent capable of dissolving a compound (e.g., ethanol or methylene chloride) to form a solution. An appropriate volume of a carrier which is a solution, such as beta-hydroxypropyl-cyclodextrin, is added to the solution while stirring to form a pharmaceutically acceptable solution for oral administration to a patient. If desired, such solutions can be formulated to contain a minimal amount of, or to be free of, ethanol, which is known in the art to cause adverse physiological effects when administered at certain concentrations in oral formulations.

In another embodiment, powders or tablets for oral administration are prepared by dissolving a compound in any pharmaceutically acceptable solvent capable of dissolving the compound (e.g., ethanol or methylene chloride) to form a solution. The solvent can optionally be capable of evaporating when the solution is dried under vacuum. An additional carrier can be added to the solution prior to drying, such as beta-hydroxypropyl-cyclodextrin. The resulting solution is dried under vacuum to form a glass. The glass is then mixed with a binder to form a powder. The powder can be mixed with fillers or other conventional tabletting agents and processed to form a tablet for oral administration to a patient. The powder can also be added to any liquid carrier as described above to form a solution, emulsion, suspension or the like for oral administration.

Emulsions for parenteral administration can be prepared by dissolving a compound in any pharmaceutically acceptable solvent capable of dissolving the compound (e.g., ethanol or methylene chloride) to form a solution. An appropriate volume of a carrier which is an emulsion, such as LIPOSYN® II or LIPOSYN® III emulsions, is added to the solution while stirring to form a pharmaceutically acceptable emulsion for parenteral administration to a patient.

Solutions for parenteral administration can be prepared by dissolving a compound in any pharmaceutically acceptable solvent capable of dissolving the compound (e.g., ethanol or methylene chloride) to form a solution. An appropriate volume of a carrier which is a solution, such as beta-hydroxypropyl-cyclodextrin, is added to the solution while stirring to form a pharmaceutically acceptable solution for parenteral administration to a patient.

If desired, the emulsions or solutions described above for oral or parenteral administration can be packaged in IV bags, vials or other conventional containers in concentrated form and diluted with any pharmaceutically acceptable liquid, such as saline, to form an acceptable concentration prior to use as is known in the art.

Still further encompassed by the disclosure are kits (e.g., pharmaceutical packs). The kits provided may comprise a compound as described herein and a container (e.g., a vial, ampule, bottle, syringe, and/or dispenser package, or other suitable container). In some embodiments, provided kits may optionally further include a second container comprising a pharmaceutical carrier for dilution or suspension of the pharmaceutical composition or compound. In some embodiments, the pharmaceutical composition or compound provided in the container and the second container are combined to form one unit dosage form.

Optionally, instructions for use are additionally provided in such kits of the disclosure. Such instructions may provide, generally, for example, instructions for dosage and administration. In other embodiments, instructions may further provide additional detail relating to specialized instructions for particular containers and/or systems for administration. Still further, instructions may provide specialized instructions for use in conjunction and/or in combination with an additional therapeutic agent.

3. Definitions

The term "ent-steroid" as used herein describes an organic compound containing in its chemical nucleus the cyclopenta[a]phenanthrene ring system that is the mirror image of a naturally occurring steroid or synthetic analogue derived from a naturally occurring steroid.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in J. Pharmaceutical Sciences, 1977, 66, 1-19. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As used herein, a "subject" to which administration is contemplated includes, but is not limited to, mammals, e.g., humans (i.e., a male or female of any age group, e.g., a pediatric subject (e.g., child, adolescent) or adult subject (e.g., young adult, middle-aged adult or senior adult)), other primates (e.g., cynomolgus monkeys, rhesus monkeys) and commercially relevant mammals such as cattle, pigs, horses, sheep, goats, cats, and/or dogs. In any aspect and/or embodiment of the disclosure, the subject is a human.

As used herein, a "therapeutically effective amount" "an amount sufficient" or "sufficient amount" of a compound means the level, amount or concentration of the compound required for a desired biological response, e.g., analgesia.

The term "saturated" as used herein describes the state in which all available valence bonds of an atom (especially carbon) are attached to other atoms.

The term "unsaturated" as used herein describes the state in which not all available valence bonds along the alkyl chain are satisfied; in such compounds the extra bonds usually form double or triple bonds (chiefly with carbon).

When a range of values is listed, it is intended to encompass each value and sub-range within the range. For example "$C_1$-4 alkyl" is intended to encompass, $C_1$, $C_2$, $C_3$, $C_4$, $C_{1-3}$, $C_{1-2}$, $C_{2-4}$, $C_{2-3}$ and $C_{3-4}$ alkyl, while "$C_{1-20}$ alkyl" is intended to encompass, for example, $C_1$, $C_2$, $C_3$, $C_4$, etc., as well as $C_{1-20}$, $C_{1-15}$, $C_{1-10}$, $C_{2-20}$, $C_{2-15}$, $C_{2-10}$, $C_{3-15}$, $C_{3-10}$, etc. alkyl.

As used herein, "alkyl" refers to a radical of a straight-chain or branched saturated hydrocarbon group having from, in some embodiments, 1 to 4 carbon atoms ("$C_{1-4}$ alkyl"), and in other embodiments 1 to 22 carbon atoms ("$C_{1-22}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 4 carbon atom ("$C_{2-4}$ alkyl"). In yet other embodiments, an alkyl group has 1 to 21 carbon atoms ("$C_{1-21}$ alkyl"), 1 to 20 carbon atoms ("$C_{1-20}$ alkyl"), 1 to 15 carbon atoms ("$C_{1-15}$ alkyl"), 1 to 10 carbon atoms ("$C_{1-10}$ alkyl"), etc. Examples of such alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), pentyl ($C_5$), and the like.

As used herein, "alkenyl" or "alkene" refers to a radical of a straight-chain or branched hydrocarbon group having from, in some embodiments, 2 to 4 carbon atoms ("$C_{2-4}$ alkenyl"), and in other embodiments 2 to 22 carbon atoms ("$C_{2-22}$ alkenyl"), and one or more carbon-carbon double bonds. In some embodiments, an alkenyl group has 2 to 3 carbon atoms ("$C_{2-3}$ alkenyl"). In some embodiments, an alkenyl group has 2 carbon atoms ("$C_2$ alkenyl"). In yet other embodiments, an alkenyl group has 2 to 21 carbon atoms ("$C_{2-21}$ alkenyl"), 2 to 20 carbon atoms ("$C_{2-20}$ alkenyl"), 2 to 15 carbon atoms ("$C_{2-15}$ alkenyl"), 2 to 10 carbon atoms ("$C_{2-10}$ alkyl"), etc. The one or more carbon-carbon double bonds can be internal (such as in 2-butenyl) or terminal (such as in 1-butenyl). Examples of such alkenyl groups include ethenyl ($C_2$), 1-propenyl ($C_3$), 2-propenyl ($C_3$), 1-butenyl ($C_4$), 2-butenyl ($C_4$), butadienyl ($C_4$), 1-pentenyl ($C_5$), 2-pentenyl ($C_5$), and the like.

As used herein, "alkynyl" or "alkyne" refers to a radical of a straight-chain or branched hydrocarbon group having from 2 to 4 carbon atoms and one or more carbon-carbon triple bonds ("$C_{2-10}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like.

As used herein, "aryl" refers to a radical of a monocyclic or polycyclic (e.g., bicyclic or tricyclic) 4n+2 aromatic ring system (e.g., having 6, 10, or 14 electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl).

As used herein, "alkoxy" refers to an alkyl, alkenyl, or alkynyl group, as defined herein, attached to an oxygen radical.

Alkyl, alkenyl, alkynyl, and aryl groups, as defined herein, are substituted or unsubstituted, also referred to herein as "optionally substituted". In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that result in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

As used herein, "spiroepoxide" refers to an epoxide formed from an exocyclic double bond on a ring.

Exemplary substituents include groups that contain a heteroatom (such as nitrogen, oxygen, silicon, phosphorous, boron, sulfur, or a halogen atom), halogen (e.g., chlorine, bromine, fluorine, or iodine), a heterocycle, alkoxy, alkenoxy, alkynoxy, aryloxy, hydroxy, protected hydroxy, spiroepoxide, keto, acyl, acyloxy, nitro, amino, amido, nitro, cyano, thiol, spirooxirane, ketals, acetals, esters and ethers.

EXAMPLES

The following Examples describe or illustrate various embodiments of the present disclosure. Other embodiments within the scope of the appended claims will be apparent to a skilled artisan considering the specification or practice of the disclosure as described herein. It is intended that the specification, together with the Examples, be considered exemplary only, with the scope and spirit of the disclosure being indicated by the claims, which follow the Examples.*

Compound Chemistry

In accordance with the following methods and Examples, the following compounds were prepared for purposes of illustration.

General Methods.

Solvents were either used as purchased or dried and purified by standard methodology. Extraction solvents were dried with anhydrous $Na_2SO_4$ and after filtration, removed under reduced pressure on a rotary evaporator. Flash column chromatography was performed using silica gel (32-63 μm) purchased from Scientific Adsorbents (Atlanta, Ga.). Melting points were determined on a Kofler micro hot stage and are uncorrected. FT-IR spectra were recorded as films on a NaCl plate. NMR spectra were recorded in $CDCl_3$ at ambient temperature at 300 or 400 MHz ($^1H$), 74 or 100 MHz ($^{13}C$).

Scheme 1

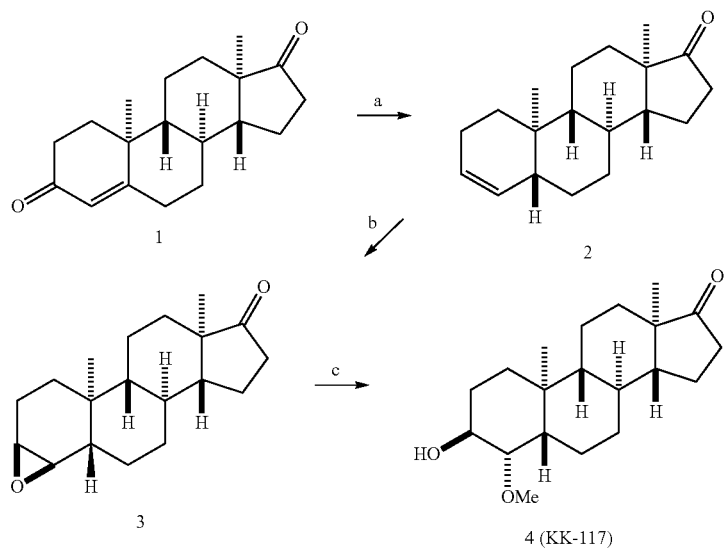

In accordance with Scheme 1, the following compounds were prepared, using methods generally known in the art and as outlined below.

1

(8α,9β,10α,13α,14β)-Androst-4-ene-3,17-dione (1)

This compound was prepared as previously described. (Nilsson, K. R.; Zorumski, C. F.; Covey, D. F. Neurosteroid analogues. 6. The synthesis and GABA$_A$ receptor pharmacology of enantiomers of dehydroepiandrosterone sulfate, pregnenolone sulfate, and (3α,5β)-3-hydroxypregnan-20-one sulfate. *J. Med. Chem.* 1998, 41, 2604-2613.)

2

(5β,8α,9β,10α,13α,14β)-Androst-3-en-17-one (2)

To a boiling solution of compound 1 (750 mg, 2.63 mmol) in glacial AcOH (40 mL), Zn dust (4.5 g) was added in several portions during a period of 15 min and then heating was continued an additional 15 min. The reaction was cooled, and the Zn dust was filtered, and the filtrate was collected. The filter-cake was washed with AcOH and EtOAc. Solvents were removed from the combined filtrates and washings, water was added to the residue and the product was extracted into EtOAc. The combined extracts were washed with aqueous NaHCO$_3$, brine, dried and solvents were evaporated to give a white solid which is a mixture (2.3:1 by NMR) of product 2 and the epimeric (5α)-3-ene product. The product mixture was crystallized from hexanes to give pure product 2 (310 mg, 43%): mp 122-125° C.; IR $v_{max}$ 3016, 2968, 2940, 2837, 2807, 1742, 1470, 1443, 1376, 1251 cm$^{-1}$; $^1$H NMR (CDCl$_3$) δ 5.60 (m, 1H), 5.29 (m, 1H), 2.44 (dd, 1H, J=19.0 Hz, 9.0 Hz), 0.88 (s, 3H), 0.80 (s, 3H); $^{13}$C NMR (CDCl$_3$) δ 221.3, 131.0 125.6, 53.5, 51.5, 47.9, 45.9, 35.8, 35.1, 35.0, 34.0, 31.6, 30.9, 27.1, 23.4, 21.8, 20.3, 13.9, 11.8.

3

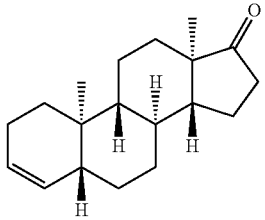

(3β,4β,5β,8α,9β,10α,13α,14β)-3,4-Epoxyandrostan-17-one (3)

Formic acid (0.42 mL) followed by 30% H$_2$O$_2$ (1 mL) was added to a solution of compound 2 (295 mg, 1.08 mmol) in stirred CH$_2$Cl$_2$ (15 mL) and stirring was continued at room temperature for 4 h. MeOH (10 mL) was added and after stirring for 3 min, 10% aqueous NaOH (5 mL) was added and stirring was continued for 5 min. 10% HCl (6 mL) was then added dropwise and stirring was continued for 3 min. The product was extracted into $CH_2Cl_2$ (3×75 ml) and the combined organic extracts were dried and concentrated to give an oil. After flash column chromatography (silica gel eluted with 20-30% EtOAc in hexanes) product 3 was obtained as a white solid (300 mg, 84%): mp 148-150° C.; IR $v_{max}$ 2928, 2882, 2859, 1740, 1472, 1446, 1405, 1373, 1251 cm$^{-1}$; $^1$H NMR (CDCl$_3$) δ 3.09 (s, 1H), 2.63 (d, 1H, J=3.9 Hz), 2.36 (dd, 1H, J=19.6 Hz, 9.0 Hz), 0.79 (s, 3H), 0.73 (s, 3H); $^{13}$C NMR (CDCl$_3$) δ 220.7, 55.4, 52.5, 51.9, 51.0, 47.6, 46.6, 35.6, 34.8, 34.0, 31.3, 30.5, 30.2, 26.3, 21.5, 21.1, 20.4, 13.7, 13.3.

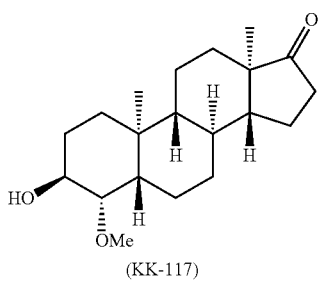

(3β,4α,5β,8α,9β,10α,13α,14β)-3-Hydroxy-4-methoxyandrostan-17-one (4, KK-117)

A drop of concentrated $H_2SO_4$ was added to stirred solution of compound 3 (250 mg, 0.87 mmol) in MeOH (10 mL) and stirring was continued at room temperature for 3 h. The reaction was made alkaline by addition of aqueous NaHCO$_3$ and the MeOH was removed on a rotary evaporator. The resulting residue was diluted with water and extracted into EtOAc (3×75 mL). The combined organic extracts were dried and concentrated to give a solid which was purified by flash column chromatography (silica gel eluted with 35% EtOAc in hexanes) to give product 4 as a white solid (200 mg, 78%): mp 215-218° C.; $[α]_D^{23}$ −99 (c 0.06, CHCl$_3$); IR $v_{max}$ 3510, 2917, 2838, 1735, 1594, 1443, 1375, 1242 cm$^{-1}$; $^1$H NMR (CDCl$_3$) δ 4.02 (br s, 1H), 3.35 (s, 3H), 3.04 (s, 1H), 2.44 (dd, 1H, J=19.0 Hz, 9.0 Hz), 0.98 (s, 3H), 0.86 (s, 3H), 0.62 (m, 1H); $^{13}$C NMR (CDCl$_3$) δ 221.5, 85.4, 66.1, 59.0, 55.2, 51.5, 47.8, 44.0, 36.2, 35.8, 35.0, 31.8, 31.5, 31.1, 25.2, 25.0, 21.7, 19.6, 14.0, 13.8. Anal. (C$_{20}$H$_{32}$O$_3$): C, 74.96%; H, 10.06%. Found: C, 75.13%; H, 9.90%.

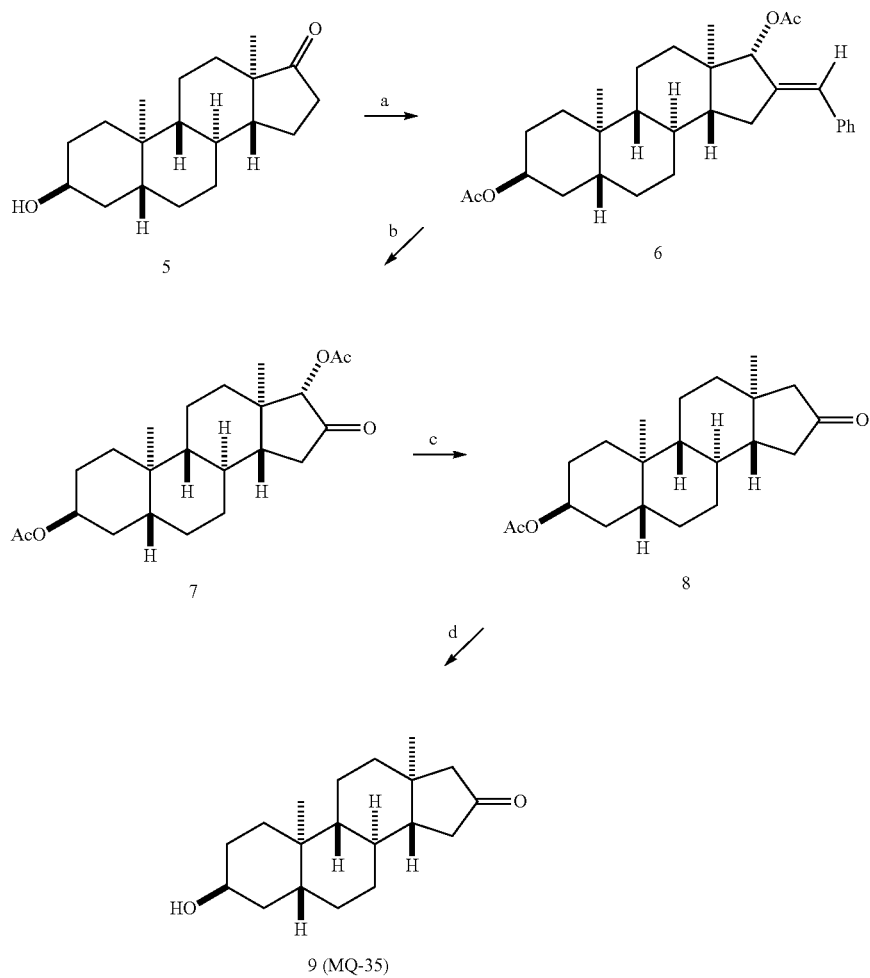

Scheme 2

In accordance with Scheme 2, the following compounds were prepared, using methods generally known in the art and as outlined below.

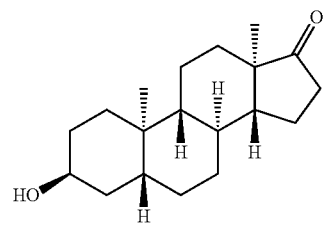

(3β,5β,8α,9β,10α,13α,14β)-3-Hydroxyandrostan-17-one (5)

The compound was prepared as previously described. (Katona, B. W.; Krishnan, K.; Cai, Z. Y.; Manion, B. D.; Benz, A.; Taylor, A.; Evers, A. S.; Zorumski, C. F.; Mennerick, S.; Covey, D. F. Neurosteroid analogues. 12. Potent enhancement of GABA-mediated chloride currents at GABA$_A$ receptors by ent-androgens. *Eur. J. Med. Chem.* 2008, 43, 107-113.)

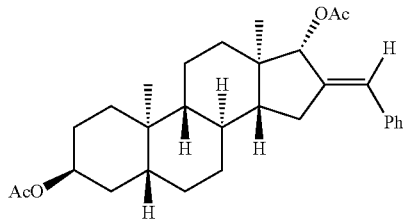

(3β,5β,8α,9β,10α,13α,14α,17α)-16-(Phenylmethylene)-androstane-3,17-diol Diacetate (6)

Compound 5 (1.25 g, 4.5 mmol) and benzaldehyde (1.4 mL, 14 mmol) were added to KOH (700 mg) dissolved in EtOH (60 mL) and the reaction was stirred at room temperature for 16 h. The reaction mixture was cooled to 0° C. and CeCl$_3$.7 H$_2$O (7.45 g, 20 mmol) and NaBH$_4$ (756 mg, 20 mmol) were added, the reaction was allowed to warm to room temperature and stirring continued for 3 h. Glacial AcOH (7 mL) was added and the product extracted into EtOAc (3×150 mL). The combined extracts were dried and the solvents removed to give an oil. The oil was dissolved in CH$_2$Cl$_2$ (30 mL) and AcOAc (1.4 mL, 15 mmol), NEt$_3$ (4.2 ml, 30 mmol) and DMAP (200 mg) were added and stirring was continued at room temperature for 4 h. Aqueous saturated NaHCO$_3$ was then added. After 1 h, the product was extracted into CH$_2$Cl$_2$ (3×125 mL). The combined extracts were dried and solvents removed to give an oil. The crude product was purified by flash column chromatography (silica gel, eluted with 25-35% EtOAc in hexanes) to give product 6 as a colorless liquid containing benzyl acetate. The benzyl acetate was removed by applying high vacuum at 60° C. for 10 h, to give product 6 as a white solid (1.9 g, 91%): mp 162-164° C.; IR ν$_{max}$ 2932, 2855, 1735, 1492, 1447, 1371, 1237 cm$^{-1}$; $^1$H NMR (CHCl$_3$) δ 7.37-7.17 (m, 5H), 6.21 (d, 1H, J=2.4 Hz), 5.37 (s, 1H), 5.03 (s, 1H), 2.68 (dd, 1H, J=16.8 Hz, 6.6 Hz), 2.21 (s, 3H), 2.07 (s, 3H), 0.83 (s, 3H), 0.78 (s, 3H); $^{13}$C NMR (CHCl$_3$) δ 171.2, 170.7, 141.0, 137.6, 128.3 (2×C), 128.2 (2×C), 126.4, 123.5, 84.6, 70.0, 54.1, 48.9, 42.9, 40.0, 36.5, 35.9, 34.8, 32.8, 32.7, 31.5, 30.9, 28.1, 26.0, 21.5, 21.2, 20.3, 12.3, 11.3.

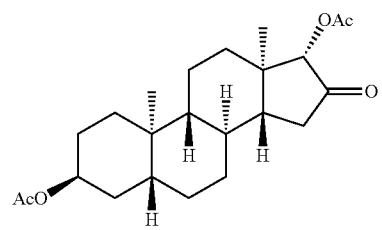

(3β,5β,8α,9β,10α,13α,14β,17α)-3,17-Dihydroxyandrostan-16-one Diacetate (7)

Compound 7 was prepared from compound 5 by a multi-step procedure without isolation of intermediate compound 6. Compound 5 (115 mg, 0.35 mmol) was dissolved in EtOH (20 mL), benzaldehyde (106 mg, 1.2 mmol) and KOH (50 mg) were added at room temperature. After 16 h, the reaction was cooled to 0° C. and CeCl$_3$.7 H$_2$O (740 mg, 2 mmol) and NaBH$_4$ (76 mg, 2 mmol) were added. After stirring for 2 h, aqueous NH$_4$Cl was added and the product extracted into EtOAc (3×50 mL) The combined extracts were dried and the solvents were removed on a rotary evaporator. The residue was dissolved in CH$_2$Cl$_2$ (20 mL). Ac$_2$O (510 mg, 5.0 mmol) Et$_3$N (2.04 g, 10.0 mmol) and DMAP (30 mg) were added and the reaction was stirred at room temperature. After 1 h, water (30 mL) was added and crude product 6 was extracted into CH$_2$Cl$_2$ (3×30 mL). The combined extracts were dried and the solvents removed. The crude product 6 was dissolved in MeOH (40 mL) and EtOAc (20 mL) and cooled to −78° C. Ozone was bubbled through the solution for 30 min and excess ozone was removed with an O$_2$ stream for 30 min. Me$_2$S (5 mL) was added at −78° C. and the reaction was allowed to warm to room temperature. After 14 h, solvents were removed on a rotary evaporator and the residue was purified by flash column chromatography (silica gel, eluted with 20% EtOAc in hexanes) to give compound 7 was a white solid (110 mg, 82%, starting from compound 5) and had: $^1$H NMR (CDCl$_3$) δ 4.96 (m, 2H), 2.11 (s, 3H), 2.01 (s, 3H), 0.77 (s, 6H); $^{13}$C NMR (CDCl$_3$) δ 211.0, 170.5, 170.2, 85.5, 69.7, 53.8, 45.2, 41.6, 39.7, 36.2, 35.9, 35.8, 34.2, 32.6, 32.4, 31.4, 27.8, 25.8, 21.4, 20.5, 19.7, 12.3, 11.2.

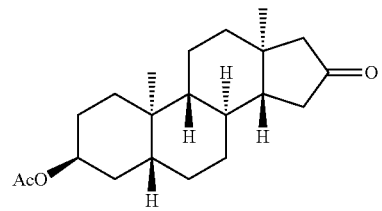

(3β,5β,8α,9β,10α,13α,14β)-3-Hydroxyandrostan-16-one Acetate (8)

Freshly prepared Sm filings (1.5 mmol, 225 mg) were added to THF (10 mL) and $I_2$ (1.0 mmol, 254 mg) in THF (5 mL) was added at room temperature. The suspension was stirred under $N_2$. After 30 min, the mixture became deep blue indicating $SmI_2$ formation and stirring was continued for another 30 min. Compound 7 (0.28 mmol, 110 mg) in THF/methanol (10/1, 11 mL) was added. After 2 h, 10% aqueous $Na_2CO_3$ (60 mL) was added and the product was extracted into EtOAc (3×50 mL). The combined extracts were washed with brine (2×20 mL) and dried. Solvents were removed and the residue was purified by flash column chromatography (silica gel, eluted with 20% EtOAc in hexanes) to give product 8 (48 mg, 51%) and a compound in which the 16-ketone group had been reduced to a 16-hydroxyl group of undetermined configuration (48 mg). Jones oxidation of the 16-hydroxyl group gave additional compound 8 (40 mg, 43%): $^1$H NMR (CDCl$_3$) δ 5.00 (br s, 1H), 2.03 (s, 3H), 0.86 (s, 3H), 0.81 (s, 3H); $^{13}$C NMR (CDCl$_3$) δ 218.7, 170.6, 69.9, 55.8, 54.1, 51.7, 39.9, 39.1, 38.1, 35.9, 34.8, 32.7, 32.5, 32.1, 28.0, 26.0, 21.5, 20.3, 18.0, 11.3.

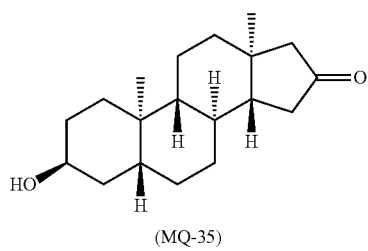

(MQ-35)

(3β,5β,8α,9β,10α,13α,14β)-3-Hydroxyandrostan-16-one (9, MQ-35)

Compound 8 (88 mg, 0.27 mmol) was dissolved in methanol (10 mL) and water (0.5 mL) and $K_2CO_3$ (5 mmol, 680 mg) were added. The reaction was refluxed for 2 h, cooled to room temperature, water (30 mL) was added and the product was extracted into EtOAc (50 mL×3). The combined extracts were dried, filtered, and the solvent removed. The residue was purified by flash column chromatography (silica gel, eluted with 25-40% EtOAc in hexanes) to give product 9 (72 mg, 93%) as a white solid: mp 152-153° C.; $[α]_D^{23}$ +156.8 (c 0.25, CHCl$_3$); IR $ν_{max}$ 3435, 1737 cm$^{-1}$; $^1$H NMR (CDCl$_3$) δ 4.06 (m, 1H), 0.87 (s, 3H), 0.81 (s, 3H); $^{13}$C NMR (CDCl$_3$) δ 219.0, 66.4, 55.9, 54.2, 51.7, 39.3, 39.2, 39.0, 38.2, 36.3, 35.8, 34.9, 32.2, 31.9, 28.9, 28.3, 20.3, 18.1, 11.2. Anal. (C$_{19}$H$_{30}$O$_2$): C, 78.57%; H, 10.41%. found: C, 78.36%; H, 10.58%.

Compounds 25 (KK-97), 26 (KK-102), 27 (KK-103) and 28 (KK-122) were also prepared by the synthetic sequence shown in Scheme 2. Compound 25 was prepared by the following compound sequence: 10→13→17→21→25. Compound 26 was prepared by the following compound sequence: 11→14→18→22→26. Compound 27 was prepared by the following compound sequence: 12→15→19→23→27. Compound 28 was prepared by the following compound sequence: 4→16→20→24→28.

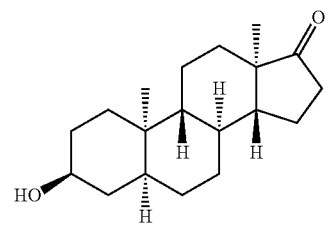

(3β,5α,8α,9β,10α,13α,14β)-3-Hydroxyandrostan-17-one (10)

The 5α-reduced compound 10 was prepared from ent-testosterone as previously described. (Katona, B. W.; Krishnan, K.; Cai, Z. Y.; Manion, B. D.; Benz, A.; Taylor, A.; Evers, A. S.; Zorumski, C. F.; Mennerick, S.; Covey, D. F. Neurosteroid analogues. 12. Potent enhancement of GABA-mediated chloride currents at GABA$_A$ receptors by ent-androgens. Eur. J. Med. Chem. 2008, 43, 107-113.)

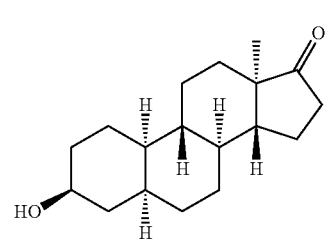

(3β,5α,8α,9β,10α,13α,14β)-3-Hydroxyestran-17-one (11)

The 5α-reduced compound 11 was prepared from the known compound (8α,9β,10α,13α,14β,17α)-17-hydroxyestr-4-en-3-one (Green, P. S.; Yang, S. H.; Nilsson, K. R.; Kumar, A. S.; Covey, D. F.; Simpkins, J. W. The nonfeminizing enantiomer of 17β-estradiol exerts protective effects in neuronal cultures and a rat model of cerebral ischemia. Endocrinology 2001, 142, 400-406.) using the methods reported previously for the preparation of 5α-reduced compound 10 from ent-testosterone. (Katona, B. W.; Krishnan, K.; Cai, Z. Y.; Manion, B. D.; Benz, A.; Taylor, A.; Evers, A. S.; Zorumski, C. F.; Mennerick, S.; Covey, D. F. Neurosteroid analogues. 12. Potent enhancement of GABA-mediated chloride currents at GABA$_A$ receptors by ent-androgens. Eur. J. Med. Chem. 2008, 43, 107-113.) Compound 11 was a white solid and had: mp 161-163° C.; $[α]_D^{23}$ −117.4 (c 0.55, CHCl$_3$); IR $ν_{max}$ 3401, 2924, 2859, 1738, 1453, 1375 cm$^{-1}$; $^1$H NMR (CDCl$_3$) δ 3.64 (m, 1H), 0.87 (s, 3H); $^{13}$C NMR (CDCl$_3$) δ 221.5, 71.5, 50.5, 47.9, 41.2, 39.9, 38.6, 36.3, 35.9, 35.6, 31.6, 31.3, 29.6, 25.9, 25.0, 24.9, 21.6, 13.8. Anal. (C$_{18}$H$_{28}$O$_2$): C, 78.21%; H, 10.21%. Found: C, 78.12%; H, 9.98%.

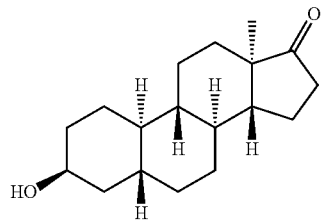

(3β,5β,8α,9β,10α,13α,14β)-3-Hydroxyestran-17-one (12, KK-18)

The 5β-reduced compound 12 was prepared from the known compound (8α,9β,10α,13α,14β,17α)-17-hydroxyestr-4-en-3-one (Green, P. S.; Yang, S. H.; Nilsson, K. R.; Kumar, A. S.; Covey, D. F.; Simpkins, J. W. The nonfeminizing enantiomer of 17β-estradiol exerts protective effects in neuronal cultures and a rat model of cerebral ischemia. *Endocrinology* 2001, 142, 400-406.) using the methods reported previously for the preparation of 5β-reduced compound 5 from ent-testosterone. (Katona, B. W.; Krishnan, K.; Cai, Z. Y.; Manion, B. D.; Benz, A.; Taylor, A.; Evers, A. S.; Zorumski, C. F.; Mennerick, S.; Covey, D. F. Neurosteroid analogues. 12. Potent enhancement of GABA-mediated chloride currents at GABA$_A$ receptors by ent-androgens. *Eur. J. Med. Chem.* 2008, 43, 107-113.) Compound 12 was a white solid and had: mp 158-160° C.; [α]$_D^{23}$ −108.5 (c 0.24 CHCl$_3$); IR ν$_{max}$ 3517, 2913, 2948, 2859, 1721, 1662, 1445, 1379, 1337, 1300, 1268 cm$^{-1}$; $^1$H NMR (CDCl$_3$) δ 4.10 (br s, 1H), 0.88 (s, 3H); $^{13}$C NMR (CDCl$_3$) δ 221.7, 66.3 50.6, 48.2, 47.9, 47.0, 40.7, 40.5, 35.9, 35.8, 33.3, 32.9, 31.5, 29.8, 24.9, 23.7, 21.6, 13.8. HRMS (FAB) m/z Calcd for C$_{18}$H$_{28}$O$_2$Na: 299.1987. Found, 299.1989.

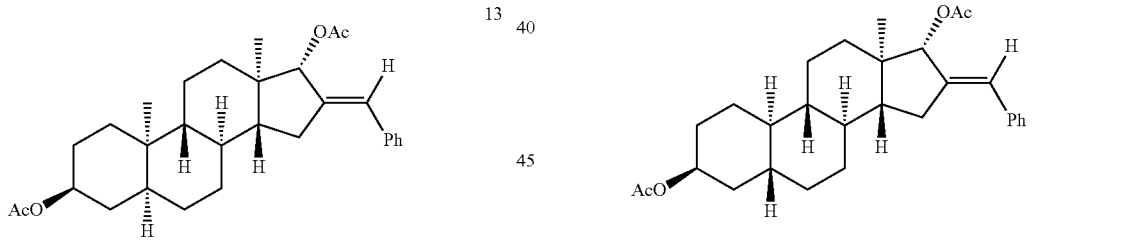

(3β,5α,8α,9β,10α,13α,14β)-16-(Phenylmethylene)-androstane-3,17-diol Diacetate (13)

Compound 13 was prepared as a white solid (205 mg, 92%) from ent-etiocholanolone (10) (Katona, B. W.; Krishnan, K.; Cai, Z. Y.; Manion, B. D.; Benz, A.; Taylor, A.; Evers, A. S.; Zorumski, C. F.; Mennerick, S.; Covey, D. F. Neurosteroid analogues. 12. Potent enhancement of GABA-mediated chloride currents at GABA$_A$ receptors by ent-androgens. *Eur. J. Med. Chem.* 2008, 43, 107-113.) using the procedure described for the preparation of compound 6. Compound 13 had: mp 96-99° C.; IR ν$_{max}$ 3032, 2866, 2935, 1738, 1493, 1449, 1380, 1363, 1241 cm$^{-1}$; $^1$H NMR (CDCl$_3$) δ 7.37-7.18 (m, 5H), 6.21 (bs, 1H), 5.38 (s, 1H), 4.74 (m, 1H), 2.67 (dd, 1H, J=13 Hz, 7 Hz), 2.21 (s, 3H), 2.04 (s, 3H), 0.96 (s, 3H), 0.77 (s, 3H); $^{13}$C NMR (CDCl$_3$) δ 171.2, 170.7, 141.0, 137.6, 128.3, 128.2, 126.5, 123.6, 84.5, 74.2, 48.9, 43.0, 41.8, 40.5, 36.6, 35.2, 35.0, 34.7, 32.2, 30.9, 26.8, 26.6, 26.0, 23.3, 21.4, 21.2, 20.3, 12.2. Anal. (C$_{30}$H$_{40}$O$_4$): C, 77.55%; H, 8.68%. Found: C, 77.60%; H, 8.36%.

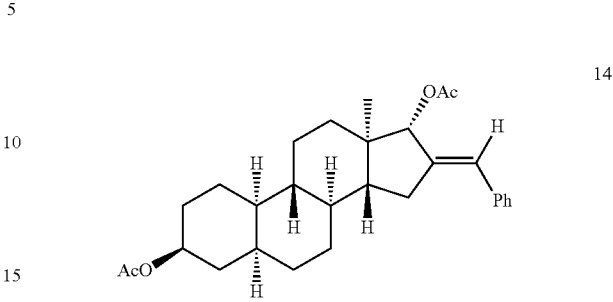

(3β,5α,8α,9β,10α,13α,14β,17α)-19-Nor-16-(phenylmethylene)-androstane-3,17-diol Diacetate (14)

Compound 14 was prepared as a white solid (700 mg, 74%) from ent-19-noretiocholanolone (11) using the procedure described for the preparation of compound 6. Compound 14 had: mp 133-135° C.; IR ν$_{max}$ 2920, 2870, 1737, 1736, 1448, 1370, 1239 cm$^{-1}$; $^1$H NMR (CDCl$_3$) δ 7.40-7.18 (m, 5H), 6.21 (d, 1H, J=2.5 Hz), 5.39 (s, 1H), 4.75 (m, 1H), 2.67 (dd, 1H, J=16.4 Hz, 7.0 Hz), 2.21 (s, 3H), 2.04 (s, 3H), 0.78 (s, 3H); $^{13}$C NMR (CDCl$_3$) δ 171.14, 170.61, 140.90, 137.55, 128.26, 128.23, 126.45, 123.57, 84.61, 74.07, 47.90, 43.09, 41.03, 39.78, 38.37, 36.47, 35.35, 32.24, 31.18, 30.78, 25.74, 25.68, 25.07, 21.43, 21.16, 12.20. Anal. (C$_{28}$H$_{38}$O$_4$): C, 77.30%; H, 8.57%. Found: C, 77.19%; H, 8.53%.

(3β,5β,8α,9β,10α,13α,14α,17α)-19-Nor-16-(phenylmethylene)-androstane-3,17-diol Diacetate (15)

Compound 15 (670 mg, 91%) was prepared as an oil from compound ent-19-norandrosterone (12) using the procedure described for the preparation of compound 6. Compound 12 had: IR ν$_{max}$ 2919, 2862, 1738, 1600, 1492, 1446, 1370, 1240 cm$^{-1}$; $^1$H NMR (CDCl$_3$) δ 7.40-7.10 (m, 5H), 6.24 (b s, 1H), 5.40 (b s 1H), 5.07 (b s, 1H), 2.69 (dd, 1H, J=16.7 Hz, 6.3 Hz), 2.23 (s, 3H), 2.07 (s, 3H), 0.81 (s, 3H); $^{13}$C (CDCl$_3$) NMR δ 171.0, 170.6, 140.9, 137.5, 128.2 (4×C), 126.4, 123.5, 84.5, 69.7, 48.0, 47.8, 46.5, 42.9, 40.4, 37.4, 36.6, 36.4, 33.2, 30.7, 30.4, 29.9, 25.0, 24.2, 21.4, 21.1, 12.1. Anal. (C$_{29}$H$_{38}$O$_4$): C, 77.30%; H, 8.50%. Found: C, 77.55%; H, 8.26%.

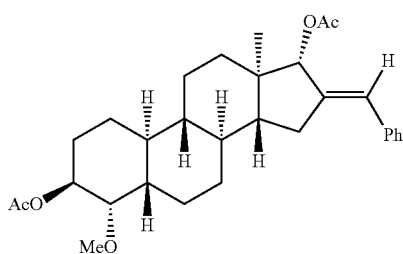

(3β,4α,5β,8α,9β,10α,13α,14β)-4-Methoxy-16-(phenylmethylene)-androstane-3,17-diol Diacetate (16)

Compound 16 (300 mg, 97%) was prepared as a white solid from compound 4 using the procedure described for the preparation of compound 6. Compound 13 had: mp 150-152° C.; IR $v_{max}$ 2935, 2859, 1738, 1599, 1492, 1448, 1371, 1241 cm$^{-1}$; $^1$H NMR (CDCl$_3$) δ 7.30-7.08 (m, 5H), 6.13 (d, 1H, J=2.2 Hz), 5.28 (s, 1H), 4.97 (d, 1H, J=2.3 Hz), 3.30 (s, 3H), 3.22 (s, 1H), 2.60 (m, 1H), 2.12 (s, 3H), 2.00 (s, 3H), 0.90 (s, 3H), 0.69 (s, 3H); $^{13}$C NMR (CDCl$_3$) δ 171.2, 170.4, 141.0, 137.6, 128.3 (2×C), 128.2 (2×C), 126.4, 123.5, 84.6, 82.5, 68.6, 58.9, 55.0, 49.0, 45.0, 42.9, 36.4, 35.9, 34.8, 32.5, 31.8, 30.9, 25.0, 22.0, 21.4, 21.2, 19.9, 14.0, 12.3.

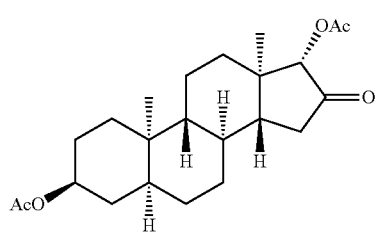

(3β,5α,8α,9β,10α,13α,14β,17α)-3,17-Dihydroxyandrostan-16-one Diacetate (17)

Compound 17 was prepared as a white solid (148 mg, 90%) from compound 13 using the ozonolysis reaction described within the multi-step procedure for the preparation of compound 7. Compound 17 had: mp 164-166° C.; IR $v_{max}$ 2937, 2868, 1762, 1739, 1451, 1365, 1240 cm$^{-1}$; $^1$H NMR (CDCl$_3$) δ 5.30 (s, 1H), 5.02 (m, 1H), 2.40-0.90 (m), 2.17 (s, 3H), 2.04 (s, 3H), 0.97 (s, 3H), 0.82 (s, 3H); $^{13}$C NMR (CDCl$_3$) δ 211.0, 170.6, 170.3, 85.6, 73.9, 45.3, 41.7, 41.5, 40.4, 36.4, 36.0, 34.7, 34.6, 32.1, 26.5, 26.1, 23.1, 21.4, 20.6, 19.8, 12.3. HRMS (FAB) m/z Calcd for C$_{23}$H$_{34}$O$_5$Na: 413.2304. Found: 413.2309.

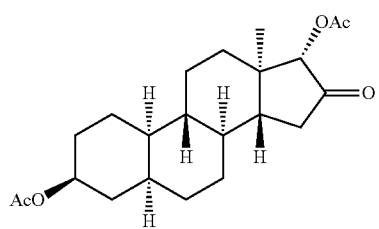

(3β,5α,8α,9β,10α,13α,14β,17α)-19-Nor-3,17-dihydroxyandrostan-16-one Diacetate (18)

Compound 18 was prepared as a white solid (540 mg, 95%) from compound 14 using the ozonolysis reaction described within the multi-step procedure for the preparation of compound 7. Compound 18 had: mp 144-146° C.; IR $v_{max}$ 2922, 2868, 1761, 1742, 1454, 1371, 1239 cm$^{-1}$; $^1$H NMR (CDCl$_3$) δ 4.94 (s, 1H), 4.65 (m), 2.23 (dd, 1H, J=18.4 Hz, 7.4 Hz), 2.08 (s, 3H), 1.94 (s, 3H), 0.75 (s, 3H); $^{13}$C NMR (CDCl$_3$) δ 210.6, 170.2, 170.0, 85.5, 73.6, 44.1, 41.6, 40.1, 39.5, 38.5, 36.0, 35.7, 35.0, 31.9, 30.8, 25.6, 25.4, 25.2, 24.4, 21.1, 20.4, 12.1. Anal. (C$_{22}$H$_{32}$O$_5$): C, 70.18%; H, 8.57%. Found: C, 70.44%; H, 8.57%.

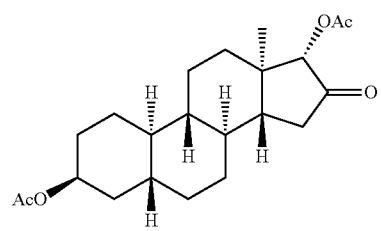

(3β,5β,8α,9β,10α,13α,14β,17α)-19-Nor-3,17-dihydroxyandrostan-16-one Diacetate (19)

Compound 19 (530 mg, 98%) was prepared as a white solid from compound 15 using the ozonolysis reaction described within the multi-step procedure for the preparation of compound 7. Compound 19 had: mp 116-118° C.; IR $v_{max}$ 2919, 2861, 1763, 1736, 1445, 1371, 1239, 1216 cm$^{-1}$; $^1$H NMR (CDCl$_3$) δ 4.91 (br s, 1H), 4.89 (s, 1H), 2.19 (dd, 1H, J=18.7 Hz, 7.7 Hz), 2.03 (s, 3H), 1.92 (s, 3H), 0.71 (s, 3H); $^{13}$C NMR (CDCl$_3$) δ 210.6, 170.1, 169.9, 85.4, 69.3, 47.4, 46.1, 44.1, 41.5, 39.5, 37.1, 36.2, 35.9, 35.6, 32.8, 30.3, 29.6, 24.3, 23.7, 21.1, 20.3, 12.0. Anal. (C$_{22}$H$_{32}$O$_5$): C, 70.18%; H, 8.57%. Found: C, 70.30%; H, 8.59%.

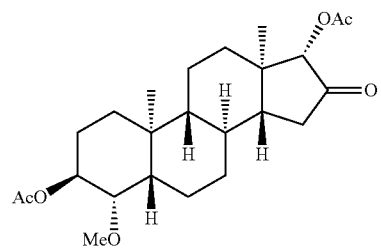

(3β,4α,5β,8α,9β,10α,13α,14β,17α)-3,17-Dihydroxy-4-methoxyandrostan-16-one Diacetate (20)

Compound 20 (205 mg, 87%) was prepared as a white solid from compound 16 using the ozonolysis reaction described within the multi-step procedure for the preparation of compound 7. Compound 20 had: mp 158-160° C.; IR $v_{max}$ 2928, 1762, 1742, 1449, 1372, 1240 cm$^{-1}$; $^1$H NMR (CDCl$_3$) δ 5.02 (d, 1H, J=2.0 Hz), 4.97 (s, 1H), 3.34 (s, 3H), 3.01 (br s, 1H), 2.13 (s, 3H), 2.05 (s, 3H), 0.96 (s, 3H), 0.79 (s, 3H); $^{13}$C NMR (CDCl$_3$) δ 211.0, 170.3 (2×C), 85.6, 82.2, 68.5, 58.8, 54.8, 45.3, 44.8, 41.6, 36.2, 36.0, 35.8, 34.3, 32.3, 31.8, 24.8, 21.9, 21.3, 20.6, 19.4, 13.9, 12.4.

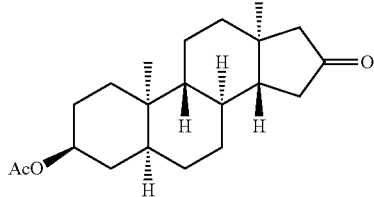

21

(3β,5α,8α,9β,10α,13α,14β)-3-Hydroxyandrostan-16-one Acetate (21)

Compound 21 was prepared as a colorless liquid (100 mg, 83%) from compound 17 using the procedure described for the preparation of compound 8. Compound 21 had: IR $v_{max}$ 2867, 2932, 1739, 1451, 1408, 1382, 1363, 1243 cm$^{-1}$; $^1$H NMR (CDCl$_3$) δ 4.72 (m, 1H), 2.02 (s, 3H), 0.96 (s, 3H), 0.86 (s, 3H); $^{13}$C NMR (CDCl$_3$) δ 218.6, 170.6, 74.0, 55.9, 51.7, 41.6, 40.5, 39.2, 39.2, 38.3, 35.2, 34.7, 32.1, 26.5, 23.2, 21.4, 20.3, 18.0. Anal. (C$_{21}$H$_{32}$O$_3$): C, 75.86%; H, 9.70%. Found: C, 75.75%; H, 9.74%.

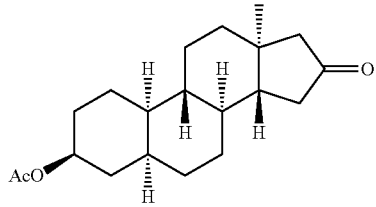

22

(3β,5α,8α,9β,10α,13α,14β)-19-Nor-3-hydroxyandrostan-16-one Acetate (22)

Compound 22 was prepared as a white amorphous solid (380 mg, 97%) from compound 118 using the procedure described for the preparation of compound 8. Compound 22 had: mp 107-110° C.; IR $v_{max}$ 2919, 2869, 1744, 1454, 1408, 1366, 1243 cm$^{-1}$; $^1$H NMR (CDCl$_3$) δ 4.69 (m, 1H), 1.98 (s, 3H), 0.84 (s, 3H); $^{13}$C NMR (CDCl$_3$) δ 218.1, 170.3, 73.8, 55.9, 50.7, 40.9, 39.7, 39.1, 38.9, 38.1, 35.1, 32.1, 31.1, 31.0, 26.3, 25.6, 25.3, 25.0, 21.2, 18.0. HRMS (FAB) m/z Calcd for C$_{20}$H$_{31}$O$_3$: 319.2273. Found: 319.2272.

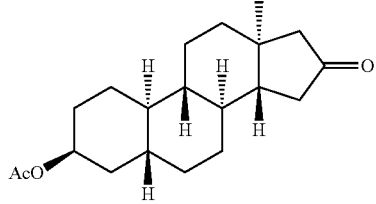

23

(3β,5β,8α,9β,10α,13α,14β)-19-Nor-3-hydroxyandrostan-16-one Acetate (23)

Compound 23 (290 mg, 70%) was prepared as a colorless oil from compound 19 using the procedure described for the preparation of compound 8. Compound 23 had: IR $v_{max}$ 2918, 2862, 1737, 1444, 1408, 1378, 1244, 1214 cm$^{-1}$; $^1$H NMR (CDCl$_3$) δ 4.97 (b s, 1H), 1.97 (s, 3H), 0.82 (s, 3H); $^{13}$C NMR (CDCl$_3$) δ 218.1, 170.3, 69.6, 55.8, 50.8, 47.8, 46.5, 40.4, 39.0, 38.9, 38.0, 37.3, 36.5, 36.5, 33.1, 31.0, 29.8, 25.0, 23.3, 21.2, 17.9. Anal. (C$_{20}$H$_{30}$O$_3$): C, 75.43%; H, 9.50%. Found: C, 75.17%; H, 9.39%.

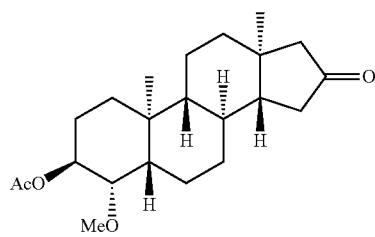

24

(3β,4α,5β,8α,9β,10α,13α,14β)-3-Hydroxy-4-Methoxyandrostan-16-one Acetate (24)

Compound 24 (72 mg, 84%) was prepared as a white solid from compound 20 using the procedure described for the preparation of compound 8. Compound 24 had: mp 159-161° C.; IR $v_{max}$ 2944, 2861, 1733, 1449, 1407, 1380, 1244, 1216 cm$^{-1}$; $^1$H NMR (CDCl$_3$) δ 5.03 (d, 1H, J=1.6 Hz), 3.36 (s, 3H), 3.03 (br s, 1H), 2.07 (s, 3H), 0.98 (s, 3H), 0.87 (s, 3H); $^{13}$C NMR (CDCl$_3$) δ 218.8, 170.4, 82.4, 68.6, 58.9, 55.8, 55.0, 51.8, 44.9, 39.3, 39.1, 38.1, 35.9, 34.9, 32.4, 32.4, 24.9, 22.0, 21.4, 19.9, 18.1, 14.0.

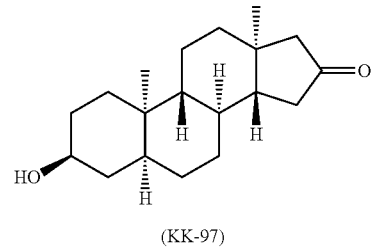

25
(KK-97)

(3β,5α,8α,9β,10α,13α,14β)-3-Hydroxyandrostan-16-one (25, KK-97)

Compound 25 was prepared from compound 21 using the procedure described for the preparation of compound 9. Flash column chromatography (silica gel, eluted with 25-40% EtOAc in hexanes) gave product 25 as a white solid (70 mg, 89%): mp 132-134° C.; [α]$_D^{23}$ +177.44 (c 0.1, CHCl$_3$); IR $v_{max}$ 3401, 2928, 2860, 1743, 1450, 1380 cm$^{-1}$; $^1$H NMR (CDCl$_3$) δ 3.63 (1H, m), 0.95 (s, 3H), 0.94 (s, 3H); $^{13}$C NMR (CDCl$_3$) δ 218.9, 71.5, 55.9, 51.7, 41.8, 40.5, 39.3, 39.2, 38.3, 36.3, 35.2, 35.0, 34.7, 30.4, 26.9, 26.7, 23.2, 20.3, 18.0. HRMS (EI) m/z Calcd for C$_{19}$H$_{21}$O$_2$: 291.2324. Found: 291.2323.

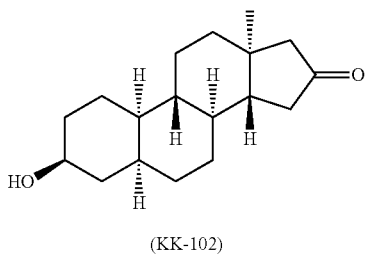

(KK-102)

(3β,5α,8α,9β,10α,13α,14β)-19-Norandrostan-16-one (26, KK-102)

Compound 26 was prepared from compound 22 using the procedure described for the preparation of compound 9. Flash column chromatography (silica gel, eluted with 25-40% EtOAc in hexanes) gave product 26 as a white solid (276 mg, 89%): mp 139-142° C.; $[\alpha]_D^{23}$ +160 (c 0.1, CHCl$_3$); IR $\nu_{max}$ 3401, 2922, 2859, 1744, 1453, 1407, 1280 cm$^{-1}$; $^1$H NMR (CDCl$_3$) δ 3.57 (m, 1H), 2.53 (bs 1H, OH), 0.81 (s, 3H); $^{13}$C NMR (CDCl$_3$) δ 218.7, 71.1, 55.9, 50.6, 40.9, 39.8, 39.1, 38.9, 38.4, 38.0, 36.1, 35.2, 31.1, 29.3, 26.4, 25.5, 24.9, 17.9. Anal. (C$_{18}$H$_{28}$O$_2$): C, 78.21%; H, 10.21%. Found: C, 78.06%; H, 10.11%.

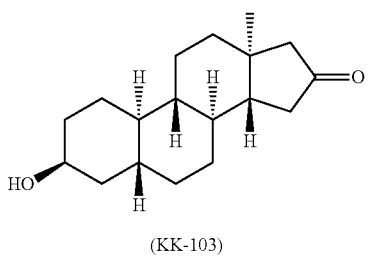

(KK-103)

(3β,5β,8α,9β,10α,13α,14β)-19-Norandrostan-16-one (27, KK-103)

Compound 24 (207 mg, 98%) was prepared from compound 23 using the procedure described for the preparation of compound 9. Flash column chromatography (silica gel, eluted with 25-40% EtOAc in hexanes) gave product 27 as a white solid: mp 160-162° C.; $[\alpha]_D^{23}$ +162.0 (c 0.22, CHCl$_3$); IR $\nu_{max}$ 3401, 2915, 2861, 1743 cm$^{-1}$; $^1$H NMR (CDCl$_3$) δ 4.08 (br s, 1H), 0.87 (s, 3H); $^{13}$C NMR (CDCl$_3$) δ 218.8, 66.3, 56.0, 50.9, 48.0, 47.0, 40.53, 40.47, 39.2, 39.1, 38.1, 35.8, 33.4, 32.9, 31.2, 25.1, 23.4, 18.1. Anal. (C$_{18}$H$_{28}$O$_2$): C, 78.21%; H, 10.21%. Found: C, 78.40%; H, 10.15%.

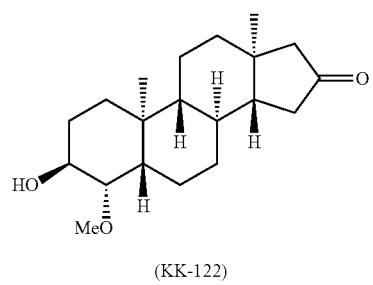

(KK-122)

(3β,4α,5β,8α,9β,10α,3α,14β)-3-Hydroxy-4-methoxyandrostan-16-one (28, KK-122)

Compound 28 (50 mg, 94%) was prepared from compound 24 using the procedure described for the preparation of compound 9. Flash column chromatography (silica gel, eluted with 25-40% EtOAc in hexanes) gave product 24 as a white solid: mp 198-200° C.; $[\alpha]_D^{23}$ +152 (c 0.2, CHCl$_3$); IR $\nu_{max}$ 3458, 1725 cm$^{-1}$; $^1$H NMR (CDCl$_3$) δ 4.01 (br s, 1H), 3.34 (s, 3H), 3.02 (d, 1H, J=1.1 Hz), 0.98 (s, 3H), 0.87 (s, 3H); $^{13}$C NMR δ 219.0, 85.4, 66.2, 59.0, 55.9, 55.1, 51.8, 43.9, 39.3, 39.3, 38.1, 36.2, 34.9, 32.6, 31.6, 25.2, 25.0, 19.9, 18.1, 14.0. Anal. (C$_{20}$H$_{32}$O$_3$): C, 74.96%; H, 10.06%. Found: C, 75.07%; H, 9.96%.

Scheme 3

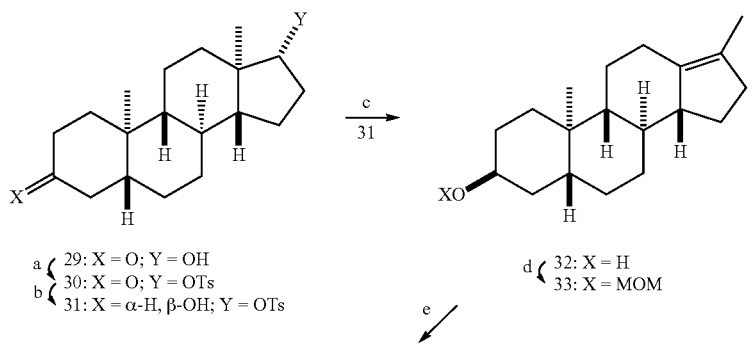

a ( 29: X = O; Y = OH
b ( 30: X = O; Y = OTs
  ( 31: X = α-H, β-OH; Y = OTs d ( 32: X = H
  ( 33: X = MOM e

-continued

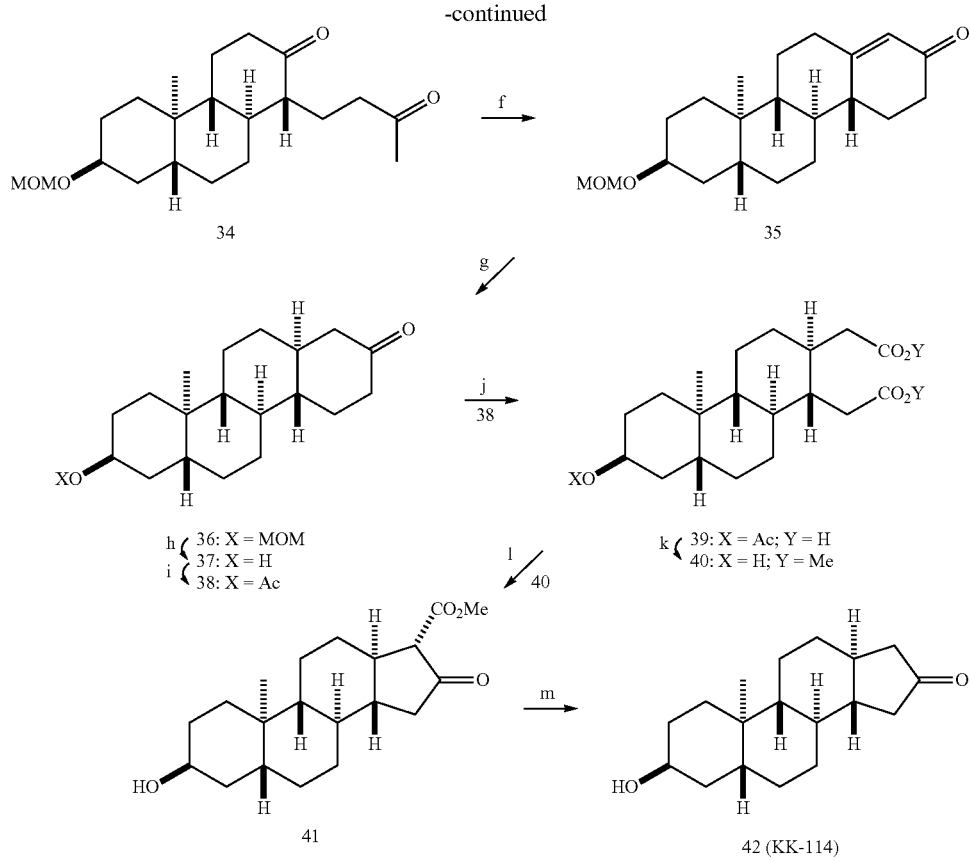

In accordance with Scheme 3, the following compounds were prepared, using methods generally known in the art and as outlined below.

(5β,8α,9β,10α,13α,14β,17α)-17-Hydroxyandrostan-3-one (29)

This compound was prepared as previously described. (Hu, Y. F.; Wittmer, L. L.; Kalkbrenner, M.; Evers, A. S.; Zorumski, C. F.; Covey, D. F. Neurosteroid analogues. Part 5. Enantiomers of neuroactive steroids and benz[e]indenes: total synthesis, electrophysiological effects on $GABA_A$ receptor function and anesthetic actions in tadpoles. *J. Chem. Soc. Perkin Trans.* 1 1997, 3665-3671.)

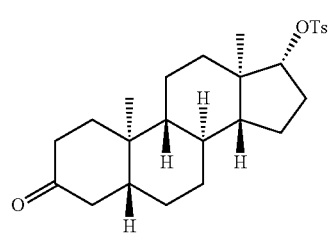

(5β,8α,9β,10α,13α,14β,17α)-17-[[(4-Phenylmethyl)sulfonyl]oxy]-androstan-3-one (30)

Compound 29 (1.8 g, 6.54 mmol), p-TsCl (2.5 g, 13.08 mmol) and pyridine (60 mL) were heated at 40° C. for 18 h. The reaction mixture was cooled and poured into a beaker containing crushed ice. The mixture was extracted with $CH_2Cl_2$ (3×100 mL) and the combined extracts were washed with 1N HCl to remove the pyridine, washed with brine, dried and solvent removed. The crude product was purified by flash column chromatography (silica gel, eluted with 10% EtOAc in $CH_2Cl_2$) to give product 30 as a white crystalline solid (2.65 g, 91%). mp 180-182° C.; IR $v_{max}$ 2917, 2851, 1710, 1598, 1449, 1415, 1361, 1253, 1217 cm$^{-1}$; $^1$H NMR (CDCl$_3$) δ 7.77 (d, 2H, J=7.8 Hz), 7.32 (d, 2H, J=7.8 Hz), 4.24 (t, 1H, J=8.2 Hz), 2.44 (s, 3H), 0.98 (s, 3H), 0.80 (s, 3H); $^{13}$C NMR (CDCl$_3$) δ 211.7, 144.4, 134.1, 129.6 (2×C), 127.76 (2×C), 89.8, 53.5, 49.7, 46.5, 44.5, 43.0, 38.4, 38.0, 36.0, 35.6, 35.0, 31.0, 28.6, 27.6, 23.2, 21.6, 21.6, 20.7, 11.8. 11.4.

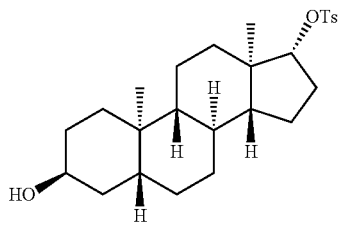

(3β,5β,8α,9β,10α,13α,14β,17α)-17-[[(4-Phenylmethyl)sulfonyl]oxy]-androstan-3-ol (31)

Compound 30 (2.8 g, 6.3 mmol) was dissolved in THF (50 mL), cooled to −78° C. and K-selectride in THF (1 M, 7.2 mL, 7.2 mmol, 1.2 eq) was added dropwise. Stirring at −78° C. was continued for 2 h. Aqueous NaOH (3 M, 20 mL) and then 30% $H_2O_2$ (20 mL) were added and the reaction was warmed to room temperature and stirred for 2 h. Water (150 mL) was added and the product was extracted into EtOAc. The combined EtOAc extracts were dried and the solvents removed to give an oil which was purified by flash column chromatography (silica gel, eluted with 10% EtOAc in $CH_2Cl_2$) to give product 31 (2 g, 71%): mp 186-188° C.; IR $v_{max}$ 3400, 2918, 2850, 1599, 1446, 1355 cm$^{-1}$; $^1$H NMR (CDCl$_3$) δ 7.77 (d, 2H, J=7.1 Hz), 7.32 (d, 2H, J=7.1 Hz), 4.24 (t, 1H, J=7.8 Hz), 4.03 (d, 1H, J=2.3 Hz) 2.44 (s, 3H), 0.78 (s, 3H), 0.75 (s, 3H); $^{13}$C NMR (CDCl$_3$) δ 144.1, 134.2, 129.6 (2×C), 127.8 (2×C), 90.1, 66.4, 66.3, 54.1, 50.0, 43.0, 39.0, 36.1, 35.7, 35.1, 32.1, 31.3, 28.9, 28.2, 27.6, 23.2, 21.6, 20.0, 11.8, 11.1.

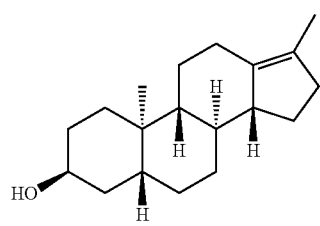

(3β,5β,8α,9β,10α,14β)-17-Methylandrost-14(17)-en-3-ol (32)

MeMgBr (3 M in $Et_2O$, 5 mL) was added to refluxing toluene (80 mL) containing dissolved compound 31 (1.34 g, 3 mmol) and refluxing was continued for 1 h under $N_2$. The reaction was cooled, acidified with 1N HCl and extracted with $CH_2Cl_2$. The combined extracts were washed with brine, dried and concentrated to give an oil. The oil was dissolved in MeOH (20 mL) and 5 M HCl (prepared from concentrated HCl diluted with MeOH) was added and the reaction was stirred at room temperature for 15 h. The reaction was made basic by the addition of aqueous NaHCO$_3$ and the MeOH was removed. The aqueous residue was diluted further with water and the product extracted into EtOAc. The combined extracts were dried and concentrated to give an oil, which was purified by flash column chromatography (silica gel, eluted with 15-35% EtOAc in hexanes) to give product 32 as a colorless oil (750 mg, 91%): IR $v_{max}$ 3337, 2920, 2856, 1444, 1359, 1255 cm$^{-1}$; $^1$H NMR (CDCl$_3$) δ 4.02 (br s, 1H), 1.58 (s, 3H), 0.68 (s, 3H); $^{13}$C NMR (CDCl$_3$) δ 136.5, 127.4, 66.4, 53.9, 52.3, 45.3, 38.7, 37.1, 36.1, 35.8, 32.3, 32.2, 28.9, 28.3, 28.1, 25.6, 25.2, 13.4, 11.1.

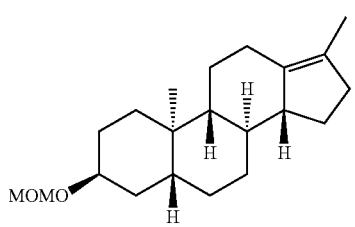

(3β,5β,8α,9β,10α,14β)-3-(Methoxymethoxy)-17-methylandrost-14(17)-ene (33)

Compound 32 (823 mg, 3 mmol) was dissolved $CH_2Cl_2$ (80 mL) and cooled to 0° C. (i-Pr)$_2$EtN (2.6 mL, 15 mmol) and ClCH$_2$OMe (0.76 ml, 10 mmol) were added and the reaction was stirred at room temperature for 6 h. The reaction mixture was made basic by adding aqueous NaHCO$_3$ solution and the product extracted into $CH_2Cl_2$. The combined extracts were washed with brine, dried and solvent removed to give a viscous liquid. The crude product was purified by flash column chromatography (silica gel, eluted with 10-15% EtOAc in hexanes) to give product 33 as a colorless liquid (960 mg, 90%): IR $v_{max}$ 2924, 2857, 1445, 1368, 1302, 1213 cm$^{-1}$; $^1$H NMR (CDCl$_3$) δ 4.57 (s, 2H), 3.75 (s, 1H), 3.28 (s, 3H), 1.51 (s, 3H), 0.64 (s, 3H); $^{13}$C NMR (CDCl$_3$) δ 136.4, 127.1, 94.3, 71.4, 54.8, 53.8, 52.2, 45.3, 39.2, 37.0, 35.8, 33.5, 32.8, 32.2, 28.3, 28.0, 26.2, 25.6, 25.2, 13.2, 11.2.

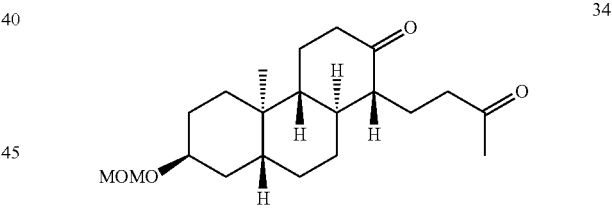

(1R,4aR,4bR,7S,8aR,10aS)-7-(Methoxymethoxy) docecahydro-4b-methyl-1(3-oxobutyl-2(1H)-phenanthrenone (34)

Compound 33 (2.38 g, 7.5 mmol) was dissolved in $CH_2Cl_2$ (100 mL) and cooled to −78° C. $O_3$ was passed through the solution until it remained blue for 20 min and then $O_2$ was passed through the solution until it became colorless. The reaction was warmed to 0° C., AcOH (30 mL) was added and the $CH_2Cl_2$ removed on a rotary evaporator. Additional AcOH (15 mL) and Zn dust (6 g) were added and the reaction was stirred at room temperature for 3 h to decompose the ozonide intermediate. The Zn was removed by filtration through Celite and the Celite was washed with EtOAc. The combined filtrate and washings were combined and the volatile solvents removed to leave the product in AcOH. The AcOH was carefully neutralized with aqueous NaHCO$_3$ and the product extracted into EtOAc. The combined extracts were dried and solvent removed to leave the crude product as an oil which was purified by flash column chromatography (silica gel, eluted with 20-35% EtOAc in hexanes) to give product 34 (1.7 g, 65%) as a liquid: IR $v_{max}$ 2928, 1712, 1447, 1367, 1213 cm$^{-1}$; $^1$H NMR (CDCl$_3$) δ 4.57 (s, 2H), 3.75 (s, 1H), 3.28 (s, 3H), 2.03 (s, 3H), 0.65 (s, 3H); $^{13}$C NMR (CDCl$_3$) δ 212.2, 208.7, 94.3, 71.2, 54.9, 54.6, 52.1, 42.3, 41.7, 40.8, 38.7, 36.0, 33.0, 32.6, 32.0, 29.6, 28.0, 26.2, 26.1, 19.2, 10.9.

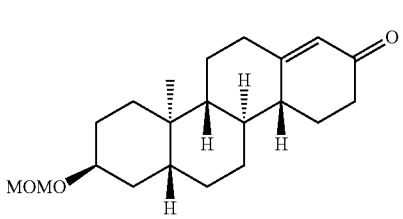

(3β,5β,8α,9β,10α,14β)-3-(Methoxymethoxy)-D-Homo-18-norandrost-13(17a)-en-17-one Acetate (35)

Compound 34 (1.55 g, 4.43 mmol) was dissolved in MeOH (15 mL) and water (1.5 mL), 10% methanolic NaOH (12 mL) was added and the reaction was stirred at room temperature for 1 h. The reaction was then acidified with 3N HCl and the product extracted into CH$_2$Cl$_2$. The combined extracts were washed with aq. NaHCO$_3$, brine, dried and the solvents were removed. The crude product was purified by flash column chromatography (silica gel, eluted with 30-40% ethyl acetate in hexanes) to give product 35 as a white solid. (1.10 g, 75%): mp 98-100° C.; IR $v_{max}$ 2926, 1674, 1622, 1449, 1364, 1259, 1209 cm$^{-1}$; $^1$H NMR (CDCl$_3$) δ 5.68 (s, 1H), 4.55 (s, 2H), 3.74 (s, 1H), 3.27 (s, 3H), 0.63 (s, 3H); $^{13}$C NMR (CDCl$_3$) δ 199.5, 166.4, 123.7, 94.3, 71.1, 54.9, 52.0, 43.6, 43.0, 38.6, 36.2, 35.8, 35.8, 35.7, 33.1, 32.5, 31.1, 27.9, 26.1, 25.9, 25.3, 10.9.

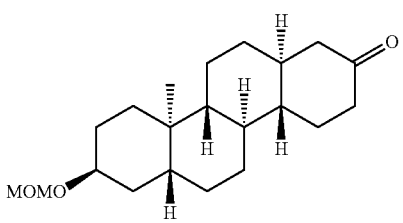

(3β,5β,8α,9β,10α,13α,14β)-3-(Methoxymethoxy)-D-Homo-18-norandrostan-17-one (36)

Liquid NH$_3$ (250 mL) was condensed in a 3-necked 500 mL round bottom flask fitted with a Dewar condenser containing Dry Ice/acetone and an overhead stirrer and then placed in a cold bath at −78° C. Li (140 mg, 20 mmol) was added and stirring continued for 30 min during which time the solution became deep blue. THF (80 mL) was added and after 10 min, compound 35 (942 mg, 2.7 mmol) dissolved in THF (40 mL) was added and stirring continued for 1 h. Solid NH$_4$Cl (5 g) was added and the solution became colorless. The reaction was allowed to warm to room temperature and the liq. NH$_3$ was allowed to evaporate. Water was added and the product extracted into EtOAc. The combined extracts were washed with brine, dried and solvent removed to give a yellow solid which was purified by flash column chromatography (silica gel, eluted with 30% EtOAc in hexanes) to give product 36 as a white solid (650 mg, 72%): mp 85-87° C.; IR $v_{max}$ 2919, 2859, 1717, 1445, 1366, 1322, 1206, 1209 cm$^{-1}$; $^1$H NMR (CDCl$_3$) δ 4.65 (s, 2H), 3.82 (s, 1H), 3.36 (s, 3H), 0.72 (s, 3H); $^{13}$C NMR (CDCl$_3$) δ 211.9, 94.5, 71.4, 55.1, 52.9, 48.6, 47.4, 43.3, 41.3, 40.8, 39.1, 35.9, 34.3, 33.5, 32.6, 30.9, 30.3, 28.3, 26.2, 24.6, 11.2.

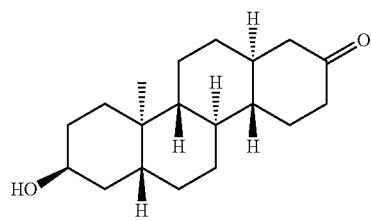

(3β,5β,8α,9β,10α,13α,14β)-3-Hydroxy-D-Homo-18-norandrostan-17-one (37)

Compound 36 (500 mg, 1.50 mmol) dissolved in MeOH (20 mL) was stirred with 6 N HCl (6 mL) at room temperature for 24 h. The HCl was neutralized by careful addition of aqueous NaHCO$_3$ solution and the MeOH removed. Water was added and the product was extracted into EtOAc. The combined extracts were washed with brine, dried and the solvents removed to give the crude product as an off-white solid which was purified by flash column chromatography (silica gel, eluted with 40-50% EtOAc in hexanes). Compound 37 was obtained as a white solid (400 mg, 92%): mp 227-229° C.; IR $v_{max}$ 3395, 2939, 2922, 2850, 1699, 1594, 1419, 1360, 1320, 1264, 1208 cm$^{-1}$; $^1$H NMR (CDCl$_3$) δ 4.04 (s, 1H), 0.71 (s, 3H); $^{13}$C NMR (CDCl$_3$) δ 211.9, 66.2, 52.9, 48.6, 47.4, 43.2, 41.2, 40.8, 38.4, 36.1, 35.7, 34.3, 32.0, 31.0, 30.3, 28.9, 28.2, 24.6, 11.0.

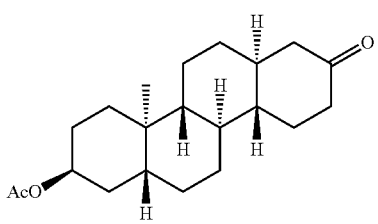

(3β,5β,8α,9β,10α,13α,14β)-3-Hydroxy-D-Homo-18-norandrostan-17-one Acetate (38)

Compound 37 (370 mg, 1.27 mmol), AcOAc (0.5 mL) and Et$_3$N (1 mL) in CH$_2$Cl$_2$ (8 mL) were stirred at room temperature for 24 h. Aqueous sat. NaHCO$_3$ (5 mL) was carefully added and the mixture was stirred for 1 h. The product was extracted into CH$_2$Cl$_2$ and the combined extracts were washed with brine, dried and the solvent removed to give an off-white solid. The crude product was purified by flash column chromatography (silica gel, eluted with 20-30% EtOAc in hexanes) to give product 38 as a white solid (400 mg, 95%): mp 141-143° C.; IR $v_{max}$ 2920, 2860, 2733, 1717, 1446, 1361, 1246 cm$^{-1}$; $^1$H NMR (CDCl$_3$) δ 4.96 (s, 1H), 2.00 (s, 3H), 0.69 (s, 3H); $^{13}$C NMR (CDCl$_3$) δ 211.6, 170.4, 69.8, 69.6, 52.7, 48.5, 47.3, 43.1, 41.1, 40.7, 39.2, 35.7, 34.2, 32.6, 32.5, 30.8, 30.2, 27.9, 25.9, 24.5, 21.4, 21.3, 11.1, 11.0.

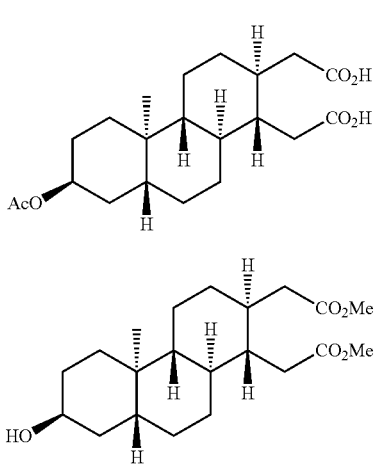

(3β,5α)-3-(Acetyloxy)-16,17-seco-D-homo-18-norandrostane-16,17-dioic Acid (39) and (3β,5α)-3-(Hydroxy)-16,17-seco-D-homo-18-norandrostane-16,17-dioic Acid Dimethyl Ester (40)

A mixture of compound 38 (96 mg) and a $CrO_3$ solution (0.7 mL) [prepared by mixing $CrO_3$ (500 mg), water (0.7 mL) and acetic acid (0.8 mL)] and a solution of aqueous methanolic acetic acid (1 mL) [prepared by mixing acetic acid (30 mL), water (1 mL) and methanol (0.05 mL)] was stirred at 60° C. for 4.5 h. The reaction was cooled to room temperature, water (2.5 mL) was added and the reaction was stirred at room temperature for 13 h. Additional water (15 mL) was added and the product was extracted into $CH_2Cl_2$. The combined extracts were dried and the solvent removed to give dicarboxylic acid 39 as a white solid which was immediately converted without characterization to diester 40 upon stirring with dry HCl in MeOH (10 mL) [prepared by adding AcCl (3 mL) to MeOH (8 mL)] at room temperature for 15 h. The HCl was cautiously neutralized with aqueous $NaHCO_3$ and the MeOH was removed. Water was added and the product was extracted into EtOAc. The combined extracts were washed with brine, dried and solvent removed to give an oil. Purification by flash column chromatography (silica gel, eluted with 40% EtOAc in hexanes) yielded compound 40 as a colorless oil (54 mg, 51%): IR $v_{max}$ 3445.55, 2924, 2858, 1738, 1436, 1361, 1258 cm$^{-1}$; $^1$H NMR (CDCl$_3$) δ 4.03 (s, 1H), 3.65 (s, 6H), 0.71 (s, 3H); $^{13}$C NMR (CDCl$_3$) δ 173.7 (2×C), 66.3, 53.0, 51.5, 51.4, 45.0, 40.8, 39.3, 38.8, 38.3, 36.1, 35.7, 35.3, 32.7, 31.9, 31.3, 28.9, 28.4, 24.4, 11.0.

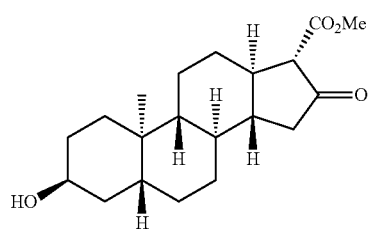

(3β,5β,8α,9β,10α,13α,14β,17a)-3-Hydroxy-16-oxo-18-norandrostane-17-carboxylic Acid Methy Ester (41)

A mixture of compound 40 (53 mg, 0.14 mmol), NaOMe (27 mg, 0.5 mmol) and THF (8 mL) was heated at reflux for 0.5 h. The reaction was cooled, acidified with 1 N HCl to pH 3 and the product extracted into $CH_2Cl_2$ (3×75 mL). The combined extracts were washed with brine, dried and solvents removed to give a white solid. The crude product was purified by flash column chromatography (silica gel, eluted with 40% EtOAc in hexanes) gave pure product 41 as a white solid (34 mg, 71%): mp 136-138° C.; IR $v_{max}$ 3435, 2920, 2855, 1756, 1727, 1435, 1410, 1384, 1339, 1261 cm$^{-1}$; $^1$H NMR (CDCl$_3$) δ 4.06 (t, 1H, J=2.5 Hz), 3.75 (s, 3H), 2.86 (d, 1H, J=2.5 Hz), 2.50 (dd, 1H, J=18.0 Hz, 5.8 Hz), 0.78 (s, 3H); $^{13}$C NMR (CDCl$_3$) δ 210.2, 169.5, 66.3, 61.9, 53.1, 52.3, 47.1, 46.6, 43.2, 41.6, 38.7, 36.2, 35.7, 32.2, 31.9, 30.0, 28.9, 28.0, 24.5, 11.0.

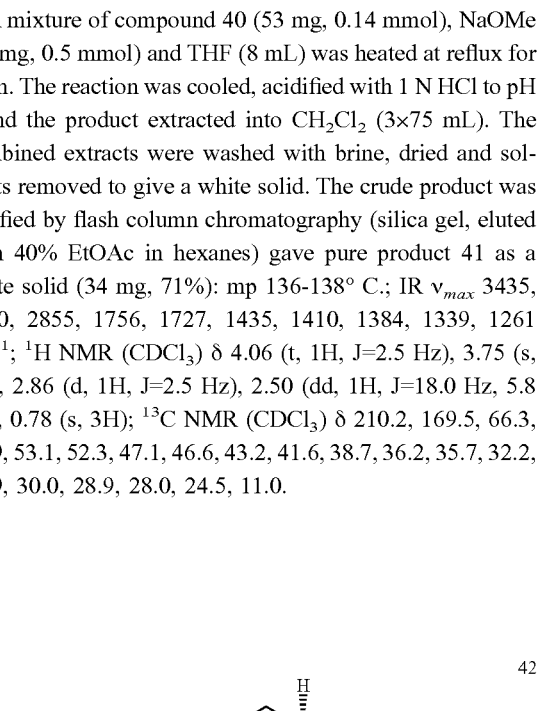

(3β,5β,8α,9β,10α,13α,14β)-18-Norandrostan-16-one (42, KK-114)

A mixture of β-ketoester 41 (25 mg, 0.075 mmol), LiCl (100 mg) and DMF was heated at 160° C. for 30 min under $N_2$. The reaction mixture was cooled, diluted with water and extracted with EtOAc. The combined organic extracts were dried and concentrated to give an off-white solid. The crude product was purified by flash column chromatography (silica gel, eluted with 30-40% EtOAc in hexanes) to give product 42 as a white solid (18 mg, 86%): mp 174-177° C.; $[α]_D^{23}$ +171.9 (c 0.1, CHCl$_3$); IR $v_{max}$ 3475, 2923, 2853, 1723 cm$^{-1}$; $^1$H NMR (CDCl$_3$) δ 4.06 (br s, 1H), 2.36 (m, 2H), 0.78 (s, 3H); $^{13}$C NMR (CDCl$_3$) δ 218.5, 66.4, 53.3, 50.2, 45.9, 43.8, 43.3, 41.7, 38.8, 36.2, 35.8, 32.2, 32.0, 31.1, 29.0, 28.1, 24.8, 11.1. Anal. ($C_{18}H_{28}O_2$): C, 78.21%; H, 10.21%. Found: C, 78.16%; H, 10.12%.

Scheme 4

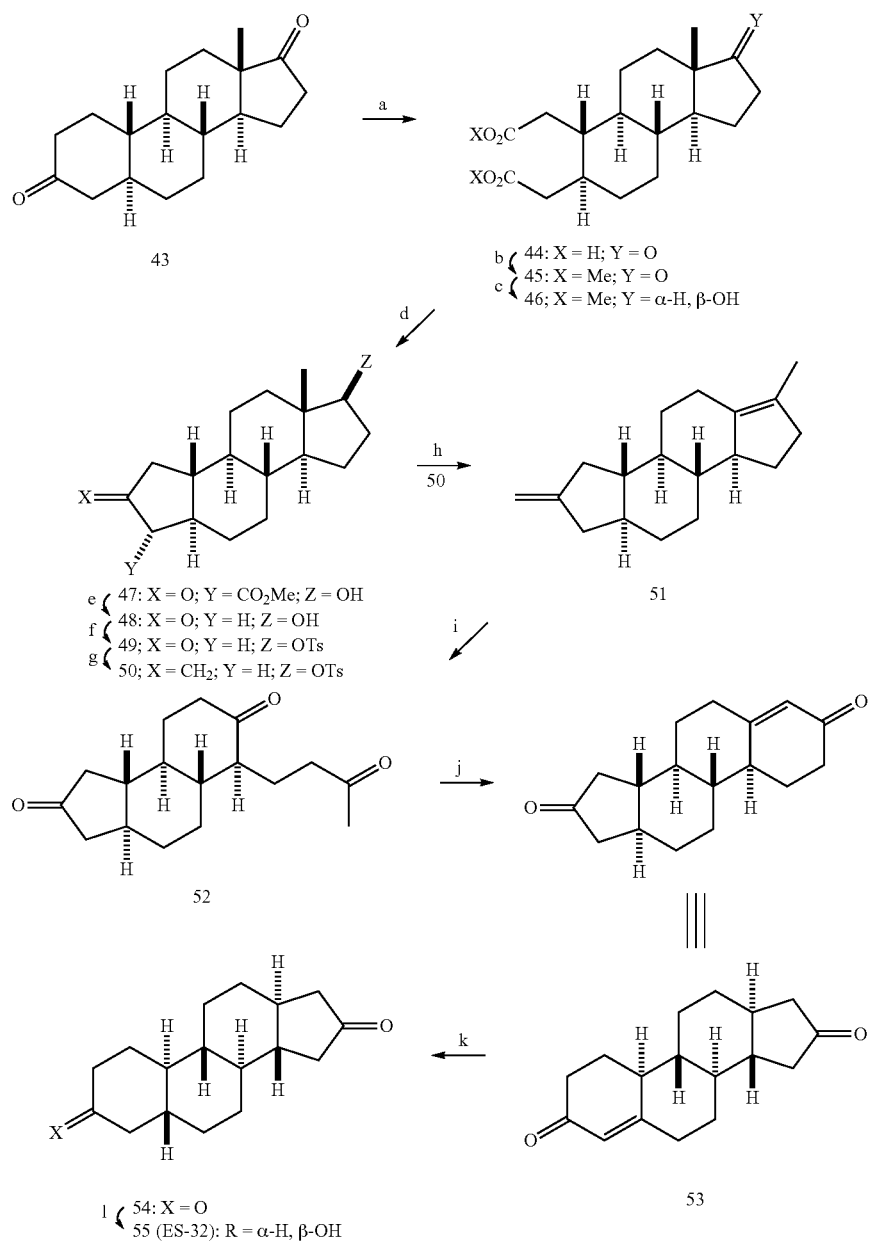

In accordance with Scheme 4, the following compounds were prepared, using methods generally known in the art and as outlined below.

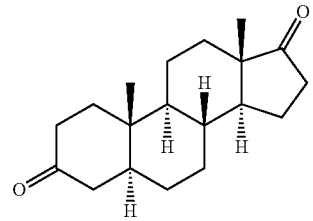

(5α)-Estrane-3,17-dione (43).
The known compound was prepared as described previously. (Stastna, E.; Rath, N. P.; Covey, D. F. The use of symmetry in enantioselective synthesis: Four pairs of chrysene enantiomers prepared from 19-nortestosterone. *Org. Biomol. Chem.* 2011, 9, 4685-4694.)

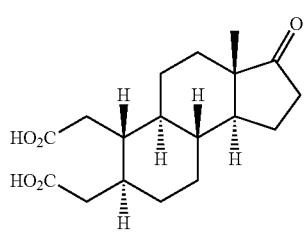

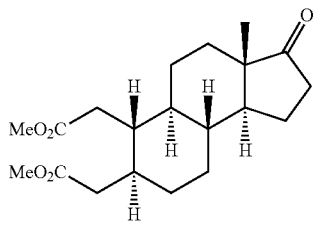

(5α)-17-Oxo-3,4-secoestrane-2,3-dicarboxylic Acid (44) and (5α)-17-Oxo-3,4-secoestrane-2,3-dicarboxylic Acid Dimethyl Ester (45)

A solution of CrO$_3$ (10.9 g), H$_2$SO$_4$ (98%, 16 mL), and water (76 mL) was added dropwise to a stirred solution of compound 43 (7.9 g, 28.5 mmol) in AcOH (80 mL) at 65° C. The reaction was heated at 70° C. for 1 h. Then, crushed ice and water (500 mL) were added and the mixture was stirred at room temperature for 1 h. Steroid 44 precipitated and was filtered, washed with water, and dried overnight at room temperature to give pure dicarboxylic acid (5.53 g, 60%) as a white solid. The aqueous phase was extracted with CH$_2$Cl$_2$ (2×150 mL), and the combined extracts were washed with brine (2×100 mL), dried and evaporated to afford impure dicarboxylic acid 44 (2 g, 21%) as an oily residue. Pure steroid 44 had: $^1$H NMR (300 MHz, CDCl$_3$) δ 0.88 (3H, s); $^{13}$C NMR (75 MHz, CDCl$_3$) δ 221.5, 179.43, 179.25, 50.6, 47.9, 47.7, 43.2, 40.6, 39.4, 38.8, 36.0, 35.3, 32.3, 31.6, 29.4, 26.0, 21.7, 13.9.

AcCl (6 mL, 23 mmol) was added to steroid 44 (7.53 g) dissolved in MeOH (100 mL) and the reaction was stirred at room temperature for 2 h. Then, water (50 mL) was added and the product was extracted into CH$_2$Cl$_2$ (2×100 mL). The combined extracts were washed with water, dried and the solvent removed to yield an oily residue which was purified by flash column chromatography (silica gel eluted with 15% EtOAc in hexanes) to give steroid 45 (4.43 g, 52%) as an oil. Unreacted steroid 44 was reclaimed by washing the silica gel with MeOH and the esterification procedure was repeated to give additional product 45 (780 mg, 9%) as an oil: IR ν$_{max}$ 2925, 2858, 1737 cm$^{-1}$; $^1$H NMR (CDCl$_3$) δ 3.65 (6H, s), 0.86 (3H, s); $^{13}$C NMR (CDCl$_3$) δ 220.9, 173.6 (2×C), 51.7, 51.6, 50.6, 47.99, 47.90, 43.3, 40.6, 39.3, 39.1, 36.0, 35.3, 32.3, 31.7, 29.4, 25.9, 21.7, 13.9.

of water (50 mL) and AcOH (2 mL) was added and the solution was stirred for 1 h. The product was extracted into CH$_2$Cl$_2$ (2×125 mL), washed with an aqueous 1 N HCl, sat. aqueous NaHCO$_3$, brine, dried and the solvent removed. Flash column chromatography (silica gel, eluted with 15% EtOAc in hexanes) gave secosteroid 46 (1.16 g, 74%) as an oily product: IR ν$_{max}$ 3452, 2950, 2921, 2867, 1733 cm$^{-1}$; $^1$H NMR (CDCl$_3$) δ 3.60-3.65 (7H, m), 0.73 (3H, s); $^{13}$C NMR (CDCl$_3$) δ 173.7 (2×C), 82.0, 51.68, 51.62, 50.2, 47.9, 43.5, 43.1, 41.2, 39.5, 39.2, 36.9, 35.4, 32.5, 30.7, 30.1, 26.3, 23.3, 11.2.

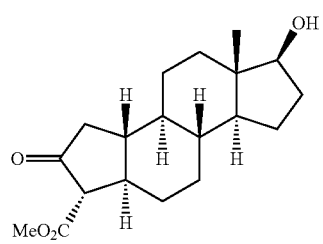

(3α,5α,17β)-17-Hydroxy-2-oxo-A-norestrane-3-carboxylic Acid Methyl Ester (47)

A NaOMe solution (5 mL) was prepared by dissolving Na (1.14 g, 49 mmol) in MeOH (25 mL) followed by MeOH evaporation on a rotary evaporator. Dry THF (30 mL) was added and the flask was filled with N$_2$. Steroid 46 (5 g, 14.1 mmol) dissolved in dry THF (50 mL) was slowly added. The reaction mixture was heated at 100° C. for 1 h under N$_2$ and then allowed to attain room temperature. Then 1 N HCl (15 mL) was slowly added and the product was extracted into CH$_2$Cl$_2$ (2×100 mL). The combined extracts were washed with brine, dried and the solvent removed. Flash column chromatography (silica gel, eluted with 15% EtOAc in hexanes) gave product 47 (3.7 g, 81%) as a white solid: mp 138-142° C. (EtOAc/hexanes); IR ν$_{max}$ 3440, 2918, 2866, 1756, 1727 cm$^{-1}$; $^1$H NMR (CDCl$_3$) δ 3.75 (3H, s), 3.67 (t, 1H, J=8 Hz), 2.88 (d, 1H, J=12.6 Hz), 2.48 (dd, 1H, J=6.6 Hz, 18 Hz), 0.77 (3H, s). $^{13}$C NMR (CDCl$_3$) δ210.1, 169.7, 81.9, 62.1, 52.4, 49.7, 48.7, 47.5, 45.7, 43.6, 43.3, 41.6, 36.5, 30.5, 30.2, 29.9, 27.1, 23.3, 11.4. Anal. (C$_{19}$H$_{28}$O$_4$): C, 71.22%; H, 8.81%. Found: C, 71.12%; H, 8.68%.

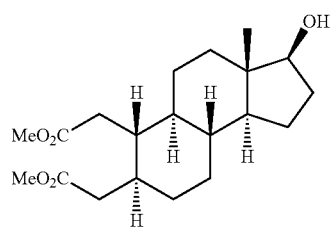

(5α,17β)-17-Hydroxy-3,4-secoestrane-2,3-dicarboxylic Acid Dimethyl Ester (46)

Steroid 45 (1.55 g, 31.4 mmol) was dissolved in stirred EtOH (20 mL) and cooled in an ice-bath. NaBH$_4$ (218 g, 5.8 mmol) was added in small portions. After 1.5 h, a solution

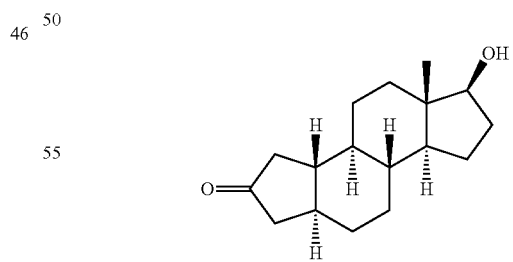

(5α,17β)-17-Hydroxy-A-norestran-2-one (48)

LiCl (1.95 g, 46.1 mmol) was added to a solution of steroid 47 (3.7 g, 11.5 mmol) dissolved in DMF (50 mL) and water (0.5 mL) and the reaction was heated at 160° C. for 35 min. Then, crushed ice and water were added and the product was extracted into $CH_2Cl_2$ (2×120 mL). The combined extracts were washed with water and dried. After solvent evaporation, the residue was purified by flash column chromatography (silica gel, eluted with 10% EtOAc in hexanes) to give product 48 (2.6 g, 85%) as a white solid: mp 177-179° C. (EtOAc/hexanes); IR $v_{max}$ 3450, 2915, 2861, 1732 $cm^{-1}$; $^1H$ NMR ($CDCl_3$) δ 0.77 (3H, s), 2.41-2.31 (2H, m), 3.66 (t, 1H, J=8 Hz). $^{13}C$ NMR ($CDCl_3$) δ 218.3, 82.0, 49.9, 48.9, 48.6, 46.1, 44.2, 43.9, 43.6, 41.7, 36.6, 30.9, 30.64, 30.61, 27.1, 23.4, 11.4. Anal. ($C_{17}H_{26}O_2$): C, 77.82%; H, 9.99%. Found: C, 77.69%; H, 10.02%.

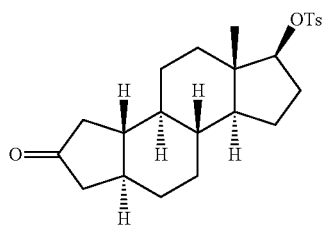

(5α,17β)-17-[[(4-Methylphenyl)sulfonyl]oxy]-A-norestran-2-one (49)

A solution of steroid 39 (2.46 g, 9.37 mmol), DMAP (57 mg, 0.49 mmol), and p-TsCl (6.25 g, 32.8 mmol) in anhydrous pyridine (50 mL) was heated at 65° C. overnight. The reaction mixture was poured into ice-water and the product extracted into $CH_2Cl_2$ (2×75 mL). The combined extracts were washed with aqueous HCl, aqueous $NaHCO_3$, brine, and dried. After solvent evaporation, the oily residue was purified by flash column chromatography (silica gel, eluted with 10% EtOAc in hexanes) to give steroid 39 (3.56 g, 91%) as a white solid: mp 138-139° C. (ether/hexanes); IR $v_{max}$ 2920, 2858, 1741, 1598, 1357, 1188, 1176 $cm^{-1}$; $^1H$ NMR ($CDCl_3$) δ 7.80-7.77 (2H, m), 7.34-7.31 (2H, m), 4.28 (t, 1H, J=8 Hz), 2.45 (3H, s), 2.33 (dd, 2H, J=6.6 Hz, 18 Hz), 0.82 (3H, s). $^{13}C$ NMR ($CDCl_3$) 5217.9, 144.6, 134.6, 129.8 (2×C), 128.0 (2×C), 90.0, 48.9, 48.6, 48.4, 45.9, 44.1, 43.8, 43.6, 41.2, 36.0, 30.8, 30.4, 27.7, 26.8, 23.3, 21.8, 12.0. Anal. ($C_{24}H_{32}O_4S$): C, 69.20%; H, 7.74%. Found: C, 69.09%; H, 7.35%.

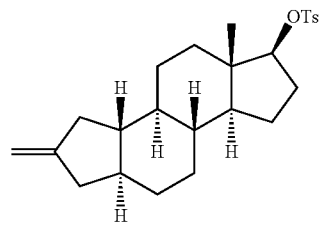

(5α,17β)-2-Methylene-17-[[4-(methylphenyl)sulfonyl]oxy]-A-norestrane (50)

A solution of n-BuLi (2.5 M, 24.1 mmol, 9.6 mL) was added dropwise to a solution of MeP(Ph)$_3$Br (8.85 g, 24.7 mmol) in dry benzene (70 mL) and dry THF (12 mL) under $N_2$ and the mixture was stirred for 30 min. A solution of steroid 49 (2.58 g, 6.19 mmol) in dry benzene (35 mL) was added and stirred at room temperature. After 6 h, the reaction was diluted with water (50 mL) and extracted with EtOAc (2×75 mL). The combined extracts were washed with brine, dried and the solvents evaporated. Flash column chromatography on (silica gel, eluted with 5% EtOAc in hexanes) gave steroid 50 (2.05 g, 80%) as a white solid: mp 136-137° C. (EtOAc/hexanes); IR $v_{max}$ 2920, 2855, 1657, 1598, 1359 $cm^{-1}$; $^1H$ NMR ($CDCl_3$) δ 7.80-7.77 (2H, m), 7.34-7.31 (2H, m), 4.83 (2H, m), 4.27 (t, 1H, J=8 Hz), 2.45-2.36 (5H, m), 0.81 (3H, s); $^{13}C$ NMR ($CDCl_3$) δ 151.5, 144.5, 134.6, 129.8 (2×C), 128.0 (2×C), 105.9, 90.3, 51.0, 49.0, 48.9, 46.7, 43.7, 41.3, 39.6, 37.6, 36.2, 31.0, 30.8, 27.8, 26.7, 23.5, 21.8, 12.1. Anal. ($C_{25}H_{31}O_3S$): C, 72.42%; H, 8.27%. Found: C, 72.59%; H, 8.07%.

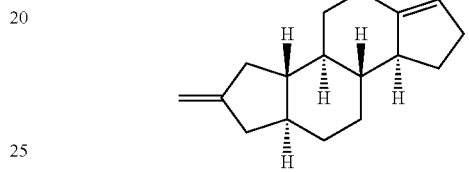

(5α)-17-Methyl-2-Methylene-A-norgon-13(17)-ene (51)

Steroid 50 (2 g, 4.8 mmol) was dissolved in anhydrous toluene (50 mL) and heated to 100° C. MeMgBr (3.0 M in $Et_2O$, 8 mL, 24 mmol) was added dropwise to the stirring hot solution under an $N_2$ atmosphere and a white precipitate appeared. The reaction was heated for 1 h at 115° C. The flask was cooled, a few pieces of crushed ice were added, and the pH of the solution was adjusted to pH 2 by dropwise addition of 2 N aqueous $H_2SO_4$. The toluene layer was separated and the aqueous layer was extracted with EtOAc (2×100 mL). The combined extracts were washed with brine, dried and the solvents evaporated. Flash column chromatography on (silica gel, eluted with 1% EtOAc in hexanes) gave steroid 51 (1.04 g, 90%) as an oily product: IR $v_{max}$ 3067, 2921, 2851, 1657, 1441 $cm^{-1}$; $^1H$ NMR ($CDCl_3$) δ 4.86 (2H, m), 1.62 (3H, s). $^{13}C$ NMR ($CDCl_3$) δ 151.9, 136.7, 128.3, 105.7, 100.2, 52.6, 51.5, 51.3, 47.1, 46.4, 39.7, 37.8, 37.4, 31.5, 31.2, 28.4, 25.6, 13.6.

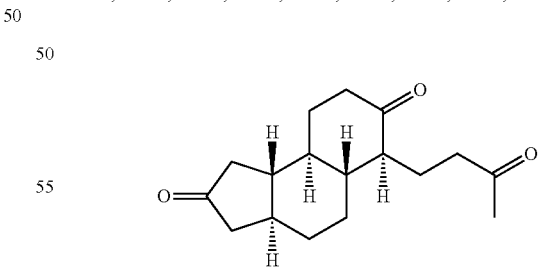

(3aS,5aR,6S,9aR,9bS)-Decahydro-6-(3-oxobutyl)-1H-benz[e]indene-2,7-dione (52)

A solution of steroid 51 (760 mg, 3.13 mmol) in $CH_2Cl_2$ (55 mL) was treated with $O_3$ at −78° C. until a blue color persisted (ca. 1 hr). $O_2$ was passed through the solution for 30 min until the blue color disappeared. AcOH (50 mL) was added and the CH$_2$Cl$_2$ was evaporated under vacuum without heating. Then, AcOH (10 mL) and Zn dust (2.03 g, 31 mmol) were added and the reaction mixture was stirred at room temperature for 1.5 h. Zn dust was filtered off through cotton, washing with CH$_2$Cl$_2$ (100 mL). The Zn dust was stirred with EtOAc (50 mL) for 1 h. The solids were filtered off, the combined solvents were evaporated and the product was purified by flash column chromatography (silica gel, eluted with 20% EtOAc in hexanes) to give compound 52 (390 mg, 51%) as an oil: IR $\nu_{max}$ 3406, 2919, 2859, 1742, 1709 cm$^{-1}$; $^1$H NMR (CDCl$_3$) 52.09 (3H, s); $^{13}$C NMR (CDCl$_3$) δ 217.0, 211.6, 209.1, 53.9, 48.4, 47.4, 46.5, 45.6, 43.6, 43.2, 41.6, 40.9, 32.0, 31.1, 30.5, 30.0, 19.5.

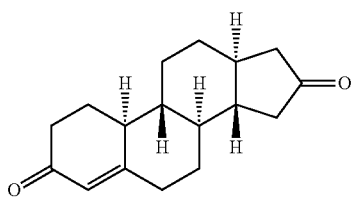

(8α,9β,10α,13α,14β)-Gon-4-ene-3,16-dione (53)

A solution of NaOH [10% w/v in MeOH/water (9:1), 2 mL] was added to a solution of compound 52 (392 g, 1.41 mmol) in MeOH (20 mL) and the mixture was stirred at room temperature. After 3 h, a few pieces of crushed ice were added, the pH was adjusted to pH 2 by adding aqueous 1 N HCl, and the product was extracted into CH$_2$Cl$_2$ (2×70 mL). The combined extracts were washed with brine, dried and the solvent evaporated. Purification by flash column chromatography (silica gel, eluted with 20% EtOAc in hexanes) gave compound 53 (302 mg, 82%) as a white solid: mp 147-148° C. (EtOAc/hexanes); IR $\nu_{max}$ 2932, 2854, 1740, 1662, 1612 cm$^{-1}$; $^1$H NMR (CDCl$_3$) δ 5.84 (1H, s); $^{13}$C NMR (CDCl$_3$) δ 217.4, 199.8, 165.8, 124.9, 48.7, 48.6, 46.5, 45.8, 43.6, 43.2, 42.6, 36.6, 35.3, 31.4, 30.7, 30.3, 26.5. Anal. (CO$_{17}$H$_{22}$O$_2$) C, 79.03%; H, 8.58%. Found: C, 79.09%; H, 8.38%.

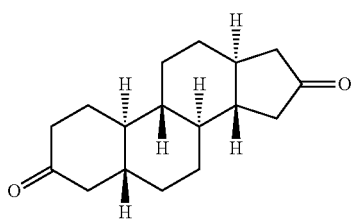

(5β,8α,9β,10α,13α,14β)-Gonane-3,16-dione (54)

Anhydrous NH$_3$ (10 mL) was condensed using a Dewar condenser into a three-neck flask containing Li metal (20 mg, 2.9 mmol) at −78° C. Then, anhydrous THF (12 mL) was added and the resulting blue solution was stirred for 0.5 h. A solution of compound 53 (150 mg, 0.58 mmol) in dry THF (6 mL) was added dropwise to the vigorously stirred solution. After 2 h of stirring, the reaction color was discharged by careful addition of solid NH$_4$Cl in portions and left overnight while the NH$_3$ evaporated. The reaction was then acidified with aqueous 1 N HCl and the product was extracted into EtOAc (2×50 mL). The combined organic phases were washed with brine, dried and the solvent evaporated. The residue was dissolved in acetone (50 mL) and Jones reagent was added dropwise until an orange color persisted. The course of the reaction was checked by TLC. Then, 2-propanol was added dropwise until the reaction mixture turned green. After 30 min, the reaction mixture was poured into water-ice. The product was extracted into CH$_2$Cl$_2$ (2×30 mL). The combined extracts were washed with brine, dried and the solvent was evaporated. Flash column chromatography (silica gel, eluted with 15% EtOAc in hexanes) gave compound 54 (95 mg, 63%) as a white solid: mp 188-189° C. (EtOAc/hexanes); IR $\nu_{max}$ 2914, 2867, 1740, 1705 cm$^{-1}$; $^1$H NMR (CDCl$_3$) δ 0.90-2.42 (24H, m); $^{13}$C NMR (CDCl$_3$) δ 218.1, 211.6, 49.1, 48.7, 47.3, 46.8, 46.0, 45.9, 43.7, 43.5, 43.4, 41.4, 33.8, 31.1, 31.0, 30.4, 30.0.

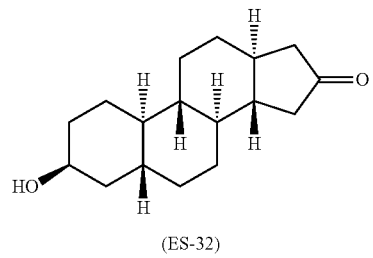

(ES-32)

(3β,5β,8α,9β,10α,13α,14β)-3-Hydroxygonan-16-one (55, ES-32)

K-Selectride (1M in THF, 0.45 mL) was added dropwise under N$_2$ to a cooled solution (−78° C.) of compound 54 (108 mg, 0.41 mmol) in anhydrous THF (15 mL). After 2 h stirring at −78° C., water (2 mL) was added and the mixture was allowed to reach room temperature. Then, aqueous NaOH (2 mL, 6 M), and 30% H$_2$O$_2$ (2 mL) were added and the reaction was stirred for 30 min. The product was extracted with CH$_2$Cl$_2$ (2×50 mL), the combined extracts were washed with aqueous HCl (1 N), saturated aqueous NaHCO$_3$, and brine. Solvent was dried and evaporated. Flash column chromatography (silica gel, eluted with 10% EtOAc in hexanes) gave product 55 (76 mg, 70%) as a white solid: mp 168-169° C. (EtOAc/hexanes); [α]$_D^{23}$ +218.6 (c 0.17, CHCl$_3$). IR $\nu_{max}$ 3466, 2917, 2846, 1724 cm$^{-1}$; $^1$H NMR (CDCl$_3$) δ 4.08 (1H, m), 2.30-2.41 (2H, m), 1.97-2.10 (2H, m). $^{13}$C NMR (CDCl$_3$) δ 218.5, 66.5, 49.3, 47.7, 47.3, 47.2, 46.1, 43.8, 43.6, 40.7, 35.9, 33.5, 33.1, 31.4, 31.1, 29.6, 23.6. Anal. (C$_{17}$H$_{26}$O$_2$): C, 77.82%; H, 9.99%. Found: C, 78.02%; H, 9.79%.

Scheme 5

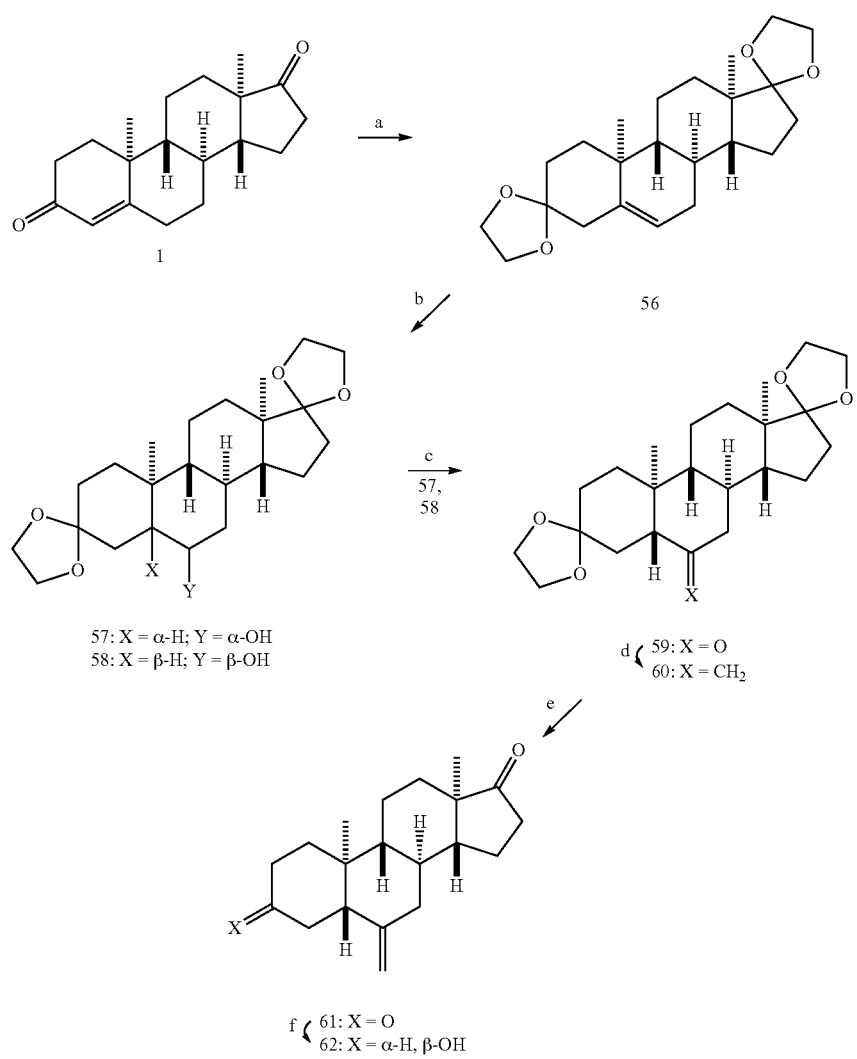

In accordance with Scheme 5, the following compounds were prepared, using methods generally known in the art and as outlined below.

56

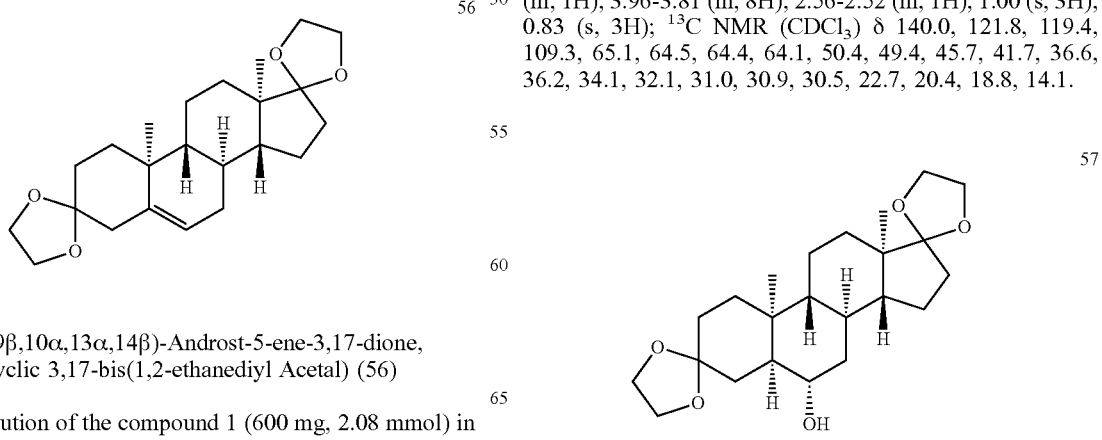

(8α,9β,10α,13α,14β)-Androst-5-ene-3,17-dione, Cyclic 3,17-bis(1,2-ethanediyl Acetal) (56)

To a solution of the compound 1 (600 mg, 2.08 mmol) in benzene (150 mL) was added ethylene glycol (1.0 mL) and PTSA (150 mg) at 23° C. The mixture was refluxed in a Dean-Stark apparatus for 16 h. Solvent was removed and the residue was purified by flash column chromatography (silica gel, eluted with 17% EtOAc in hexanes) to give compound 56 (605 mg, 78%) as an oil: $^1$H NMR (CDCl$_3$) δ 5.32-5.30 (m, 1H), 3.96-3.81 (m, 8H), 2.56-2.52 (m, 1H), 1.00 (s, 3H), 0.83 (s, 3H); $^{13}$C NMR (CDCl$_3$) δ 140.0, 121.8, 119.4, 109.3, 65.1, 64.5, 64.4, 64.1, 50.4, 49.4, 45.7, 41.7, 36.6, 36.2, 34.1, 32.1, 31.0, 30.9, 30.5, 22.7, 20.4, 18.8, 14.1.

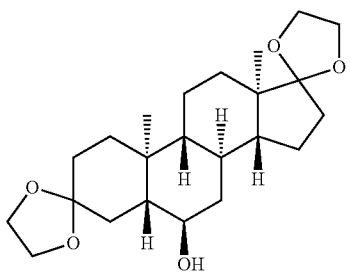

(5α,6α,8α,9β,10α,13α,14β)-6-Hydroxyandrostane-3,17-dione, Cyclic 3,17-bis(1,2-ethanediyl Acetal) (57) and (5β,6β,8α,9β,10α,13α,14β)-6-Hydroxyandrostane-3,17-dione, Cyclic 3,17-bis(1,2-ethanediyl Acetal) (58)

To a solution of compound 56 (600 mg, 1.61 mmol) in THF (30 mL) was added $BH_3$.THF complex (3.0 mL, 1.0 M, 3.0 mmol) at 0° C. After 1 h, the mixture was warmed up to 23° C. for an additional 1 h. To the reaction was slowly added 3 M NaOH (20 mL) and $H_2O_2$ (5 mL) at 23° C. The reaction was stirred for 1 h and the product extracted into EtOAc (3×100 mL). The combined extracts were washed with brine (3×50 mL). Solvent was removed and the residue was purified by flash column chromatography (silica gel, eluted with 33% EtOAc in hexanes) to give products 57 and 58 as oils.

Product 57 (290 mg, 46%) had: $^1$H NMR (CDCl$_3$) δ 3.91-3.78 (m, 8H), 3.66 (d, J=2.0 Hz, 1H), 1.09 (s, 3H), 0.81 (s, 3H); $^{13}$C NMR (CDCl$_3$) δ 119.3, 109.2, 72.4, 65.1, 64.4, 64.1, 64.0, 50.2, 47.6, 45.9, 39.9, 35.6, 34.6, 34.3, 34.1, 33.4, 30.8, 30.6, 29.6, 25.2, 22.5, 20.1, 14.4.

Product 58 (50 mg, 8%) had: $^1$H NMR (CDCl$_3$) δ 3.91-3.79 (m, 8H), 3.58-3.30 (m, 1H), 0.80 (s, 3H), 0.79 (s, 3H); $^{13}$C NMR (CDCl$_3$) δ 119.2, 109.0, 69.4, 65.0, 64.5, 64.1, 64.0, 53.1, 50.6, 49.9, 45.9, 41.0, 36.3, 36.2, 34.5, 34.1, 32.1, 30.9, 30.4, 22.6, 20.4, 14.3, 12.5.

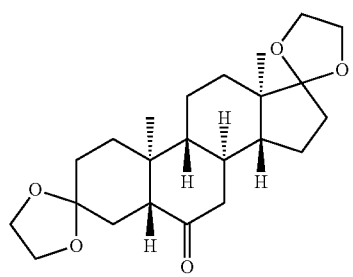

(5β,8α,9β,10α,13α,14β)-Androstane-3,6,17-trione, Cyclic 3,17-bis(1,2-ethanediyl Acetal) (59)

To a solution of unseparated products 57 and 58 (340 mg, 0.87 mmol) in CH$_2$Cl$_2$ (20 ml) was added pyridium chlorochromate (PCC, 648 mg, 3.0 mmol) at 23° C. The reaction was stirred 2 h and then transferred to a short silica gel column to give crude product 59 (336 mg). Crude product 59 was dissolved in methanol (30 mL) and then added K$_2$CO$_3$ (2.0 g) was added at 23° C. The reaction was refluxed for 16 h. methanol was removed and the residue was purified by flash column chromatography (silica gel, eluted with 20% EtOAc in hexanes) to give product 59 (200 mg, 59%) as an oil: $^1$H NMR (CDCl$_3$) δ 3.91-3.79 (m, 8H), 2.47 (t, J=7.8 Hz, 1H), 2.28 (dd, J=12.9 Hz, 2.3, 1H), 0.78 (s, 3H), 0.70 (s, 3H); $^{13}$C NMR (CDCl$_3$) δ 211.0, 118.8, 108.8, 65.1, 64.4, 64.1, 64.0, 55.8, 53.2, 50.4, 46.1, 45.8, 40.7, 37.9, 35.5, 33.9, 30.6, 30.1, 29.7, 22.3, 20.7, 14.2, 12.3.

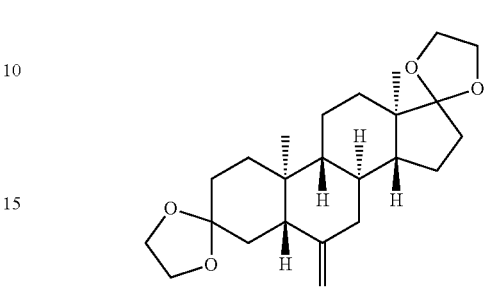

(5β,8α,9β,10α,13α,14β)-6-Methylene-androstane-3,17-dione, Cyclic 3,17-bis(1,2-ethanediyl Acetal) (60)

In a dry flask, methylphenylphosphonium bromide (2.1 g, 6.0 mmol) and THF (30 mL) were combined. Potassium t-butoxide (560 mg, 5.0 mmol) was added. The mixture was stirred under N$_2$ for 45 min at reflux. Compound 59 (200 mg, 0.51 mmol) was dissolved in THF (10 mL) and transferred by syringe to the refluxing reaction. The yellow mixture was stirred for an additional 1 h. at reflux. After cooling, brine (50 mL) was added and the product extracted into EtOAc (2×100 mL). Solvent was removed and the residue was purified by flash column chromatograph (silica gel, eluted with 14% EtOAc in hexanes) to give product 60 (176 mg, 88%) as oil: $^1$H NMR (CDCl$_3$) δ 4.65 (s, 1H), 4.35 (s, 1H), 3.91-3.78 (m, 8H), 2.25 (d, J=12.5 Hz, 1H), 0.78 (d, J=1.6 Hz, 3H), 0.65 (d, J=1.2 Hz, 3H); $^{13}$C NMR (CDCl$_3$) δ 149.3, 119.2, 109.5, 105.5, 65.1, 64.4, 64.1, 64.0, 53.9, 50.1, 48.1, 45.9, 41.1, 37.6, 37.5, 35.4, 34.1, 33.4, 30.8, 30.5, 22.5, 20.8, 14.3, 11.5.

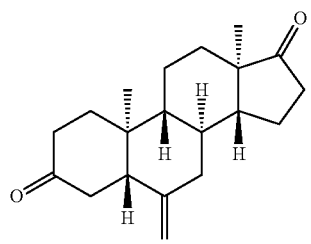

(5β,8α,9β,10α,13α,14β)-6-Methylene-androstane-3,17-dione (61)

To a solution of compound 60 (176 mg, 0.45 mmol) in acetone/H$_2$O (20 mL/1 mL) was added PTSA (50 mg) at 23° C. The reaction was stirred for 6 h and then NaHCO$_3$ (solid, 0.5 g) was added. Solvent was removed and the residue was purified by flash column chromatograph (silica gel, eluted with 20% EtOAc in hexanes) to give product 61 (129 mg, 95%) as an oil: $^1$H NMR (CDCl$_3$) δ 4.81 (s, 1H), 4.43 (s, 1H), 0.88 (s, 3H), 0.84 (s, 3H); $^{13}$C NMR (CDCl$_3$) δ 220.4, 211.8, 147.1, 107.2, 54.0, 51.0, 50.7, 47.7, 40.4, 40.3, 37.9, 37.8, 37.6, 36.6, 35.7, 31.2, 21.6, 20.8, 13.7, 11.6.

Scheme 6

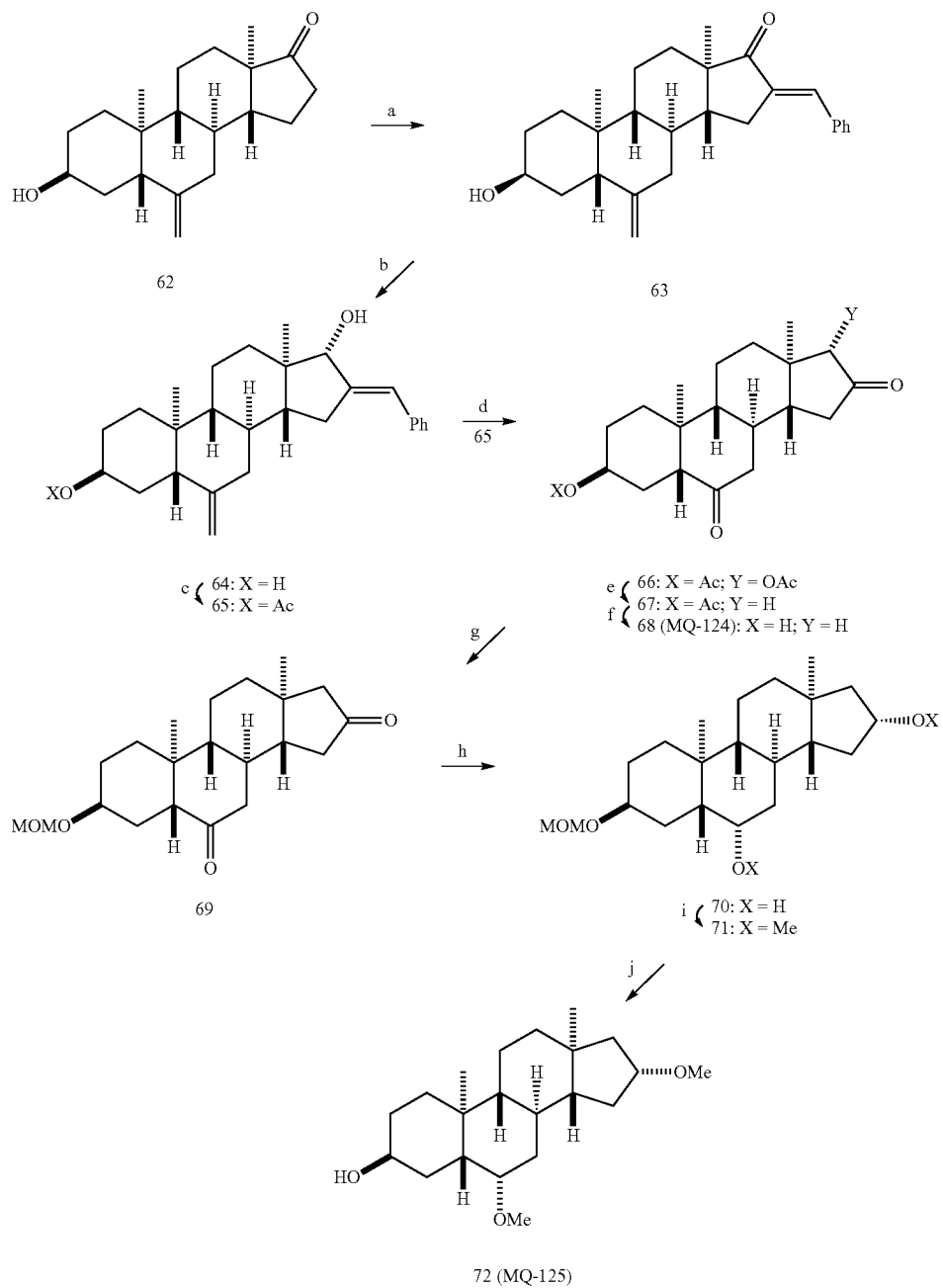

In accordance with Scheme 6, the following compounds were prepared, using methods generally known in the art and as outlined below.

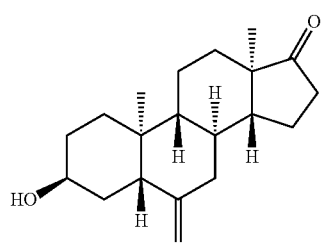

(3β,5β,8α,9β,10α,13α,14β)-3-Hydroxy-6-methyl-ene-androstan-17-one (62)

To a solution of compound 61 (128 mg, 0.43 mmol) in THF (20 mL) was slowly added K-selectride (1.0 mL, 1.0 M, 1.0 mmol) at −78° C. After 2 h, 3 M NaOH (20 mL) and $H_2O_2$ (5 mL) were added at −78° C. The reaction was then warmed up to 23° C. for 1 h. The product was extracted into EtOAc (3×100 mL) and the combined extracts washed with brine (3×50 mL). Solvent was removed and the residue was purified by flash column chromatograph (silica gel, eluted with 20% EtOAc in hexanes) to give product 62 (105 mg, 82%): $^1$H NMR (CDCl$_3$) δ 4.72 (d, J=1.6 Hz, 1H), 4.43 (d, J=1.6 Hz, 1H), 4.15-4.13 (m, 1H), 0.83 (s, 3H), 0.66 (s, 3H);

¹³C NMR (CDCl₃) δ 221.2, 149.4, 106.0, 66.0, 54.6, 51.4, 47.9, 43.5, 40.9, 38.3, 36.9, 35.8, 31.6, 31.4, 31.2, 28.5, 21.7, 20.3, 13.8, 11.4.

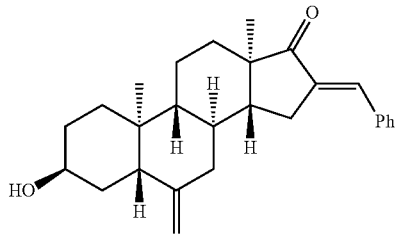

(3β,5β,8α,9β,10α,13α,14β)-3-Hydroxy-6-Methylene-16-(phenylmethylene)-androstan-17-one (63)

Compound 62 (105 mg, 0.35 mmol) and benzaldehyde (0.14 mL, 1.4 mmol) were added to KOH (50 mg) dissolved in EtOH (10 mL) and the reaction was stirred at room temperature for 16 h. Ethanol was removed and the residue was purified by flash column chromatography (silica gel, eluted with 20% EtOAc in hexanes) to give product 63 (121 mg, 86%): ¹H NMR (CDCl₃) δ 7.56-7.26 (m, 6H), 4.79 (s, 1H), 4.47 (s, 1H), 4.17-4.4.14 (m, 1H), 2.91 (dd, J=15.7 Hz, 6.3 Hz, 1H), 0.95 (d, J=1.9 Hz, 3H), 0.72 (d, J=2.3 Hz, 3H); ¹³C NMR (CDCl₃) δ 209.7, 149.3, 135.9, 135.5, 133.1, 130.3 (2×C), 129.2, 128.6 (2×C), 106.1, 66.0, 54.7, 49.5, 47.6, 43.5, 41.0, 38.4, 36.6, 31.5, 31.2, 29.1, 28.4, 20.3, 14.5, 11.5.

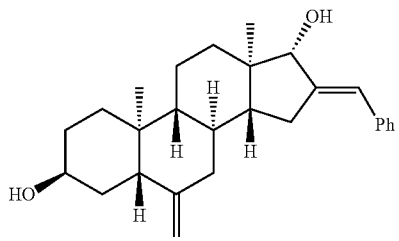

(3β,5β,8α,9β,10α,13α,14β,17α)-6-Methylene-16-(phenylmethylene)-androstane-3,17-diol (64)

Compound 63 was dissolved in EtOH, cooled to 0° C. and CeCl₃.7 H₂O (745 mg, 2.0 mmol) and NaBH₄ (766 mg, 2.0 mmol) were added. The reaction was allowed to warm to room temperature and stirring was continued for 3 h. Glacial AcOH ((7 mL) was added and the product extracted into EtOAc (3×50 mL). The combined extracts were dried and the solvents removed to give product 64 (121 mg, 99%) as an oil: ¹H NMR (CDCl₃) δ 7.32-7.24 (m, 5H), 7.14-7.10 (m, 1H), 6.44 (d, J=2.3 Hz, 1H), 4.69 (s, 1H), 4.37 (s, 1H), 4.09-4.08 (m, 1H), 3.98 (s, br, 1H), 0.62 (s, 3H), 0.60 (s, 3H); ¹³C NMR (CDCl₃) δ 149.6, 146.0, 137.8, 128.3 (2×C), 128.2 (2×C), 126.4, 123.0, 105.8, 84.9, 66.1, 54.8, 48.5, 43.5, 43.1, 41.7, 38.4, 36.9, 36.3, 31.6, 31.3, 30.8, 29.2, 28.4, 20.7, 11.5, 11.2.

(3β,5β,8α,9β,10α,13α,14β,17α)-6-Methylene-16-(phenylmethylene)-androstane-3,17-diol Diacetate (65)

Compound 64 was dissolved in CH₂Cl₂ (10 mL) and AcOAc (0.14 mL, 1.5 mmol), NEt₃ (0.42 ml, 3.0 mmol) and DMAP (20 mg) were added the reaction was stirred at room temperature for 1 h. Aqueous saturated NaHCO₃ was then added. After 1 h, the product was extracted into CH₂Cl₂ (3×50 mL). The combined extracts were dried and solvents removed to give an oil. The crude product was purified by flash column chromatography (silica gel, eluted with 25-35% EtOAc in hexanes) to give pure product 65 (147 mg, 100%): ¹H NMR (CDCl₃) δ 7.36-7.18 (m, 5H), 6.22 (s, 1H), 5.37 9s, 1H), 5.12 (s, 1H), 4.77 (s, 1H), 4.43 (s, 1H), 2.70 (dd, J=16.8 Hz, 7.0 Hz, 1H), 2.19 (d, J=1.2 Hz, 3H), 2.05 (d, J=1.2 Hz, 3H), 0.76 (s, 3H), 0.69 (s, 3H); ¹³C NMR (CDCl₃) δ 171.1, 170.6, 148.9, 140.6, 137.4, 128.2 (2C), 128.1 (2C), 126.5, 123.7, 106.1, 84.4, 69.5, 54.3, 48.8, 44.4, 43.0, 41.4, 38.0, 36.6, 36.3, 32.2, 30.7, 28.3, 25.6, 21.4, 21.1, 20.5, 12.2, 11.5.

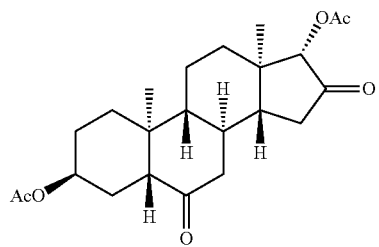

(3β,5β,8α,9β,10α,13α,14β,17α)-3,17-Dihydroxyandrostane-6,16-dione Diacetate (66)

A stream of O₃ was bubbled through a solution of compound 65 (147 mg, 0.36 mmol) dissolved in MeOH/EtOAc (2:1; 20 mL) at −78° C. until a blue color persisted for 10 min. The excess O₃ was purged from the reaction using an O₂ stream as evidenced by the solution becoming colorless. Me₂S was then added (2 mL) and the reaction was allowed to warm to room temperature and then allowed to stir for 14 h. Solvents were removed and the residue was purified by flash column chromatography (silica gel, eluted with 30-40% EtOAc in hexanes) to yield compound 65 as a foamy white solid (106 mg, 85%): 5.10-5.09 (m, 1H), 4.85 (s, br, 1H), 2.14 (s, 3H), 2.02 (s, 3H), 0.81 (s, 3H), 0.76 (s, 3H); ¹³C NMR (CDCl₃) δ 210.0, 209.6, 170.3, 170.2, 85.2, 68.5, 53.4, 52.5, 46.0, 45.6, 41.9, 41.1, 36.4, 35.8, 35.7, 32.0, 25.1, 24.9, 21.4, 20.6, 20.2, 12.4, 12.3.

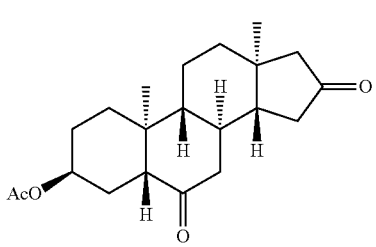

67

(3β,5β,8α,9β,10α,13α,14β)-3-Hydroxyandrostane-6,16-dione Acetate (67)

Freshly prepared Sm filings (1.5 mmol, 225 mg) were added to THF (5 mL) and $I_2$ (1.0 mmol, 254 mg) in THF (5 mL) at room temperature. The suspension was stirred under $N_2$. After 30 min, the mixture became deep blue indicating $SmI_2$ formation and stirring was continued for another 30 min. Compound 66 (106 mg, 0.36 mmol) in THF/MeOH (10/0.2, 10.2 mL) was added. After 1 h, 10% aqueous $Na_2CO_3$ (20 mL) was added and the product was extracted into EtOAc (3×50 mL). The combined extracts were washed with brine (2×20 mL) and dried. The crude product was dissolved in acetone (20 mL) and cooled to 0° C. Jones reagent was added until a brownish orange color persisted for 5 min. After 10 min, 2-propanol (1 mL) and then brine (30 mL) were added. The product was extracted into EtOAc (3×50 mL). Solvents were removed and the residue was purified by flash column chromatography (silica gel, eluted with 30% EtOAc in hexanes) to give product 67 (73 mg, 81%): $^1$H NMR (CDCl$_3$) δ 5.09 (d, J=2.0 Hz, 1H), 2.01 (d, J=2.4 Hz, 3H), 0.87 (s, 3H), 0.76 (s, 3H); $^{13}$C NMR (CDCl$_3$) δ 217.0, 210.5, 170.2, 68.6, 55.5, 53.6, 52.5, 51.8, 46.7, 41.2, 39.3, 38.8, 37.6, 37.0, 32.0, 25.2, 24.9, 21.4, 20.6, 18.0, 12.4.

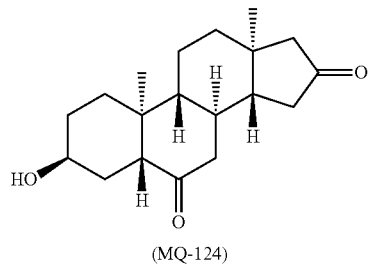

68

(MQ-124)

(3β,5β,8α,9β,10α,13α,14β)-3-Hydroxyandrostane-6,16-dione (68, MQ-124)

To a solution of compound 66 (73 mg, 0.21 mmol) in MeOH (10 mL) was added $K_2CO_3$ (500 mg) at 23° C. The mixture was refluxed for 4 h, MeOH was removed under reduced pressure and the residue was purified by flash column chromatography (silica gel, eluted with 30% EtOAc in hexanes) to give product 68 (61 mg, 95%): mp 205-207° C.; $[α]_D^{23}$ +173.1 (c 0.17, CHCl$_3$); IR $ν_{max}$ 3445, 1741, 1701 cm$^{-1}$; $^1$H NMR (CDCl$_3$) δ 4.15 (s, br, 1H), 2.76-2.73 (m, 1H), 0.87 (s, 3H), 0.75 (d, J=3.9 Hz, 3H); $^{13}$C NMR (CDCl$_3$) δ 217.4, 211.6, 65.1, 55.4, 53.5, 51.7, 51.6, 46.7, 41.5, 39.3, 38.8, 37.6, 37.0, 31.3, 28.0, 27.5, 20.6, 18.0, 12.3.

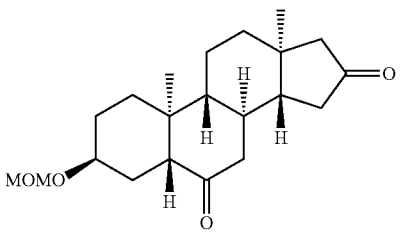

69

(3β,5β,8α,9β,10α,13α,14β)-3-(Methoxymethoxy)-androstane-6,16-dione (69)

Compound 68 (40 mg, 0.13 mmol) was dissolved $CH_2Cl_2$ (10 mL) and cooled to 0° C. (i-Pr)$_2$EtN (0.26 mL, 1.5 mmol) and ClCH$_2$OMe (0.15 ml, 2.0 mmol) were added and the reaction was stirred at room temperature for 6 h. The reaction mixture was made basic by adding aqueous NaHCO$_3$ solution and the product extracted into CH$_2$Cl$_2$. The combined extracts were washed with brine, dried and solvent removed to give a viscous liquid. The crude product was purified by flash column chromatography (silica gel, eluted with 25% EtOAc in hexanes) to give product 69 as a colorless liquid (41 mg, 89%): $^1$H NMR (CDCl$_3$) δ 4.61 (q, J=3.9 Hz, 2H), 3.92 (s, br, 1H), 3.35 (t, J=6.0 Hz, 3H), 2.67 (dd, J=10.2 Hz, 2.4 Hz, 1H), 0.87 (s, 3H), 0.76 (s, 3H); $^{13}$C NMR (CDCl$_3$) δ 217.1, 211.3, 94.4, 70.0, 55.4, 55.2, 53.6, 52.3, 51.8, 46.7, 41.2, 39.3, 38.8, 37.6, 37.0, 31.9, 25.5, 25.3, 20.6, 18.0, 12.5.

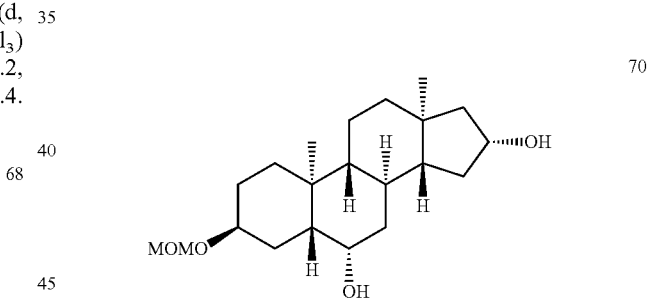

70

(3β,5β,6α,8α,9β,10α,13α,14β,16α)-3-(Methoxymethoxy)-androstane-6,16-diol (70)

Compound 69 (40 mg, 0.12 mmol) was dissolved in stirred EtOH (10 mL) and cooled in an ice-bath. NaBH$_4$ (38 mg, 1.0 mmol) was added in small portions. After 1 h, a solution of water (20 mL) and AcOH (1 mL) was added and the solution was stirred for 1 h. The product was extracted into CH$_2$Cl$_2$ (2×50 mL), washed with an aqueous 1 N HCl, sat. aqueous NaHCO$_3$, brine, dried and the solvent removed. Flash column chromatography (silica gel, eluted with 70% EtOAc in hexanes) gave product 70 (30 mg, 75%): $^1$H NMR (CDCl$_3$) δ 4.67-4.63 (m, 2H), 4.41-4.37 (m, 1H), 3.94 (s, br, 1H), 3.74 (s, br, 1H), 3.38-3.34 (m, 3H), 1.02 (s, 3H), 0.97 (s, 3H); $^{13}$C NMR (CDCl$_3$) δ 94.6, 72.1, 71.9, 71.8, 55.2, 54.3, 53.8, 51.3, 42.3, 40.2, 39.9, 38.9, 37.2, 36.0, 34.5, 30.9, 30.1, 26.3, 20.2, 19.1, 15.1.

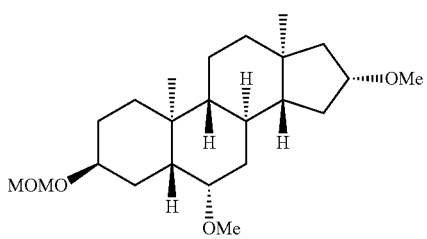

71

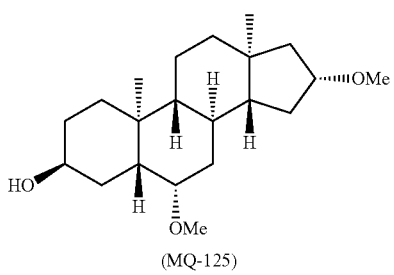

72
(MQ-125)

(3β,5β,6α,8α,9β,10α,13α,14β,16α)-6,16-Dimethoxy-3-(methoxymethoxy)-androstane (71)

To a solution compound 70 (30 mg, 0.09 mmol) in THF (15 mL) was added NaH (80 mg, 60% in mineral oil, 2.0 mmol) at 23° C. The mixture was refluxed for 1 h. Iodomethane (0.5 mL) was added via syringe. The mixture was refluxed for addition 1 h. After cooling, water was slowly added and the product extracted into EtOAc (3×50 mL). The combined extracts were washed with brine, dried and solvent removed to give a viscous liquid. The crude product was purified by flash column chromatography (silica gel, eluted with 25% EtOAc in hexanes) to give product 71 (22 mg, 69%): $^1$H NMR (CDCl$_3$) δ 4.67-4.63 (m, 2H), 3.91 (s, br, 1H), 3.87-3.82 (m, 1H), 3.36 (s, 3H), 3.35 (s, 3H), 3.25 (s, 3H), 3.13 (s, br, 1H), 0.94 (s, 3H), 0.90 (s, 3H); $^{13}$C NMR (CDCl$_3$) δ 94.5, 81.3, 81.1, 72.0, 57.2, 56.7, 55.1, 54.5, 53.1, 47.3, 42.8, 39.9, 39.0, 36.3, 34.4, 34.2, 31.2, 30.4, 29.7, 26.3, 20.3, 18.9, 14.7.

(3β,5β,6α,8α,9β,10α,13α,14β,16α)-6,16-Dimethoxyandrostan3-ol (72, MQ-125)

Compound 71 (22 mg, 0.06 mmol) dissolved in MeOH (10 mL) was stirred with 6 N HCl (10 mL) at room temperature for 6 h. The HCl was neutralized by careful addition of aqueous NaHCO$_3$ solution and the MeOH removed. Water was added and the product was extracted into EtOAc. The combined extracts were washed with brine, dried and the solvents removed to give the crude product as an off-white solid which was purified by flash column chromatography (silica gel, eluted with 40-50% EtOAc in hexanes). Compound 72 was obtained as a white solid (8 mg, 42%): mp 127-129° C.; $[α]_D^{23}$ +44.0 (c 0.05, CHCl$_3$); IR ν$_{max}$ 3401, 1452 cm$^{-1}$; $^1$H NMR (CDCl$_3$) δ 4.14 (s, br, 1H), 3.86-3.84 (m, 1H), 3.26 (d, J=1.6 Hz, 3H), 3.24 (d, J=1.5 Hz, 3H), 3.12 (s, br, 1H), 0.93 (s, 3H), 0.90 (s, 3H); $^{13}$C NMR (CDCl$_3$) δ 81.3, 81.1, 66.8, 57.2, 56.7, 54.5, 53.0, 47.3, 42.1, 39.9, 39.0, 36.5, 34.4, 33.7, 33.3, 30.4, 29.7, 29.1, 20.3, 18.9, 14.5.

Scheme 7

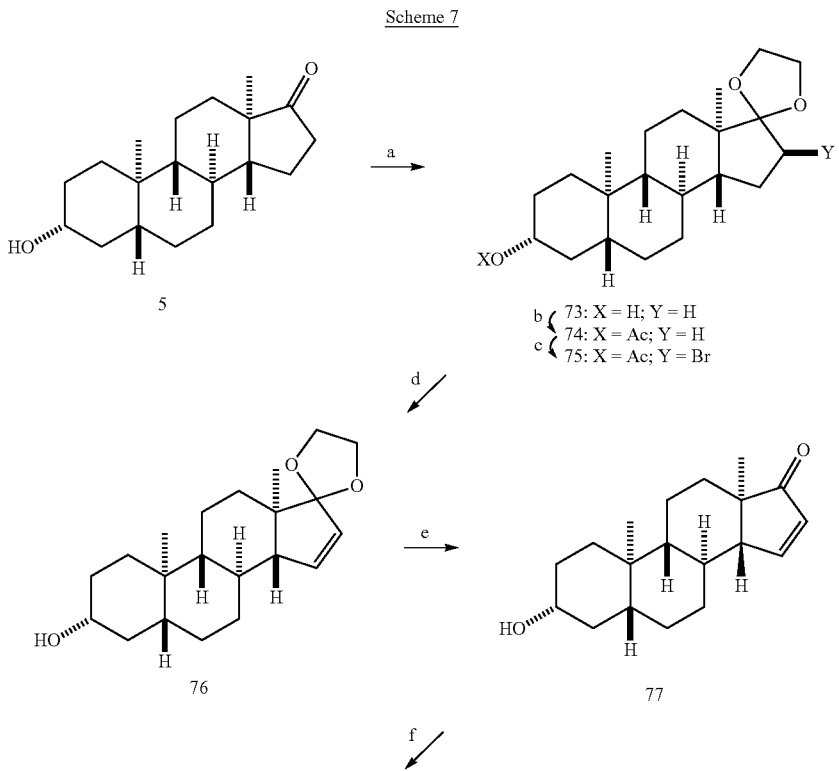

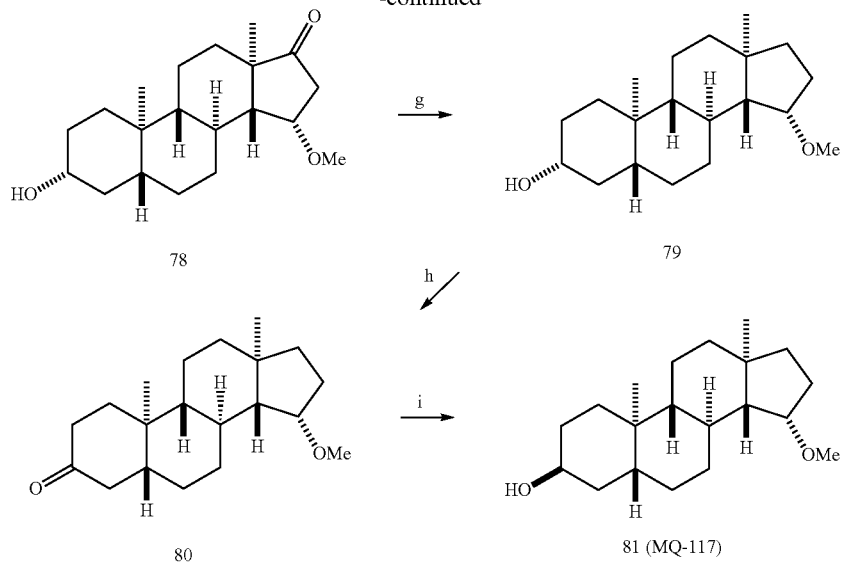

In accordance with Scheme 7, the following compounds were prepared, using methods generally known in the art and as outlined below.

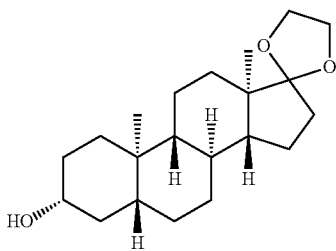

(3α,5β,8α,9β,10α,13α,14β)-3-Hydroxyandrostan-17-one, Cyclic 17-(1,2-ethanediyl Acetal) (73)

To a solution of compound 5 (950 mg, 3.23 mmol) in benzene (150 mL) was added ethylene glycol (2.0 mL) and PTSA (200 mg) at 23° C. The mixture was refluxed in a Dean-Stark apparatus for 16 h. Solvent was removed under reduced pressure and the residue was purified by flash column chromatography (silica gel, eluted with 20% EtOAc in hexanes) to give product 73 (1.08 mg (100%) as a oil: $^1$H NMR (CDCl$_3$) δ 3.92-3.83 (m, 4H), 3.60-3.54 (m, 1H), 0.82 (s, 3H), 0.79 (s, 3H); $^{13}$C NMR (CDCl$_3$) δ 119.4, 71.2, 65.1, 64.5, 54.1, 50.3, 45.9, 44.8, 38.1, 37.0, 35.7, 35.5, 34.1, 31.4, 31.3, 30.7, 28.5, 22.6, 20.6, 14.4, 12.3.

(3α,5β,8α,9β,10α,13α,14β)-3-Hydroxyandrostan-17-one acetate, Cyclic 17-(1,2-ethanediyl Acetal) (74)

Compound 73 (1.08 g, 3.23 mmol) was dissolved stirred in CH$_2$Cl$_2$ (30 mL) and AcOAc (0.7 mL, 7.5 mmol), NEt$_3$ (2.1 ml, 15 mmol) and DMAP (50 mg) were added. After 1 h, aqueous saturated NaHCO$_3$ was then added. After 1 h, the product was extracted into CH$_2$Cl$_2$ (3×50 mL). The combined extracts were dried and solvents removed to give an oil. The crude product was purified by flash column chromatography (silica gel, eluted with 20% EtOAc in hexanes) to give product 74 (1.22 g, 100%): $^1$H NMR (CDCl$_3$) δ 4.68-4.61 (m, 1H), 3.91-3.79 (m, 4H), 1.99 (s, 3H), 0.80 (s, 3H), 0.79 (s, 3H); $^{13}$C NMR (CDCl$_3$) δ 170.6, 119.3, 73.6, 65.1, 64.4, 53.9, 50.2, 45.8, 44.5, 36.7, 35.6, 35.4, 34.1, 33.9, 31.2, 30.6, 28.3, 27.4, 22.6, 21.4, 20.5, 14.3, 12.1.

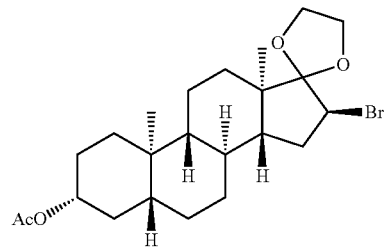

(3α,5β,8α,9β,10α,13α,14β,16α)-16-Bromo-3-hydroxyandrostan-17-one Acetate, Cyclic 17-(1,2-ethanediyl Acetal) (75)

To a solution of the compound 74 (1.22 g, 3.23 mmol) in THF (30 mL) was added pyridinium tribromide (1.55 g, 4.85 mmol) in THF (15 mL) at 0° C. After 1 h, the mixture was warmed to 23° C. After 1 h, aqueous Na$_2$S$_2$O$_3$ (30 ml) was added and the product was extracted into EtOAc (3×100 mL). The combined extracts were dried and solvents removed to give an oil. The crude product was purified by

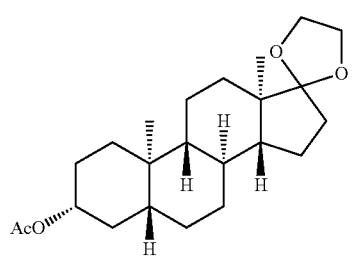

flash column chromatography (silica gel, eluted with 15% EtOAc in hexanes) to give product 75 (1.41 g, 96%): ¹H NMR (CDCl₃) δ 4.67-4.60 (m, 1H), 4.48-4.44 (m, 1H), 4.21-4.05 (m, 2H), 3.93-3.84 (m, 2H), 1.98 (s, 3H), 0.83 (s, 3H), 0.78 (s, 3H); ¹³C NMR (CDCl₃) δ 170.5, 116.7, 73.4, 66.4, 66.0, 55.4, 53.7, 48.2, 45.4, 44.5, 36.5, 35.4, 35.3, 35.1, 33.8, 30.8, 30.4, 28.1, 27.3, 21.4, 20.2, 14.6, 12.1.

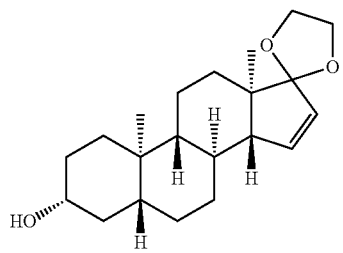

(3α,5β,8α,9β,10α,3α,14β)-3-Hydroxyandrost-15-en-17-one Cyclic 17-(1,2-ethanediyl Acetal) (76)

To a solution of compound 75 (1.40 g, 3.08 mmol) in DMSO (30 mL) was added potassium t-butoxide (414 mg, 3.6 mmol) at 23° C. The mixture was heated to 85° C. for 16 h. After cooling, water (40 mL) was added and the product extracted into EtOAc (3×100 mL). The combined extracts were dried and solvents removed to give product 76 as an oil. The crude product was purified by flash column chromatography (silica gel, eluted with 35% EtOAc in hexanes) to give product 76 (950 mg, 93%): ¹H NMR (CDCl₃) δ 6.14 (d, J=5.8 Hz, 1H), 5.67 (dd, J=5.6 Hz, 3.5 Hz, 1H), 3.97-3.79 (m, 4H), 3.60-3.56 (m, 1H), 2.20-2.16 (m, 1H), 0.90 (s, 3H), 0.83 (s, 3H); ¹³C NMR (CDCl₃) δ 136.5, 131.8, 119.5, 71.1, 65.2, 64.0, 56.3, 54.9, 49.6, 44.9, 38.1, 36.7, 35.6, 32.8, 31.4, 31.3, 29.6, 28.4, 20.3, 16.1, 12.3.

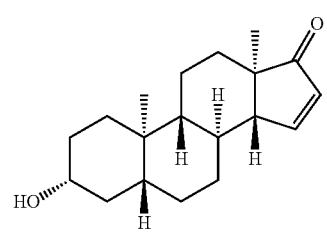

(3α,5β,8α,9β,10α,13α,14β)-3-Hydroxyandrost-15-en-17-one (77)

To a solution of compound 76 (200 mg, 0.60 mmol) in acetone (20 mL) and water (2 mL) was added PTSA (50 mg) at 23° C. After 2 h, NaHCO₃ (400 mg) was added. Solvent was removed and the residue was purified by flash column chromatography (silica gel, eluted with 35% EtOAc in hexanes) to give product 77 (158 mg, 91%): ¹H NMR (CDCl₃) δ 7.49 (d, J=5.9 Hz, 1H), 5.99 (dd, J=5.9 Hz, 3.1 Hz, 1H), 3.59-3.52 (m, 1H), 1.02 (s, 3H), 0.84 (s, 3H); ¹³C NMR (CDCl₃) δ 213.4, 158.7, 131.5, 70.8, 56.8, 55.6, 51.0, 45.0, 37.9, 36.6, 35.8, 32.2, 31.2, 30.7, 29.0, 28.1, 20.6, 20.1, 12.3.

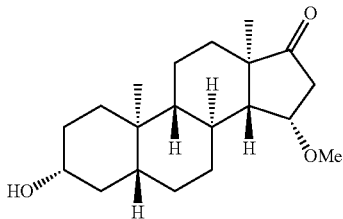

(3α,5β,8α,9β,10α,13α,14β,15α)-3-Hydroxy-15-methxoyandrostan-17-one (78)

To a solution of compound 77 (70 mg, 0.24 mmol) in MeOH was added 4.0 M NaOH (5 mL) (precooled to 0° C.) and H₂O₂ (2.5 mL) at 0° C. After 2 h, the product was extracted into EtOAc (3×100 mL) and the combined extracts were washed with brine (3×50 mL). The combined extracts were dried and solvents removed to give an oil. The oil was purified by flash column chromatography (silica gel, eluted with 40% EtOAc in hexanes) to give product 78 (60 mg, 77%): ¹H NMR (CDCl₃) δ 4.11-3.90 (m, 1H), 3.62-3.54 (m, 1H), 3.23 (s, 3H), 2.64 (d, J=19.2 Hz, 1H), 2.29 (dd, J=19.2 Hz, 6.3 Hz, 1H), 1.08 (s, 3H), 0.85 (s, 3H); ¹³C NMR (CDCl₃) δ 220.2, 76.5, 71.1, 56.9, 55.5, 54.9, 47.1, 45.0, 42.4, 38.1, 36.9, 35.7, 32.7, 31.5, 31.4, 30.3, 28.3, 20.5, 17.4, 12.3.

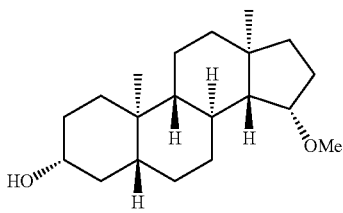

(3α,5β,8α,9β,10α,13α,14β,15α)-15-Methxoyandrostan-3-ol (79)

To compound 78 (60 mg, 0.19 mmol) in MeOH/CH₂Cl₂ (3:1, 20 mL) was added zinc dust (1.3 g, 20 mmol) and dropwise TMSCl (2.54 mL, 20 mmol) at 0° C. After 2 h, NaHCO₃ (2.02 g, 24 mmol) was added. After stirring for 5 min, the mixture was filtered and the filtrate was concentrated. The residue was purified by flash column chromatography (silica gel, eluted with 30% EtOAc in hexanes) to give product 79 (36 mg, 63%): 3.69-3.66 (m, 1H), 3.61-3.55 (m, 1H), 3.19 (s, 3H), 0.92 (s, 3H), 0.83 (s, 3H); ¹³C NMR (CDCl₃) δ 81.7, 71.4, 59.2, 56.3, 55.2, 45.1, 40.6, 40.3, 40.1, 38.3, 37.1, 35.7, 32.2, 31.5, 31.3, 29.8, 28.6, 21.3, 19.5, 12.4.

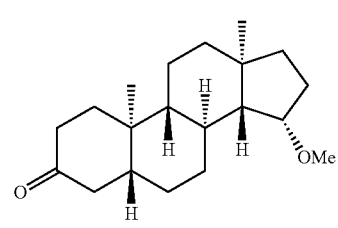

71

(5β,8α,9β,10α,13α,14β,15α)-15-Methxoyandrostan-3-one (80)

To a solution of compound 79 (36 mg, 0.12 mmol) in CH₂Cl₂ (10 mL) was added Dess-Martin periodinane (424 mg, 1.0 mmol). After 1 h, water (20 mL) was added and the product extracted into CH₂Cl₂ (3×50 mL). The combined extracts were dried and solvents removed to give an oil. The oil was purified by flash column chromatography (silica gel, eluted with 25% EtOAc in hexanes) to give product 80 (29 mg, 80%): ¹H NMR (CDCl₃) δ 3.70-3.67 (m, 1H), 3.19 (s, 3H), 1.03 (s, 3H), 0.94 (s, 3H); ¹³C NMR (CDCl₃) δ 212.3, 81.6, 59.0, 56.3, 54.5, 46.9, 44.8, 40.6, 40.3, 40.0, 38.7, 38.2, 35.9, 32.1, 30.9, 29.8, 28.8, 21.4, 19.5, 11.5.

72

(3β,5β,8α,9β,10α,13α,14β,15α)-15-Methxoyandrostan-3-ol (81, MQ-117)

K-Selectride (1M in THF, 0.50 mL) was added dropwise under N₂ to a cooled solution (−78° C.) of compound 80 (29 mg, 0.095 mmol) in anhydrous THF (10 mL). After 2 hr stirring at −78° C., water (2 mL) was added and the reaction was allowed to reach room temperature. Then, aqueous NaOH (2 mL, 3 M), and 30% H₂O₂ (2 mL) were added and the reaction was stirred for 30 min. The product was extracted into CH₂Cl₂ (2×50 mL), the combined extracts were washed with aqueous HCl (1 N), saturated aqueous NaHCO₃, and brine and the solvent removed. Flash column chromatography (silica gel, eluted with 10% EtOAc in hexanes) gave product 81 (MQ-117, 22 mg, 75%) as a white solid: mp 137-139° C. (EtOAc/hexanes); [α]$_D^{23}$ +32 (c 0.10, CHCl₃). IR ν$_{max}$ 3341, 2927, 1451 cm⁻¹; ¹H NMR (CDCl₃) δ 4.04 (s, br, 1H), 3.70-3.68 (m, 1H), 3.19 (s, 3H), 0.92 (s, 3H), 0.80 (s, 3H); ¹³C NMR (CDCl₃) δ 81.7, 66.6, 59.3, 56.3, 55.1, 40.6, 40.3, 40.1, 39.3, 36.3, 35.9, 32.3, 32.2, 31.3, 29.8, 29.0, 28.5, 20.8, 19.6, 11.2. Anal. (C₂₀H₃₄O₂) C, 78.38, H, 11.18. found C, 78.50, H, 11.42.

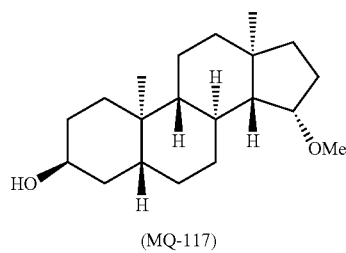

(MQ-117)

Scheme 8

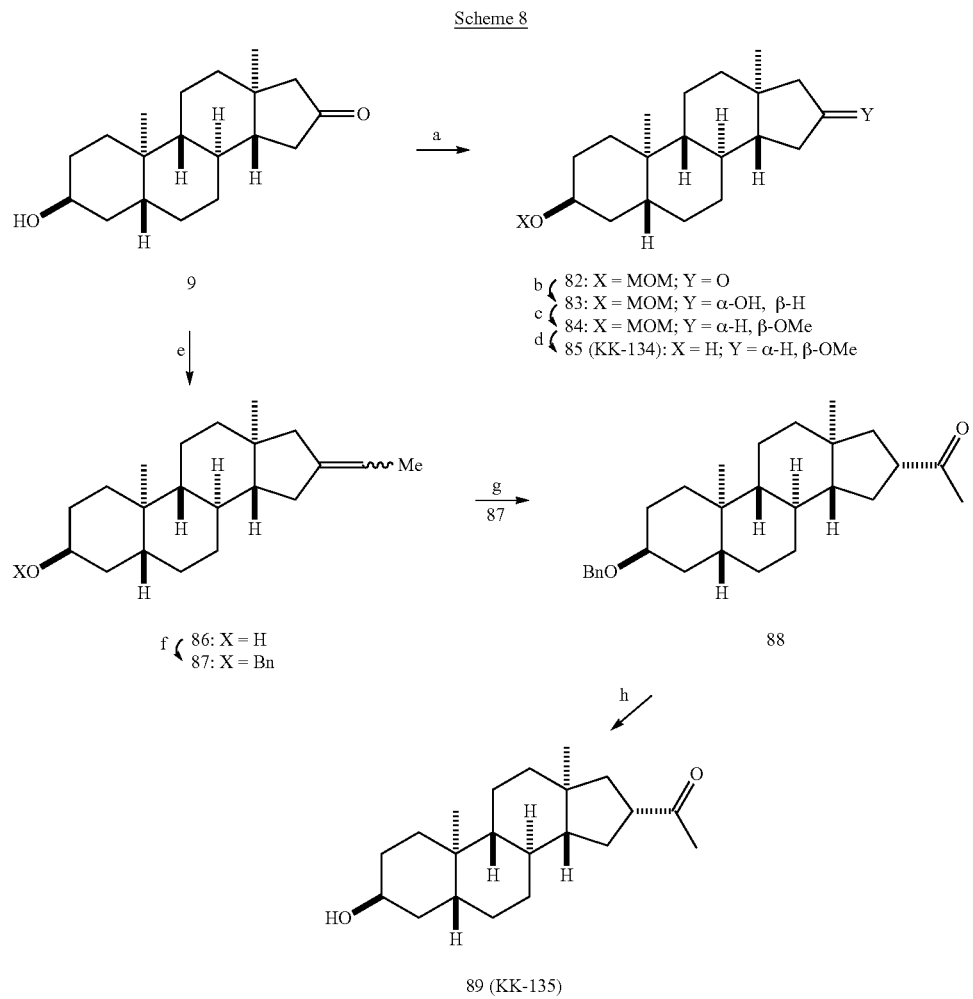

In accordance with Scheme 8, the following compounds were prepared, using methods generally known in the art and as outlined below.

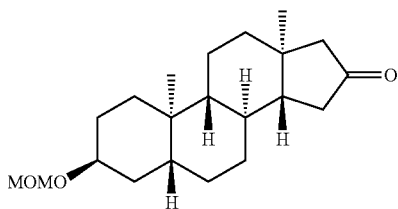

82

(3β,5β,8α,9β,10α,13α,14β)-3-(Methoxymethoxy)androstan-16-one (82)

To a cold (0° C.) stirred solution of compound 9 (145 mg, 0.5 mmol) in CH$_2$Cl$_2$ (5 mL) were added N,N-Diisopropyl ethyl amine (0.52, mL, 3 mmol) and chloromethyl methyl ether (0.15 mL, 2 mmol) and the reaction was slowly brought to room temperature and allowed to stir at room temperature for another 16 h. Aqueous saturated NaHCO$_3$ was added and the product was extracted into CH$_2$Cl$_2$ (3×75 mL). The combined organic extracts were washed with brine, dried and concentrated to give an oil which was purified by flash column chromatography (silica gel, eluted with 15-20% EtOAc in hexanes) to give product 82 as a white solid (159 mg, 95%): mp 126-128° C.; IR ν$_{max}$ 2934, 2845, 1742, 1438, 1385 cm$^{-1}$; $^1$H NMR δ 4.64 (s, 2H), 3.82 (s, 1H), 3.35 (s, 3H), 2.30 (m, 2H), 0.85 (s, 3H), 0.81 (s, 3H); $^{13}$C NMR δ 218.8, 94.5, 71.4, 55.8, 55.1, 54.2, 51.7, 39.6, 39.2, 39.1, 38.2, 36.0, 34.8, 33.54, 32.5, 32.2, 28.3, 26.2, 20.3, 18.1, 11.3.

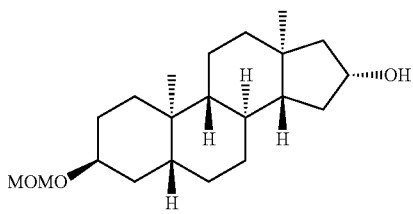

83

(3β,5β,8α,9β,10α,13α,14β,16α)-3-(Methoxymethoxy)androstan-16-ol (83)

To a cold (0° C.) solution of compound 82 (130 mg, 0.39 mmol) dissolved in stirred EtOH (5 mL), was added NaBH$_4$ (38 mg, 1 mmol) and the mixture was warmed to room temperature and stirred for 4 h. Water (70 mL) was added and the product was extracted into CH$_2$Cl$_2$ (3×50 mL). The combined organic extracts were washed with brine, dried and concentrated to give an oil. The oil was purified by flash column chromatography (silica gel, eluted with 10-25% EtOAc in hexanes) to give product 83 (110 mg, 85%): mp 82-84° C.; IR ν$_{max}$ 3401, 2928, 1447, 1378 cm$^{-1}$; $^1$H NMR δ 4.64 (s, 2H), 4.34 (m, 1H), 3.82 (s, 1H), 3.35 (s, 3H), 2.16 (m, 1H), 0.93 (s, 3H), 0.79 (s, 3H); $^{13}$C NMR δ 94.4, 71.9, 71.6, 55.1, 54.3, 54.0, 51.3, 40.1, 39.7, 39.0, 37.1, 35.9, 35.2, 33.6, 32.7, 32.2, 28.5, 26.2, 20.4, 19.1, 11.4.

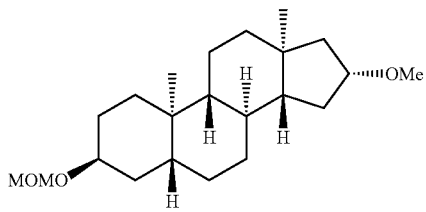

84

(3β,5β,8α,9β,10α,13α,14β,16α)-16-Methoxy-3-(Methoxymethoxy)androstane (84)

A mixture of KH (50 wt % in paraffin, 160 mg, 2 mmol), compound 83 (80 mg, 0.24 mmol)) and THF was refluxed for 2 hours under an N$_2$ atmosphere. The reaction was brought to room temperature and a large excess of MeI (5 mL) was added, and the mixture was heated at 50° C. for 16 h. The reaction was cooled, the excess hydride was quenched carefully with 2-propanol and water was added. The product was extracted into EtOAc and the combined extracts were washed with brine, dried and concentrated to give an oil. The oil was purified by column chromatography (silica gel, eluted with 2-10% EtOAc in hexanes) to give product 84 (65 mg, 77%) as a low-melting white solid: mp 67-69° C.; IR ν$_{max}$ 2920, 1447, 1378, 1221 cm$^{-1}$; $^1$H NMR δ 4.41 (s, 2H), 3.82 (b s, 2H), 3.35 (s, 3H), 3.23 (s, 3H), 0.85 (s, 3H), 0.78 (s, 3H); $^{13}$C NMR δ 94.4, 81.1, 71.6, 56.6, 55.1, 54.4, 53.3, 47.3, 39.8, 39.7, 39.1, 35.9, 35.2, 34.1, 33.6, 32.8, 32.2, 28.5, 26.3, 20.5, 18.8, 11.3.

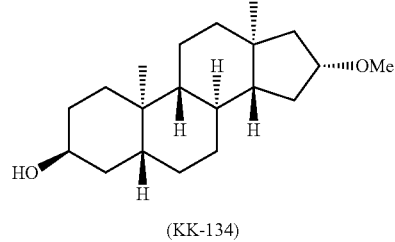

85

(KK-134)

(3β,5β,8α,9β,10α,13α,14β,16α)-16-Methoxyandrostan-3-ol (85, KK-134)

To a methanolic solution (7 mL) of compound 84 (50 mg, 0.14 mmol) in stirred MeOH (7 mL) was added a dry HCl solution (~4 N) in MeOH (5 mL) and the mixture was stirred at room temperature for 17 h. The reaction was made alkaline by adding aqueous saturated NaHCO$_3$ and the product was extracted into CH$_2$Cl$_2$. The combined extracts were dried and concentrated to give crude product as an off-white solid which was purified by flash column chromatography (silica gel, eluted with 20-35% EtOAc in hexanes) to give product 85 (KK-134) (35 mg, 81%) as a colorless solid: mp 169-171° C.; [α]$_D$=+1.4 (c 0.14 CHCl$_3$); IR ν$_{max}$ 3451, 2918, 1432, 1378, 1246 cm$^{-1}$; $^1$H NMR δ 4.04 (s, 1H), 3.83 (m, 1H), 3.24 (s, 3H), 1.68 (m, 1H), 0.87 (s, 3H), 0.78 (s, 3H); $^{13}$C NMR δ 81.2, 66.5, 56.6, 54.4, 53.3, 47.2, 39.8, 39.1 (2×C), 36.2, 35.8, 35.2, 34.1, 32.2, 32.1, 29.0, 28.5, 20.5, 18.8, 11.2. Anal. (C$_{20}$H$_{34}$O$_2$): C, 78.38%; H, 11.18%. Found: C, 78.46%; H, 11.30%.

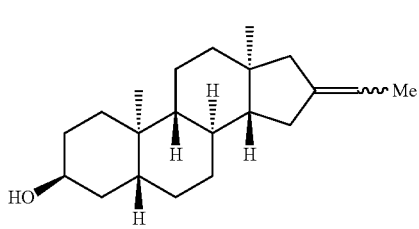

(3β,5β,8α,9β,10α,13α,14β)-16-Ethylidene-androstan-3-ol (86)

To a suspension of ethyltriphenylphosphonium bromide (1.85 g, 5 mmol) in THF (15 mL) was added potassium t-butoxide in t-butyl alcohol (194 mg potassium dissolved in 7.8 mL of t-butyl alcohol) and the resulting solution was heated at reflux for 30 min. The solution became bright orange. Compound 85 (174 mg, 0.6 mmol) in THF (5 mL) was added and the reaction was refluxed for 2 h. The reaction was cooled, water was added the product was extracted into EtOAc (3×80 mL). The combined organic extracts were washed with brine, dried and solvent evaporated to give an off-white solid. The crude product was purified by flash column chromatography (silica gel, eluted with 25% EtOAc in hexanes) to yield product 86 (160 mg, 88%) as a solid which was a mixture of the E/Z 16-ethylidenes: IR $v_{max}$ 3293, 2926, 2849, 1448, 1377 cm$^{-1}$; $^1$H NMR δ 5.31 (b s, 1H), 4.05 (s, 1H), 0.80 (s, 3H), 0.73 & 0.71 (s, 3H); $^{13}$C NMR δ 141.9, 116.9, 116.2, 66.6, 54.5, 54.4, 5.7, 49.4, 45.1, 40.1, 39.1, 38.7, 38.4, 36.2, 35.9, 35.3, 33.6, 32.2, 32.1, 29.8, 29.0, 28.5, 20.8, 20.7, 18.2, 17.5, 14.6, 11.2.

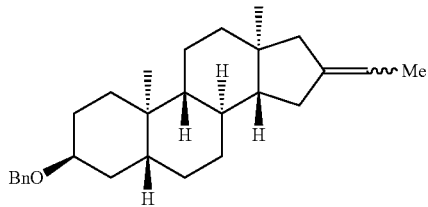

(3β,5β,8α,9β,10α,13α,14β)-3-Benzyloxy-16-Ethylidene-androstane (87)

A stirred 60% suspension of sodium hydride (200 mg, 5 mmol) in mineral oil, compound 86 (151 mg, 0.5 mmol) and benzyl bromide (0.59 ml, 5 mmol) in THF (20 mL) was heated at reflux for 6 h. The reaction was cooled, aqueous saturated ammonium chloride was added and the product was extracted into EtOAc (3×60 mL). The combined extracts were washed with brine, dried and concentrated to give an oil. The oil was purified by flash column chromatography (silica gel, eluted with 2-5% EtOAc in hexanes). After purification, product 87 contained benzyl bromide which was removed by heating the isolated product at 160° C. under high vacuum to give product 87 (a mixture of the E/Z 16-ethylidenes, 157 mg, 80%) as a colorless oil: IR $v_{max}$ 2926, 2853, 1453, 1359 cm$^{-1}$; $^1$H NMR δ 7.30-7.18 (m, 5H), 5.23 (b s, 1H), 4.43 (apparent q, 2H, J=12.5 Hz), 0.74 (s, 3H), 0.66 & 0.64 (s, 3H); $^{13}$C NMR δ 142.0, 139.5, 128.3, 127.4, 127.2, 116.4, 116.1, 73.3, 69.6, 54.4, 53.7, 49.5, 45.1, 40.1, 39.6, 38.8, 38.4, 36.1, 35.5, 35.4, 33.7, 33.1, 32.74, 32.74, 32.2, 29.9, 29.7, 28.6, 25.7, 20.82, 20.76, 18.2, 17.5, 14.6, 11.5.

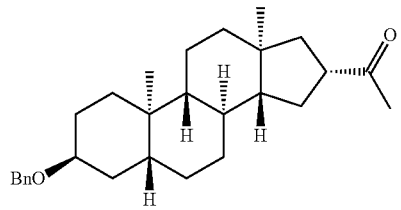

(3β,5β,8α,9β,10α,13α,14β,16α)-16-Acetyl-3-benzyloxyandrostane (88)

To an ice-cold solution of product 87 (130 mg, 0.33 mmol) in THF, was added a 1M solution of BH$_3$.THF complex (1 mL, 1 mmol) and the reaction was stirred at 0° C. for 90 minutes. To this cold solution, were slowly added (in drops) 5 N aqueous NaOH (5 mL) and 30% H$_2$O$_2$ (5 mL) and stirring was continued at room temperature for 90 min. Water was added and the product extracted into EtOAc (3×70 mL). The combined organic extracts were washed with brine, dried and solvent were removed to give a crude hydroboration alcohol product (not characterized) that was dissolved in acetone (8 mL) and cooled to 0° C. Jones reagent was added drop wise until an orange color persisted. After 5 min, the excess Jones reagent was consumed by adding few drops of 2-isopropanol. Water was added and the product extracted into EtOAc (3×60 mL). The combined organic extracts were washed with brine, dried and the solvent removed to give an oil. The oil was purified by flash column chromatography (silica gel, eluted 50% CH$_2$Cl$_2$ in hexanes) to give product 88 (90 mg, 68%): mp: 135-138° C.; IR $v_{max}$ 2927, 2852, 1710, 1496, 1453, 1379, 1359, 1208 cm$^{-1}$; $^1$H NMR δ 7.30-7.15 (m, 5H), 4.43 (apparent q, 2H, J=11.1 Hz), 3.57 (s, 1H), 2.87 (m, 1H), 2.08 (s, 3H), 0.72 (s, 3H), 0.57 (s, 3H); $^{13}$C NMR δ 210.7, 139.4, 128.3, 127.3 (2×C), 127.2 (2×C), 73.2, 69.6, 54.9, 54.2, 49.4, 41.6, 40.8, 39.5, 38.9, 36.0, 35.3, 33.1, 32.8, 32.2, 29.1, 28.8, 28.5, 25.6, 20.7, 18.3, 11.4.

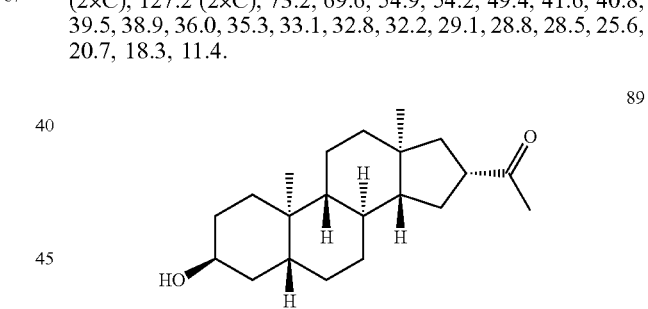

KK-135

(3β,5β,8α,9β,10α,13α,14β,16α)-16-Acetylandrostan-3-ol (89, KK-135)

Compound 88 (40 mg, 0.98 mmol) dissolved in EtOAc (15 mL) and Pd/C (100 mg) was subjected to hydrogenolysis in a Parr Hydrogenator (H$_2$, 65 psi) for 3 days. The Pd/C was removed on a short silica gel column using EtOAc as eluent and the solvent removed. The crude product was purified by flash column chromatography (silica gel, eluted with 30-40% EtOAc in hexanes) to give product 89 (KK-135, 25 mg, 81%) as a white solid: mp 169-172° C.; $[α]_D^{23}$=+18.6 (c 0.07, CHCl$_3$); IR $v_{max}$ 3486, 2928, 1688, 1452, 1367, 1264, 1206 cm$^{-1}$; $^1$H NMR δ 4.04 (d, 1H, J=2.8 Hz), 2.92 (m, 1H), 2.15 (s, 3H), 0.77 (s, 3H), 0.64 (s, 3H); $^{13}$C NMR δ 210.6, 66.5, 54.8, 54.3, 49.4, 41.6, 40.8, 39.1, 38.9, 36.2, 35.8, 35.2, 32.3, 32.2, 29.1, 29.0, 28.8, 28.4, 20.7, 18.3, 11.2. Anal. (C$_{21}$H$_{34}$O$_2$): C, 79.19%; H, 10.76%. Found: C, 79.09%; H, Scheme 9

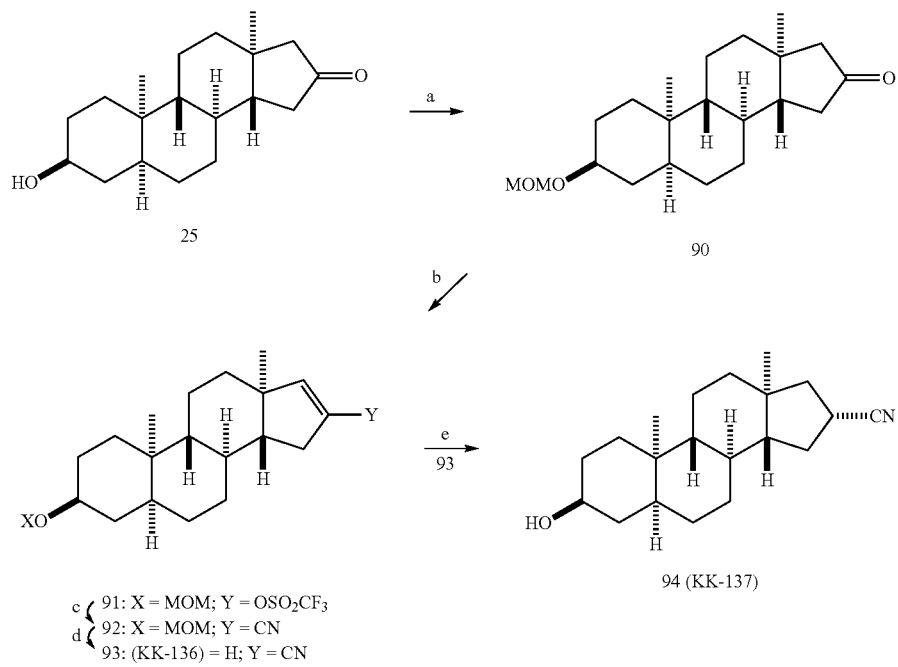

In accordance with Scheme 9, the following compounds were prepared, using methods generally known in the art and as outlined below.

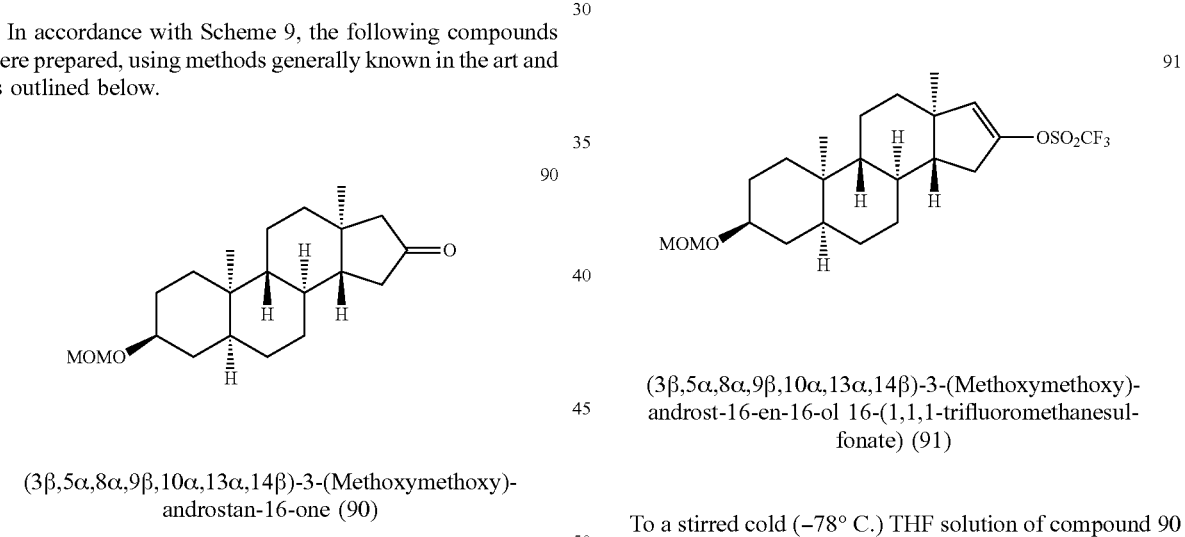

(3β,5α,8α,9β,10α,13α,14β)-3-(Methoxymethoxy)-androstan-16-one (90)

To a stirred cold (0° C.) solution of compound 25 (145 mg, 0.5 mmol) in $CH_2Cl_2$ (5 mL) were added N,N-diisopropyl ethyl amine (0.52, mL, 3 mmol) and chloromethyl methyl ether (0.15 mL, 2 mmol) and the reaction was slowly brought to room temperature and allowed to stir for 16 h. Saturated aqueous $NaHCO_3$ was added and the product extracted into $CH_2Cl_2$ (3×75 mL). The combined organic extracts were washed with brine, dried and concentrated to give an oil which was purified by flash column chromatography (silica gel, eluted with 15-20% EtOAc in hexanes) to give product 90 (150 mg, 90%) as a white solid: mp 108-110° C.; IR $v_{max}$ 2581, 2930, 2884, 1735, 1449, 1410 cm$^{-1}$; $^1$H NMR (CDCl$_3$) δ 4.66 (s, 2H), 3.52 (m, 1H), 3.34 (s, 3H), 0.93 (s, 3H), 0.83 (s, 3H); $^{13}$C NMR (CDCl$_3$) δ 218.6, 94.5, 76.6, 55.8, 55.1, 51.6, 41.8, 40.4, 39.2, 39.1, 38.3, 35.2, 35.0, 34.8, 33.4, 27.6, 26.9, 26.6, 23.2, 20.2, 18.0.

(3β,5α,8α,9β,10α,13α,14β)-3-(Methoxymethoxy)-androst-16-en-16-ol 16-(1,1,1-trifluoromethanesulfonate) (91)

To a stirred cold (−78° C.) THF solution of compound 90 (130 mg, 0.39 mmol) and N-phenyl bis(trifluoromethanesulfonimide) (357 mg, 1 mmol) was added potassium hexamethyldisilazide (0.5 M in toluene, 2 mL, 1 mmol) and the mixture was slowly warmed to room temperature and stirred for 15 h. Water was added and the product extracted into EtOAc (3×70 mL). The combined extracts were washed with brine, dried and solvents removed to give a yellow oil. The crude product was purified by flash column chromatography (silica gel, eluted with 2-3% EtOAc in hexanes) to give product 91 (150 mg, 83%) as a colorless oil: IR $v_{max}$ 2934, 1634, 1423, 1376, 1293, 1245, 1211, cm$^{-1}$; $^1$H NMR (CDCl$_3$) δ 5.69 (d, 1H, J=1.6 Hz), 4.68 (s, 2H), 3.53 (m, 1H), 3.37 (s, 3H), 2.30 (m, 2H), 0.94 (s, 3H), 0.89 (s, 3H); $^{13}$C NMR (CDCl$_3$) δ 150.5, 129.3, 118.5 (q), 94.6, 76.6, 75.3, 55.1, 54.6, 44.0, 41.9, 40.7, 35.5, 34.99, 34.96, 33.7, 33.5, 32.2, 27.6, 26.9, 26.2, 23.2, 20.1, 16.9.

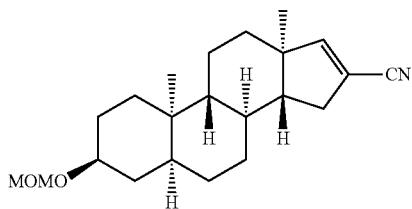

(3β,5α,8α,9β,10α,13α,14β)-3-(Methoxymethoxy)-androst-16-en-16-carbonitrile (92)

Compound 91 (116 mg, 0.25 mol) was dissolved in acetonitrile (15 mL), copper(I)iodide (15 mg) and sodium cyanide (50 mg) were added and the solvent was refluxed under $N_2$. While refluxing, tertakis(triphenylphosphine)palladium (35 mg) was added and reflux was continued for 2 h. The reaction was cooled and aqueous $NaHCO_3$ solution was added. From the biphasic solution, the product was extracted into EtOAc and the extracts were washed with brine, dried and the solvents removed. The crude product was purified by flash column chromatography (silica gel, eluted with 5-15% EtOAc in hexanes) to give product 92 (60 mg, 72%) as a white solid: mp 97-99° C.; IR $v_{max}$ 2931, 2864, 2218, 1589, 1452, 1374, 1262, 1212 cm$^{-1}$; $^1$H NMR (CDCl$_3$) δ 6.71 (d, 1H, J=1.6 Hz), 4.68 (s, 2H), 3.53 (m, 1H), 3.36 (s, 3H), 2.38 (dd, 1H, J=14.9 Hz, 6.3 Hz), 2.21 (m, 1H), 0.94 (s, 3H), 0.81 (s, 3H); $^{13}$C NMR (CDCl$_3$) δ 160.2, 117.4, 113.3, 94.5, 76.6, 55.6, 55.1, 47.5, 41.9, 40.8, 36.2, 34.9, 34.7, 34.5. 34.2, 33.5, 27.6, 26.9, 26.3, 23.2, 20.3, 15.8.

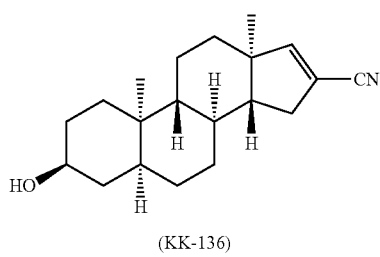

(KK-136)

(3β,5α,8α,9β,10α,13α,14β)-3-Hydroxyandrost-16-ene-16-carbonitrile (93, KK-136)

To compound 92 (50 mg, 0.15 mmol) dissolved in MeOH (5 mL) was added a dry HCl solution (~4 N) in MeOH (4 ml) and the reaction was stirred at room temperature for 2 h. The reaction was made basic by adding aqueous saturated NaHCO$_3$ and the product was extracted into CH$_2$Cl$_2$. The CH$_2$Cl$_2$ was dried and removed to give crude product 93 as an off-white solid which was purified by flash column chromatography (silica gel, eluted with 40% EtOAc in hexanes) to give product 93 (40 mg, 93%) as a white solid: mp 195-197° C.; [α]$_D^{23}$ +11.6 (c 0.06, CHCl$_3$); IR $v_{max}$ 3391, 2928, 2860, 2219, 1589, 1453, 1373, 1263 cm$^{-1}$; $^1$H NMR (CDCl$_3$) δ 6.73 (d, 1H, J=1.6 Hz), 3.64 (m, 1H), 2.40 (m, 1H), 2.23 (m, 1H), 0.96 (s, 3H), 0.83 (s, 3H); $^{13}$C NMR (CDCl$_3$) δ 160.2, 117.5, 113.3, 71.6, 55.6, 47.6, 41.9, 40.8, 36.4, 35.2, 34.8, 34.3, 30.4, 26.9, 26.3, 23.2, 20.3, 15.8. Anal. (C$_{20}$H$_{29}$NO): C, 80.21%; H, 9.76%; N, 4.68%. Found: C, 79.88%; H, 9.96%; N, 4.67%.

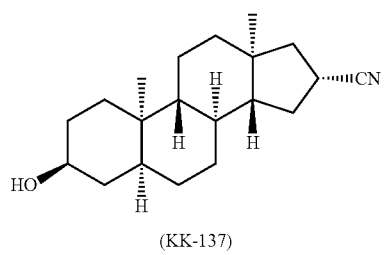

(KK-137)

(3β,5α,8α,9β,10α,13α,14β,16α)-3-Hydroxyandrost-16-carbonitrile (94, KK-137)

Compound 93 (85 mg) and 10% Pd—C (70 mg) in EtOAc (30 mL) was hydrogenated in a Parr Hydrogenation apparatus at (H$_2$, 60 psi) for 15 h. The reaction was passed through a short silica gel column using 50% EtOAc in hexanes as eluent to give an off-white solid product. Recrystallization from diethyl ether gave product 94 (KK-137, 80 mg, 94%) as a white solid: mp 155-157° C.; [α]$_D^{23}$ +19 (c 0.1, CHCl$_3$); IR $v_{max}$ 3400, 2930, 2862, 2234, 1450, 1382 cm$^{-1}$; $^1$H NMR (CDCl$_3$) δ 3.61 (m, 1H), 2.83 (m, 1H), 2.18 (m, 1H), 0.92 (s, 3H), 0.89 (s, 3H); $^{13}$C NMR (CDCl$_3$) δ 124.7, 71.5, 54.5, 45.1, 41.7, 41.6, 40.3, 38.3, 36.1, 35.6, 35.3, 34.5, 32.2, 30.3, 26.8, 26.6, 23.2 (2×C), 20.3, 18.1. Anal. (C$_{20}$H$_{31}$NO): C, 79.68%; H, 10.36%; N, 4.65. Found: C, 79.42%; H, 10.54%; N, 4.60%.

Scheme 10

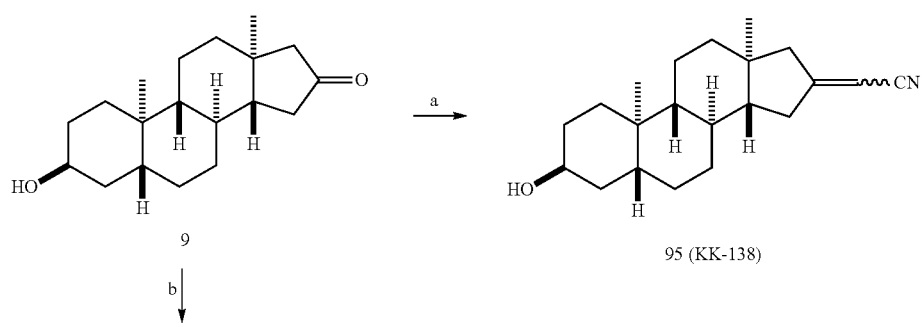

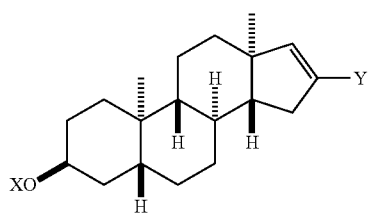

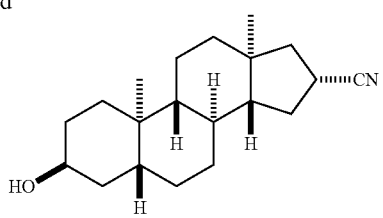

c { 96: X = MOM; Y = OSO₂CF₃
d { 97: X = MOM; Y = CN
   98: (KK-141): X = H; Y = CN 99 (KK-142)

In accordance with Scheme 10, the following compounds were prepared, using methods generally known in the art and as outlined below.

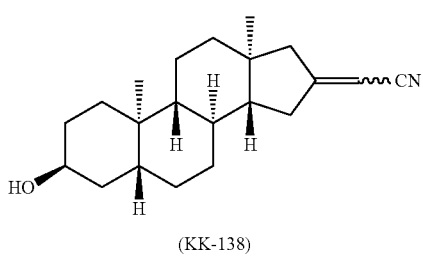

(KK-138)

2-[(3β,5β,8α,9β,10α,13α,14β)-3-Hydroxyandrostan-16-ylidene]-acetonitrile (95, KK-138)

To a suspension of NaH (60% dispersion in mineral oil, 200 mg, 5 mmol) in dry THF (5 mL) at 0° C. under N₂, diethyl(cyanomethyl)phosphonate (0.83 mL, 5.13 mmol) was added dropwise. After disappearance of the solid sodium hydride, compound 29 (145 mg, 0.5 mmol) in dry THF (10 mL) was added. The reaction was allowed to warm to room temperature and stirred for 15 h at room temperature. Aqueous NaHCO₃ was added and the product extracted into EtOAc. The EtOAc was washed with brine, dried and the solvent removed. The residue was purified by flash column chromatography (silica gel eluted with 20-35% EtOAc in hexanes) to give product 95 as an inseparable mixture of E/Z nitriles (136 mg 87%): mp. 162-172° C.; IR $v_{max}$ 3368, 2928, 2850, 2217, 1638, 1449, 1381, 1265 cm⁻¹; ¹H NMR (CDCl₃) δ 5.26 (br s, 1H), 4.06 (br s, 1H), 2.80-2.04 (m, 4H), 0.80 (s, 3H), 0.76 & 0.75 (s, 3H); ¹³C NMR (CDCl₃) δ 172.6, 172.4, 117.3, 117.2, 92.6, 92.5, 66.4, 54.22, 54.17, 53.8, 53.5, 49.3, 41.3, 40.9, 39.0, 38.0, 36.2, 35.81, 35.75, 35.2, 34.7, 34.08, 32.04, 29.0, 28.9, 28.3, 20.5, 17.8, 17.6, 11.17, 11.15. Anal. (C₂₁H₃₁NO): C, 80.46%; H, 9.97%; N, 4.47%. Found: C, 80.81%; H, 10.28%; N, 4.52%.

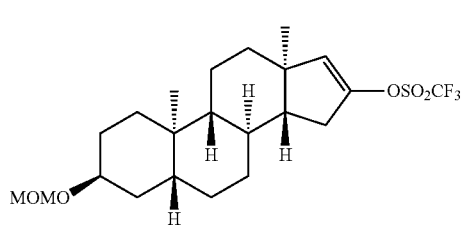

(3β,5β,8α,9β,10α,13α,14β)-3-(Methoxymethoxy)-androst-16-en-16-ol 16-(1,1,1-trifluoromethanesulfonate) (96)

Compound 96 (252 mg, 98%) was prepared as an oil from compound 9 using the procedure described for the preparation of compound 91. Compound 96 had: ¹H NMR (CDCl₃) δ 5.67 (d, 1H, J=1.5 Hz), 4.64 (apparent q, 2H, J=6.6 Hz), 3.81 (m, 1H), 3.35 (s, 3H), 2.33 (m, 2H), 0.88 (s, 3H), 0.80 (s, 3H); ¹³C NMR (CDCl₃) δ 150.6, 129.3, 118.5 (q), 94.5, 71.4, 55.0, 54.5, 54.4, 43.9, 39.8, 36.1, 35.3, 33.5, 33.3, 32.4, 32.2, 31.6, 28.2, 26.2, 20.2, 16.9, 11.2.

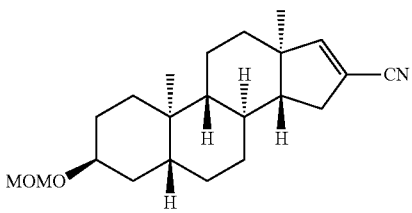

(3β,5β,8α,9β,10α,13α,14β)-3-(Methoxymethoxy)-androst-16-en-16-carbonitrile (97)

Compound 97 (140 mg, 98%) was prepared as an oil from compound 96 using the procedure described for the preparation of compound 92. Compound 97 had: IR $v_{max}$ 2932, 2858, 2218, 1588, 1454, 1373, 1237, 1216 cm⁻¹; ¹H NMR (CDCl₃) δ 6.69 (d, 1H, J=1.5 Hz), 4.62 (2H, apparent q, J=7.1 Hz), 3.81 (br s, 1H), 3.34 (s, 3H), 2.40-2.10 (m, 2H), 0.81 (s, 3H), 0.77 (s, 3H); ¹³C NMR (CDCl₃) δ 160.1, 117.4, 113.2, 94.4, 71.3, 55.6, 55.0, 54.4, 47.4, 39.7, 36.0, 34.5, 34.4, 33.7, 33.5, 32.5, 31.6, 28.2, 26.2, 20.2, 15.8, 11.2.

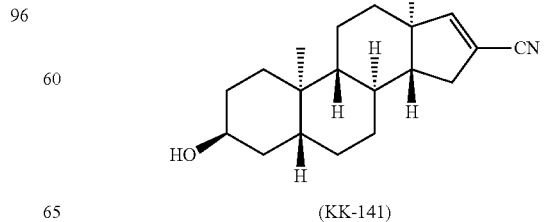

(KK-141)

(3β,5β,8α,9β,10α,13α,14β)-3-Hydroxyandrost-16-ene-16-carbonitrile (98, KK-141)

Compound 98 (100 mg, 98%) was prepared as a white solid from compound 97 using the procedure described for the preparation of compound 93. Compound 98 had: mp 247-249° C.; $[\alpha]_D^{23}$ +14.6 (c 0.07, CHCl$_3$); IR $\nu_{max}$ 3484, 2934, 2915, 2857, 2220, 1588, 1452, 1371, 1355, 1247 cm$^{-1}$; $^1$H NMR (CDCl$_3$) δ 6.72 (d, 1H, J=2.0 Hz), 4.05 (br s, 1H), 2.42-2.18 (m, 2H), 0.83 (s, 3H), 0.81 (s, 3H); $^{13}$C NMR (CDCl$_3$) δ 160.26, 117.48, 113.28, 66.34, 55.59, 54.51, 47.48, 39.13, 36.28, 35.75, 34.53, 34.43, 33.83, 31.90, 31.71, 28.91, 28.18, 20.31, 15.87, 11.10. Anal. (C$_{20}$H$_{29}$NO): C, 80.21%; H, 9.76%; N, 4.68%. Found: C, 80.39%; H, 9.75%; N, 4.69%.

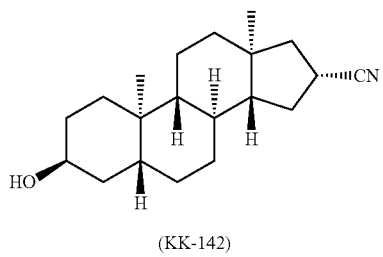

(KK-142)

(3β,5β,8α,9β,10α,13α,14β,16α)-3-Hydroxyandrost-16-carbonitrile (99, KK-142)

Compound 99 (41 mg, 92%) was prepared as a white solid from compound 98 using the procedure described for the preparation of compound 94. Compound 99 had: mp: 206-208° C.; $[\alpha]_D^{23}$ +21 (c 0.05, CHCl$_3$); IR $\nu_{max}$ 3478, 2929, 2850, 2234, 1450, 1383, 1265 cm$^{-1}$; $^1$H NMR (CDCl$_3$) δ 4.05 (br s, 1H), 2.83 (apparent q, J=8.0 Hz), 2.20 (m, 1H), 0.92 (s, 3H), 0.79 (s, 3H); $^{13}$C NMR (CDCl$_3$) δ 124.86, 66.37, 54.61, 54.12, 45.16, 41.57, 38.96, 38.24, 36.12, 35.73, 35.29, 32.18, 32.13, 28.94, 28.28, 23.16, 20.37, 18.18, 11.14. Anal. (C$_{20}$H$_{31}$NO): C, 79.68%; H, 10.36%; N, 4.65%. Found: C, 79.42%; H, 10.15%; N, 4.42%.

Scheme 11

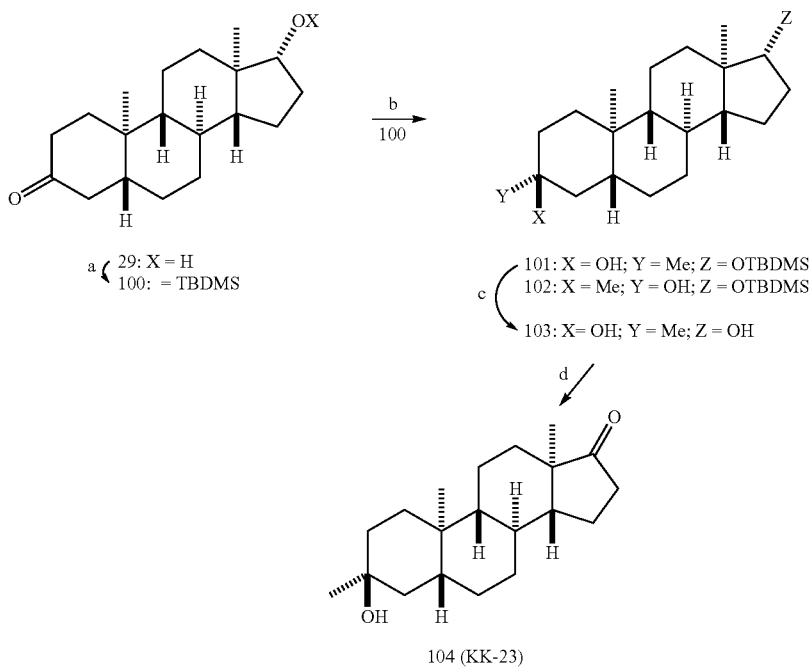

In accordance with Scheme 11, the following compounds were prepared, using methods generally known in the art and as outlined below.

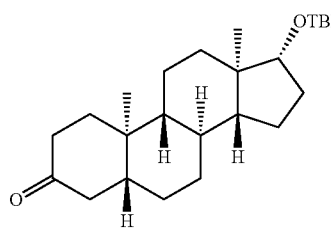

(5β,8α,9β,10α,13α,14β,17α)-17-[[(1,1-Dimethylethyl)dimethylsilyl]oxy]-androstan-3-one (100)

Compound 29 (400 mg, 1.38 mmol), TBDMSCl (603 mg, 4 mmol), imidazole (340 mg, 5 mmol) and 4-DMAP (10 mg) was stirred in DMF (5 mL) at room temperature for 16 h. Aqueous saturated NaHCO$_3$ was added and the product extracted into ethyl acetate (3×50 mL). The combined extracts were dried and solvent removed give a crude white solid which was purified by flash column chromatography (silica gel, eluted with 10% EtOAc in hexanes to yield product 100 as a white solid (500 mg, 90%): mp 131-133° C.; IR ν$_{max}$ 2934, 2856, 1716, 1461, 1471, 1446, 1251 cm$^{-1}$; $^1$H NMR (CDCl$_3$) δ 3.55 (t, 1H, J=8.0 Hz), 1.01 (s, 3H), 0.88 (s, 9H), 0.72 (s, 3H), 0.01 (s, 3H), 0.00 (s, 3H); $^{13}$C NMR (CDCl$_3$) δ 212.1, 81.7, 54.1, 50.5, 46.8, 44.7, 43.3, 38.6, 37.1, 35.7, 35.5, 31.3, 30.9, 28.8, 25.8, 23.5, 21.1, 18.1, 11.5, 11.4, −4.5, −4.8. Anal. (C$_{25}$H$_{44}$O$_2$Si): C, 74.19%; H, 10.96%. Found: C, 74.04%; H, 11.12%.

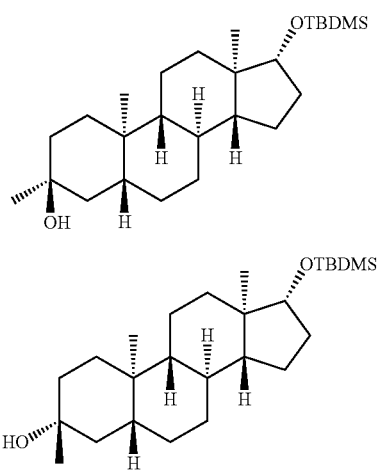

(3β,5β,8α,9β,10α,13α,14β,17α)-17-[[(1,1-Dimethylethyl)dimethylsilyl]oxy]-3-methylandrostan-3-ol (101) and (3α,5β,8α,9β,10α,13α,14β,17α)-17-[[(1,1-Dimethylethyl)dimethylsilyl]oxy]-3-methylandrostan-3-ol (102)

To a cold solution (0° C.) of compound 100 (405 mg, 1 mmol) in 5 THF (5 mL) was added MeMgCl (3M in diethyl ether, 2 mL) and the mixture was stirred 0° C. for 2 h. Aqueous NH$_4$Cl was added and the product was extracted into EtOAc (3×50 mL). The combined extracts were dried and solvent removed to give products 101 and 102 as a mixture which was purified and separated by flash column chromatography (silica gel, eluted with 15% EtOAc in hexanes) to yield less polar, first eluted product 102 (210 mg, 50%) and more polar, second eluted product 101 (190 mg, 45%) as white solids.

Compound 101 had: m.p. 154-156° C.; IR ν$_{max}$ 3267, 2928, 2856, 1471, 1462, 1449, 1249 cm$^{-1}$; $^1$H NMR (CDCl$_3$) δ 3.53 (t, 1H, J=7.7 Hz), 1.24 (s, 3H), 0.87 (s, 9H), 0.81 (s, 3H), 0.69 (s, 3H), 0.00 (s, 6H); $^{13}$C NMR δ 81.8, 71.5, 54.8, 50.7, 44.4, 43.35, 43.35, 37.2, 36.6, 36.4, 36.1, 35.6, 31.7, 30.9, 28.6, 26.6, 25.8, 23.5, 20.9, 18.1, 11.9, 11.4, −4.5, −4.8. Anal. (C$_{26}$H$_{48}$O$_2$Si): C, 74.22%; H, 11.50%. Found: C, 73.98%; H, 11.68%.

Compound 102 had: m.p 54-56° C.; IR ν$_{max}$ 3383, 2954, 2856, 1472, 1462, 1446, 1250 cm$^{-1}$; $^1$H NMR (CDCl$_3$) δ 3.54 (t, 1H, J=8.5 Hz), 1.19 (s, 3H), 0.87 (s, 9H), 0.75 (s, 3H), 0.69 (s, 3H), 0.01 (s, 3H), 0.00 (s, 3H).; $^{13}$C NMR (CDCl$_3$) δ 81.8, 69.7, 54.5, 50.7, 43.3, 41.8, 41.2, 37.2, 35.6, 34.9, 34.0, 31.6, 31.6, 30.9, 28.4, 25.8, 23.5, 20.6, 18.1, 11.4, 11.2, −4.5, −4.8. Anal. (C$_{26}$H$_{48}$O$_2$Si): C, 74.22%; H, 10.50%. Found: C, 74.24%; H, 11.50%.

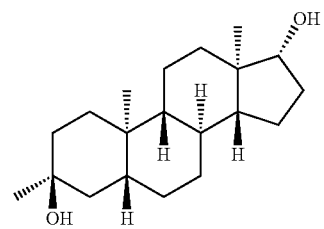

(3β,5β,8α,9β,10α,13α,14β,17a)-3-Methylandrostane-3,17-diol (103)

Compound 101 (170 mg, 0.40 mmol) and 3 N HCl (2 mL) in THF (5 mL) was stirred at room temperature for 6 h. Aqueous NaHCO3 was added and the product extracted into EtOAc. Solvent removal gave an oil, which was purified by flash column chromatography (silica gel, eluted with 30% EtOAc in hexanes) to give product 103 as a white solid (100 mg, 81%): mp 191-193° C.; IR ν$_{max}$ 3232, 2922, 2856, 1445, 1445, 1378, 1337 cm$^{-1}$; $^1$H NMR (CDCl$_3$) δ 3.62 (t, 1H, J=8.5 Hz), 1.24 (s, 3H), 0.82 (s, 3H), 0.73 (s, 3H); $^{13}$C NMR (CDCl$_3$) δ 81.9, 71.4, 54.6, 51.0, 44.3, 43.3, 43.0, 36.7, 36.6, 36.4, 36.1, 35.5, 31.6, 30.5, 28.5, 26.6, 23.3, 20.8, 11.9, 11.1. Anal. (C$_{20}$H$_{34}$O$_2$): C, 78.38%; H, 11.18%. Found: C, 78.18%; H, 10.99%.

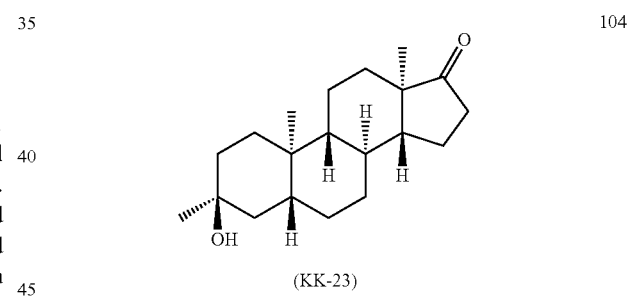

(KK-23)

(3β,5β,8α,9β,10α,13α,14β)-3-Hydroxy-3-methylandrostan-17-one (104, KK-23)

Compound 102 (90 mg, 0.29 mmol), PCC (215.6 mg, 1 mmol) and sodium acetate (82 mg) in CH$_2$Cl$_2$ was stirred at room temperature for 2 h. The reaction was passed through a silica gel column and purified by elution with 20% EtOAc in hexanes to give product 104 as a white solid (80 mg, 90%) which was re-crystallized from acetone-water: mp 183-185° C.; [α]$_D^{23}$ −100.0 (c 0.43, CHCl$_3$); IR ν$_{max}$ 3468, 2967, 2922, 2856, 1732, 1451, 1377 cm$^{-1}$; $^1$H NMR (CDCl$_3$) δ 1.18 (s, 3H), 0.79 (s, 3H), 0.77 (s, 3H); $^{13}$C NMR δ (CDCl$_3$) 221.4, 71.3, 54.5, 51.4, 47.8, 44.2, 43.1, 36.5, 36.3, 36.1, 35.8, 35.0, 31.5, 30.8, 28.3, 26.6, 21.7, 20.4, 13.8, 11.8. Anal. (C$_{20}$H$_{32}$O$_2$): C, 78.90%; H, 10.59%. Found: C, 78.92%; H, 10.42%.

Scheme 12

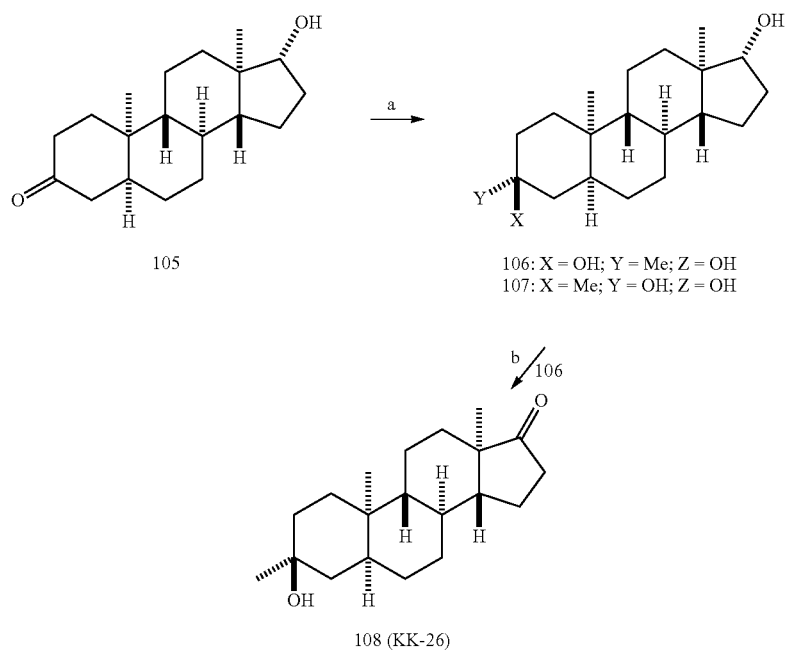

In accordance with Scheme 12, the following compounds were prepared, using methods generally known in the art and as outlined below.

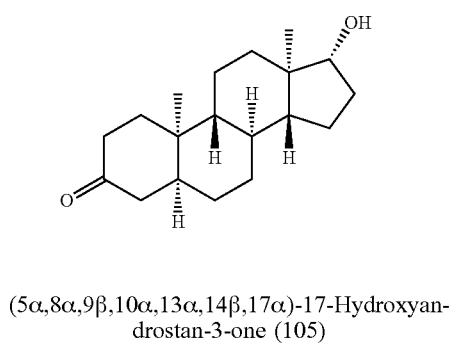

(5α,8α,9β,10α,13α,14β,17α)-17-Hydroxyandrostan-3-one (105)

This compound was prepared as previously described. (Hu, Y. F.; Wittmer, L. L.; Kalkbrenner, M.; Evers, A. S.; Zorumski, C. F.; Covey, D. F. Neurosteroid analogues. Part 5. Enantiomers of neuroactive steroids and benz[e]indenes: total synthesis, electrophysiological effects on $GABA_A$ receptor function and anesthetic actions in tadpoles. *J. Chem. Soc. Perkin Trans.* 1 1997, 3665-3671.)

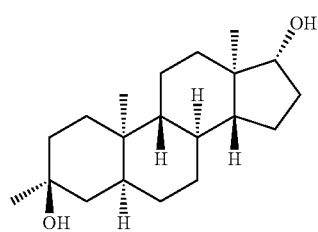

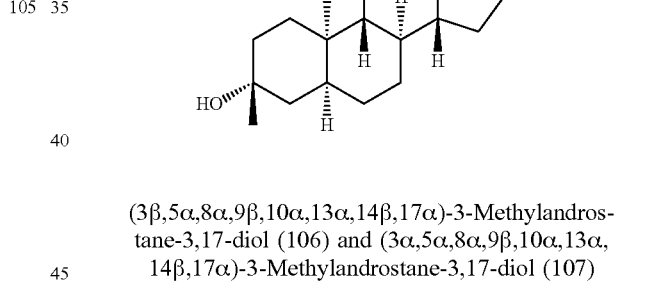

(3β,5α,8α,9β,10α,13α,14β,17α)-3-Methylandrostane-3,17-diol (106) and (3α,5α,8α,9β,10α,13α,14β,17α)-3-Methylandrostane-3,17-diol (107)

To a cold solution (0° C.) of compound 105 (300 mg, 1.03 mmol) in THF (5 mL) was added MeLi (1.6 M in diethylether, 4 mL, 6.4 mmol) and the reaction was stirred at 0° C. for 6 h. Saturated aqueous $NH_4Cl$ was added and the products extracted into EtOAc (3×50 mL). The combined extracts were dried and the solvent removed to give a solid. Products 106 and 107 were purified and separated by flash column chromatography (silica gel, eluted with 20-30% EtOAc in hexanes) to yield to yield less polar, first eluted product 107 (125 mg, 39%) and more polar, second eluted product 106 (65 mg, 20%) as white solids. Unreacted compound 105 (85 mg, 28%) was also recovered.

Compound 106 had: mp 212-214° C.; IR $v_{max}$ 3306, 2894, 2861, 1442, 1406, 1378, 1367, 1356 $cm^{-1}$; $^1H$ NMR ($CDCl_3$) δ 3.57 (s, 1H, J=8.5 Hz), 1.19 (s, 3H), 0.89 (s, 3H), 0.65 (s, 3H); $^{13}C$ NMR ($CDCl_3$) δ 81.9, 72.1, 51.1, 43.1, 41.3, 41.2, 40.0, 36.9, 35.8, 35.3, 35.1, 34.8, 30.6, 26.9, 26.4, 25.9, 23.5, 23.4, 20.4, 11.1.

Compound 107 had: mp 105-107° C.; IR $v_{max}$ 3337, 2922, 2858, 1446, 1374, 1265 $cm^{-1}$; $^1H$ NMR ($CDCl_3$) δ 3.61 (t, J=8.0 Hz), 1.22 (s, 3H), 0.98 (s, 3H), 0.72 (s, 3H); $^{13}C$ NMR (CDCl$_3$) δ 81.9, 70.2, 51.0, 43.1, 39.9, 39.5, 38.4, 36.9, 35.7, 34.6, 33.7, 32.0, 31.6, 30.5, 26.5, 25.9, 23.6, 23.3, 20.6, 11.1.

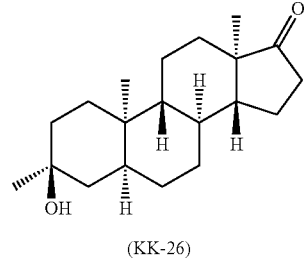

(KK-26)

(3β,5α,8α,9β,10α,13α,14β)-3-Hydroxy-3-methylandrostan-17-one (108, KK-26)

Compound 106 (55 mg, 0.18 mmol), PCC (150 mg, 0.7 mmol) and sodium acetate (58 mg, 0.7 mmol)) in CH$_2$Cl$_2$ were stirred at room temperature for 2 h. The reaction was passed through a silica gel column and purified by elution with 20% EtOAc in hexanes to give product 108 as a white solid (49 mg, 89%). mp low melting, <50° C.; [α]$_D^{23}$ −77.8 (c 0.65, CHCl$_3$); IR $v_{max}$ 3440 2934, 2861, 1732, 1470, 1454, 1373, 1273 cm$^{-1}$; $^1$H NMR (CDCl$_3$) δ 3.60-3.30 (b s, 1H), 2.37 (dd, 1H, J=19.2, 8.8 Hz), 1.19 (s, 3H), 0.90 (s, 3H) and 0.78 (s, 3H); $^{13}$C NMR (CDCl$_3$) δ 221.2, 72.0, 51.5, 47.8, 41.3, 41.1, 40.1, 35.9, 35.3, 35.2, 35.2, 34.7, 31.7, 26.7, 26.3, 25.2, 23.4 21.7, 20.1, 13.7. Anal. (C$_{20}$H$_{32}$O$_2$): C, 78.90%; H, 10.59%. Found: C, 79.00%; H, 10.68%.

[$^{35}$S]-TBPS Displacement

The IC$_{50}$ values for the compounds of the examples as non-competitive displacers of [$^{35}$S]-TBPS from the picrotoxin binding site on GABA$_A$ receptors are reported in Table 1.

TABLE 1

Inhibition of [$^{35}$S]-TBPS Binding

| Compound | IC$_{50}$ | n$_{Hill}$ |
|---|---|---|
| KK-18 | 627 ± 100 | 1.31 ± 0.22 |
| KK-23 | 185 ± 28 | 0.94 ± 0.12 |
| KK-26 | 290 ± 33 | 1.15 ± 0.13 |
| KK-97 | 112 ± 7 | 0.94 ± 0.05 |
| KK-102 | 146 ± 18 | 0.98 ± 0.11 |
| KK-103 | 238 ± 21 | 0.86 ± 0.06 |
| KK-114 | 1,520 ± 240 | 1.06 ± 0.14 |
| KK-117 | 198 ± 25 | 0.98 ± 0.11 |
| KK-122 | 83 ± 11 | 1.15 ± 0.15 |
| KK-134 | 92 ± 9 | 0.89 ± 0.07 |
| KK-135 | 184 ± 11 | 1.05 ± 0.06 |
| KK-136 | 335 ± 27 | 1.01 ± 0.07 |
| KK-137 | 22 ± 4 | 0.86 ± 0.09 |
| KK-138 | 32 ± 3 | 1.00 ± 0.08 |
| KK-141 | 154 ± 19 | 1.10 ± 0.13 |
| KK-142 | 29 ± 3 | 0.81 ± 0.05 |
| MQ-35 | 81 ± 8 | 0.92 ± 0.07 |
| MQ-117 | 19 ± 8 | 0.54 ± 0.08 |
| MQ-124 | 8950 ± 1860 | 1.02 ± 0.10 |
| MQ-125 | 121 ± 10 | 0.95 ± 0.07 |

Results presented are from duplicate experiments performed in triplicate. Error limits are calculated as standard error of the mean. Methods used are known in the art (see, e.g., Jiang, et al., Neurosteroid analogues. 9. Conformationally constrained pregnanes: structure-activity studies of 13,24-cyclo-18,21-dinorcholane analogues of the GABA modulatory and anesthetic steroids (3α,5α)- and (3α,5β)-3-hydroxypregnan-20-one. J. Med. Chem. 2003, 46, 5334-5348).

Electrophysiology Results

The compounds of the present disclosure were evaluated for the ability to potentiate chloride currents mediated by 2 μM GABA at rat α$_1$β$_2$γ$_{2L}$ type GABA$_A$ receptors expressed in Xenopus laevis oocytes and the results are shown in Table 2.

TABLE 2

Modulation of Rat α$_1$β$_2$γ$_{2L}$ GABA$_A$ Receptor Function

| | Oocyte electrophysiology | | | |
|---|---|---|---|---|
| Compound | 0.1 μM | 1.0 μM | 10 μM | (gating) 10 μM |
| KK-18 | 1.07 ± 0.05 | 1.64 ± 0.11 | 9.34 ± 1.36 | 0.13 ± 0.12 |
| KK-23 | 1.11 ± 0.15 | 3.31 ± 0.43 | 19.74 ± 5.64 | 0.09 ± 0.02 |
| KK-26 | 1.38 ± 0.10 | 5.10 ± 0.64 | 23.74 ± 2.88 | 0.49 ± 0.18 |
| KK-97 | 1.75 ± 0.24 | 6.15 ± 0.41 | 30.62 ± 2.14 | 0.16 ± 0.04 |
| KK-102 | 1.20 ± 0.02 | 4.23 ± 0.24 | 13.91 ± 1.38 | 0.04 ± 0.0 |
| KK-103 | 0.97 ± 0.02 | 2.43 ± 0.02 | 10.52 ± 0.61 | 0.02 ± 0.01 |
| KK-114 | 0.93 ± 0.02 | 1.13 ± 0.02 | 3.56 ± 0.15 | 0.01 ± 0.02 |
| KK-117 | 1.21 ± 0.02 | 3.67 ± 0.33 | 12.21 ± 1.26 | 0.05 ± 0.03 |
| KK-122 | 1.41 ± 0.07 | 6.48 ± 0.40 | 16.00 ± 2.21 | 0.08 ± 0.03 |
| KK-134 | 1.16 ± 0.07 | 5.22 ± 1.09 | 8.27 ± 1.27 | 0.04 ± 0.05 |
| KK-135 | 1.17 ± 0.09 | 3.26 ± 0.31 | 6.21 ± 0.31 | −0.04 ± 0.06 |
| KK-136 | 0.98 ± 0.02 | 1.98 ± 0.14 | 10.04 ± 1.26 | 0.29 ± 0.25 |
| KK-137 | 2.32 ± 0.17 | 7.08 ± 0.54 | 10.17 ± 0.68 | −0.04 ± 0.08 |
| KK-138 | 1.63 ± 0.23 | 5.87 ± 1.65 | 10.16 ± 3.18 | 0.14 ± 0.06 |
| KK-141 | 1.08 ± 0.11 | 1.35 ± 0.08 | 1.58 ± 0.13 | 0.08 ± 0.06 |
| KK-142 | 2.20 ± 0.20 | 8.83 ± 3.12 | 13.32 ± 4.54 | 0.03 ± 0.01 |
| MQ-35 | 1.42 ± 0.02 | 7.72 ± 0.39 | 34.70 ± 1.69 | 0.15 ± 0.04 |
| MQ-117 | 3.43 ± 0.29 | 11.10 ± 1.16 | 26.20 ± 2.91 | 0.06 ± 0.02 |
| MQ-124 | 0.68 ± 0.03 | 0.85 ± 0.03 | 1.57 ± 0.05 | −0.01 ± 0 |
| MQ-125 | 1.19 ± 0.18 | 5.02 ± 0.40 | 14.08 ± 2.23 | 0.43 ± 0.41 |

The GABA concentration used for the control response was 2 μM. Each compound was evaluated on at least four different oocytes at the concentrations indicated, and the results reported are the ratio of currents measured in the presence/absence of added compound. Gating represents direct current gated by 10 μM compound in the absence of GABA, and this current is reported as the ratio of compound only current/2 M GABA current. Error limits are calculated as standard error of the mean (N≥4). Receptor expression and whole-cell and single-channel recordings were carried out as described previously (see Jiang, et al., Neurosteroid analogues. 9. Conformationally constrained pregnanes: structure-activity studies of 13,24-cyclo-18,21-dinorcholane analogues of the GABA modulatory and anesthetic steroids (3α,5α)- and (3α,5β)-3-hydroxypregnan-20-one. J. Med. Chem. 2003, 46, 5334-5348).

Tadpole Loss of Righting and Swimming

Table 3 discloses the anesthetic effects of the compounds of the present disclosure. In particular, the anesthetic effect of the compounds of the present disclosure on Loss of Righting Reflex (LRR) and Loss of Swimming Reflex (LSR).

TABLE 3

Tadpole Loss of Righting (LRR) & Loss of Swimming (LSR) EC$_{50}$ Values (μM) Reflexes by Analogues

| Compound | Tadpole LRR EC$_{50}$ (μM) | Tadpole LRR n$_{Hill}$ | Tadpole LSR EC$_{50}$ (μM) | Tadpole LSR n$_{Hill}$ |
|---|---|---|---|---|
| KK-18 | 3.20 ± 2.03 | −1.98 ± 2.03 | >10 | — |
| KK-23 | 0.93 ± 0.53 | −1.39 ± 0.86 | 2.81 ± 0.01 | −21 ± 0.5 |
| KK-26 | 1.88 ± 0.0 | −4.68 ± 0.01 | 5.48 ± 0.20 | −33 ± 0.2 |
| KK-97 | 0.49 ± 0.11 | −1.35 ± 0.31 | 1.73 ± 0.03 | −36 ± 0.1 |
| KK-102 | 1.21 ± 0.42 | −4.29 ± 6.63 | 5.48 ± 0.12 | −33 ± 0.1 |
| KK-103 | 1.16 ± 0.21 | −4.04 ± 4.06 | 5.48 ± 0.12 | −33 ± 0.1 |
| KK-114 | 3.64 ± 2.17 | −4.32 ± 11.8 | >10 | — |
| KK-117 | 0.59 ± 0.07 | −1.84 ± 0.32 | 2.94 ± 0.0 | −20 ± 0.6 |
| KK-122 | 0.34 ± 0.4 | −2.75 ± 1.13 | 1.73 ± 0.03 | −36 ± 0.1 |
| KK-134 | 10/10[a] | — | 10/10[a] | — |
| KK-135 | 10/10[a] | — | 10/10[a] | — |
| KK-136 | 0.48 ± 0.02 | −2.32 ± 0.12 | 1.73 ± 0.03 | −36 ± 0.1 |
| KK-137 | 0.13 ± 0.0 | −2.13 ± 0.07 | 0.55 ± 0.01 | −33 ± 0.1 |
| KK-138 | 0.14 ± 0.0 | −1.94 ± 0.08 | 0.87 ± 0.0 | −20 ± 0.0 |
| KK-141 | 5/10[b] | — | 0/10[c] | — |
| KK-142 | 10/10[a] | — | 10/10[a] | — |
| MQ-35 | 0.55 ± 0.09 | −2.90 ± 0.1 | 1.73 ± 0.04 | −36 ± 0.1 |
| MQ-117 | 0.079 ± 0.003 | −1.94 ± 0.12 | 0.33 ± 0.0 | −19 ± 0.5 |
| MQ-124 | >10[d] | — | >10[e] | — |
| MQ-125 | 10/10[a] | — | 10/10[a] | — |

[a] All tadpoles lost LRR and LSR at a concentration of 3 μM.
[b] 5/10 tadpoles lost LRR at a concentration of 3 μM.
[c] 0/10 tadpoles lost LSR at a concentration of 3 μM.
[d] 0/10 tadpoles lost LRR at a concentration of 10 μM.
[e] 0/10 tadpoles lost LSR at a concentration of 10 μM.

Methods used are known in the art (see, e.g., Jiang, et al., Neurosteroid analogues. 9. Conformationally constrained pregnanes: structure-activity studies of 13,24-cyclo-18,21-dinorcholane analogues of the GABA modulatory and anesthetic steroids (3α,5α)- and (3α,5β)-3-hydroxypregnan-20-one. *J. Med. Chem.* 2003, 46, 5334-5348). Error limits are calculated as standard error of the mean (N=10 or more animals at each of five or more different concentrations).

Mouse Behavioral Data

FIG. 1 is a graphical depiction of the duration of anesthesia (LRR) induced by tail vein injection of alphaxalone, compound 9 (MQ-35; ent-7) and compound 28 (KK-122, ent-9). The compounds were dissolved in 22.5% aqueous 2-(hydroxypropyl)-β-cyclodextrin. For compound 28, serial dilutions of a 8 mg/kg stock solution with 0.9% saline were made to obtain the lower doses tested.

The duration of anesthesia, defined as the loss of righting reflex is shown in FIG. 1. The potency, rate of onset, and rate of recovery for compounds MQ-35 and KK-122 relative to these parameters for anesthetic steroid alphaxalone were made using tail vein injections in mice. As can be seen from the results in FIG. 1, a 16 mg/kg dose of alphaxalone caused LRR of about 4 minutes. At a dose of 8 mg/kg, compound MQ-35 caused LRR of about 3 minutes and at a dose of 16 mg/kg duration of LRR was increased to about 7 minutes.

For compound KK-122, no LRR was observed at a dose of 1 mg/kg and LRR of about 1 minute was observed at a threshold dose of 2 mg/kg. At 4 mg/kg, LRR induced by KK-122 lasted about 5 minutes and at a dose of 8 mg/kg LRR lasted for about 9 minutes. For all three compounds, the onset of anesthesia was immediate (i.e., less than 30 seconds) and recovery was characterized by a rapid progression over 1-2 minutes from an initial return of leg movement followed by righting and subsequent walking around the cage.

General Methods

The compounds discussed in the present disclosure were produced as discussed elsewhere throughout this disclosure and by the following methods. Solvents were either used as purchased or dried and purified by standard methodology. Extraction solvents were dried with anhydrous Na$_2$SO$_4$ and after filtration, removed on a rotary evaporator. Flash chromatography was performed using silica gel (32-63 μm) purchased from Scientific Adsorbents (Atlanta, Ga.). Melting points were determined on a Kofler micro hot stage and are uncorrected. FT-IR spectra were recorded as films on a NaCl plate. NMR spectra were recorded in CDCl$_3$ at ambient temperature at 300 MHz ($^1$H) or 74 MHz ($^{13}$C). Purity was determined by TLC on 250 μm thick UNIPLATES™ from Analtech (Newark, Del.). All pure compounds (purity >95%) gave a single spot on TLC. Elemental analyses were performed by M-H-W Laboratories (Phoenix, Ariz.).

EQUIVALENTS AND SCOPE

In view of the above, it will be seen that the several advantages of the disclosure are achieved and other advantageous results attained. As various changes could be made in the above processes and composites without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. It is also noted that the terms "comprising", "including", "having" or "containing" are intended to be open and permits the inclusion of additional elements or steps.

What is claimed is:
1. A compound of Formula (I):

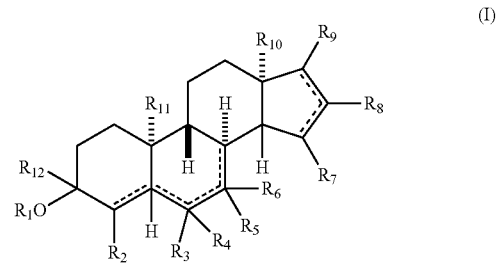

or a pharmaceutically acceptable salt thereof; wherein:
R$_1$ is H;
R$_2$ is H, optionally substituted C$_1$-C$_4$ alkoxy, aryloxy, morpholinyl, optionally substituted C$_2$-C$_4$ alkenoxy, optionally substituted C$_2$-C$_4$ alkynoxy, or —O—C(O)—R$_x$, where R$_x$ is optionally substituted C$_1$-C$_{20}$ alkyl;
R$_3$ is H, OH, optionally substituted C$_1$-C$_4$ alkoxy, optionally substituted C$_2$-C$_4$ alkenoxy, optionally substituted C$_2$-C$_4$ alkynoxy, aryloxy, acetyl, substituted acetyl, cyano, nitro, spiroepoxide or —O—C(O)—R$_u$, where R$_u$ is optionally substituted C$_1$-C$_{20}$ alkyl;
R$_4$ is H, C$_1$-C$_4$ alkyl, C$_2$-C$_4$ alkenyl, C$_2$-C$_4$ alkynyl or —O—C(O)—R$_t$, where R$_t$ is optionally substituted C$_1$-C$_{20}$ alkyl;
with the proviso that when R$_3$ and R$_4$ are taken together, R$_3$ and R$_4$ combine to form =O or =CR$_y$, (where R$_y$ is CN, CH$_2$NH$_2$, C(O)—O—R$_w$, (where R$_w$ is H, optionally substituted C$_1$-C$_{10}$ or optionally substituted phenyl), or CH$_2$OR$_v$ (where R$_v$ is H, optionally substituted C$_1$-C$_{10}$, optionally substituted phenyl, or optionally substituted napthyl));

R$_5$ is H;

R$_6$ is H, C$_1$-C$_4$ alkyl, C$_2$-C$_4$ alkenyl, C$_2$-C$_4$ alkynyl or —O—C(O)—R$_r$, where R$_r$ is optionally substituted C$_1$-C$_{20}$ alkyl;

R$_7$ is H, optionally substituted C$_1$-C$_4$ alkoxy, optionally substituted C$_2$-C$_4$ alkenoxy, optionally substituted C$_2$-C$_4$ alkynoxy, spirooxirane, cyano, =O, nitro or optionally substituted COCH$_3$;

R$_8$ is H, optionally substituted C$_1$-C$_4$ alkoxy, optionally substituted C$_2$-C$_4$ alkenoxy, optionally substituted C$_2$-C$_4$ alkynoxy, spirooxirane, cyano, =O, =CHCN, nitro or optionally substituted COCH$_3$;

R$_9$ is H, optionally substituted C$_1$-C$_4$ alkoxy, spiroepoxide or =O;

R$_{10}$ is H or optionally substituted C$_1$-C$_4$ alkyl, optionally substituted C$_2$-C$_4$ alkenyl, or optionally substituted C$_2$-C$_4$ alkynyl;

R$_{11}$ is H or optionally substituted C$_1$-C$_4$ alkyl, optionally substituted C$_2$-C$_4$ alkenyl, or optionally substituted C$_2$-C$_4$ alkynyl;

R$_{12}$ is H or optionally substituted C$_1$-C$_4$ alkyl, optionally substituted C$_2$-C$_4$ alkenyl, or optionally substituted C$_2$-C$_4$ alkynyl;

- - - denotes an optional, additional C—C bond, resulting in a C=C bond between C$_4$-C$_5$, C$_5$-C$_6$, C$_6$-C$_7$, C$_7$-C$_8$, C$_{15}$-C$_{16}$, and/or C$_{16}$-C$_{17}$; and, with the provisos that:

at least one of R$_7$, R$_8$ and R$_9$ is not hydrogen;

when R$_1$-R$_8$ and R$_{12}$ are H, R$_{10}$ and R$_{11}$ are CH$_3$, R$_9$ is other than =O or spiroepoxide;

when R$_1$-R$_8$ and R$_{11}$-R$_{12}$ are H, R$_{10}$ is CH$_3$, and the C$_5$—H is in the alpha position, R$_9$ is other than =O.

2. The compound of claim 1, wherein R$_2$, when not H and no double bond is present between C$_4$-C$_5$, is in the alpha configuration.

3. The compound of claim 1, wherein R$_8$, when not =O, is in the alpha configuration.

4. The compound of claim 1, wherein R$_9$, when not =O, is in the alpha configuration.

5. The compound of claim 1, wherein R$_2$ is selected from the group consisting of H and methoxy.

6. The compound of claim 1, wherein R$_3$ is H.

7. The compound of claim 1, wherein R$_4$ is H.

8. The compound of claim 1, wherein R$_6$ is H.

9. The compound of claim 1, wherein R$_7$ is selected from the group consisting of H and —OCH$_3$.

10. The compound of claim 1, wherein R$_8$ is selected from the group consisting of =O, —OCH$_3$, COCH$_3$, CN and =CHCN.

11. The compound of claim 1, wherein R$_9$ is =O.

12. The compound of claim 1, wherein R$_{10}$ is selected from the group consisting of H and methyl.

13. The compound of claim 1, wherein R$_{11}$ is selected from the group consisting of H and methyl.

14. The compound of claim 1, wherein R$_{12}$ is selected from the group consisting of H and methyl.

15. The compound of claim 1 selected from the group consisting of:

-continued

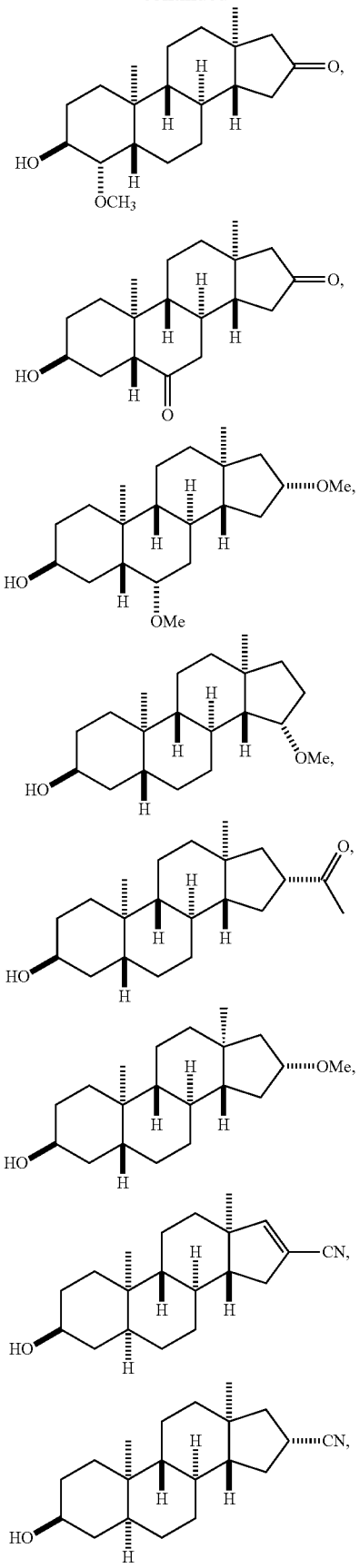

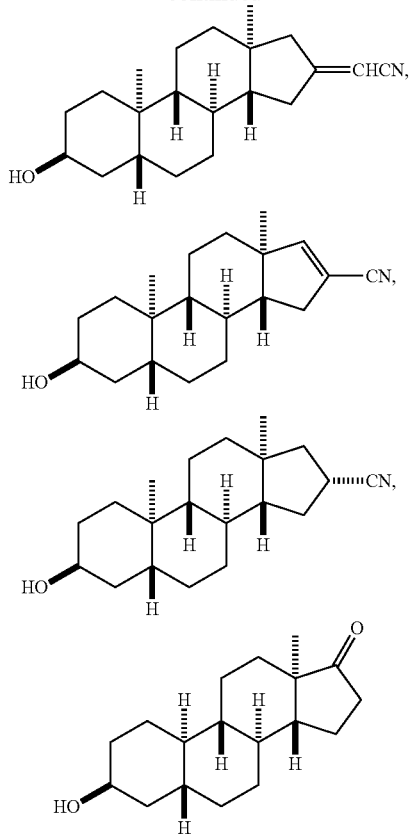

and pharmaceutically acceptable salts thereof.

16. A method of inducing anesthesia in a subject in need thereof, said method comprising administering to the subject a therapeutically effective amount of a compound of Formula (I):

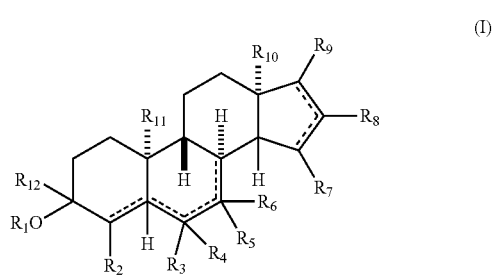

(I)

or a pharmaceutically acceptable salt thereof; wherein:
$R_1$ is H;
$R_2$ is H, optionally substituted $C_1$-$C_4$ alkoxy, aryloxy, morpholinyl, optionally substituted $C_2$-$C_4$ alkenoxy, optionally substituted $C_2$-$C_4$ alkynoxy, or —O—C(O)—$R_x$, where $R_x$ is optionally substituted $C_1$-$C_{20}$ alkyl;
$R_3$ is H, OH, optionally substituted $C_1$-$C_4$ alkoxy, optionally substituted $C_2$-$C_4$ alkenoxy, optionally substituted $C_2$-$C_4$ alkynoxy, aryloxy, acetyl, substituted acetyl, cyano, nitro, spiroepoxide or —O—C(O)—$R_u$, where $R_u$ is optionally substituted $C_1$-$C_{20}$ alkyl;
$R_4$ is H, $C_1$-$C_4$ alkyl, $C_2$-$C_4$ alkenyl, $C_2$-$C_4$ alkynyl or —O—C(O)—$R_t$, where $R_t$ is optionally substituted $C_1$-$C_{20}$ alkyl;

with the proviso that when $R_3$ and $R_4$ are taken together, $R_3$ and $R_4$ combine to form $=O$ or $=CR_y$, (where $R_y$ is CN, $CH_2NH_2$, C(O)—O—$R_w$ (where $R_w$ is H, optionally substituted $C_1$-$C_{10}$ or optionally substituted phenyl), or $CH_2OR_v$ (where $R_v$ is H, optionally substituted $C_1$-$C_{10}$, optionally substituted phenyl, or optionally substituted napthyl));

$R_5$ is H;

$R_6$ is H, $C_1$-$C_4$ alkyl, $C_2$-$C_4$ alkenyl, $C_2$-$C_4$ alkynyl or —O—C(O)—$R_r$, where $R_r$ is optionally substituted $C_1$-$C_{20}$ alkyl;

$R_7$ is H, optionally substituted $C_1$-$C_4$ alkoxy, optionally substituted $C_2$-$C_4$ alkenoxy, optionally substituted $C_2$-$C_4$ alkynoxy, spirooxirane, cyano, $=O$, nitro or optionally substituted $COCH_3$;

$R_8$ is H, optionally substituted $C_1$-$C_4$ alkoxy, optionally substituted $C_2$-$C_4$ alkenoxy, optionally substituted $C_2$-$C_4$ alkynoxy, spirooxirane, cyano, $=O$, $=CHCN$, nitro or optionally substituted $COCH_3$;

$R_9$ is H, optionally substituted $C_1$-$C_4$ alkoxy, spiroepoxide or $=O$;

$R_{10}$ is H or optionally substituted $C_1$-$C_4$ alkyl, optionally substituted $C_2$-$C_4$ alkenyl, or optionally substituted $C_2$-$C_4$ alkynyl;

$R_{11}$ is H or optionally substituted $C_1$-$C_4$ alkyl, optionally substituted $C_2$-$C_4$ alkenyl, or optionally substituted $C_2$-$C_4$ alkynyl;

$R_{12}$ is H or optionally substituted $C_1$-$C_4$ alkyl, optionally substituted $C_2$-$C_4$ alkenyl, or optionally substituted $C_2$-$C_4$ alkynyl;

- - - denotes an optional, additional C—C bond, resulting in a $C=C$ bond between $C_4$-$C_5$, $C_5$-$C_6$, $C_6$-$C_7$, $C_{15}$-$C_{16}$, and/or $C_{16}$-$C_{17}$; and, with the provisos that:

at least one of $R_7$, $R_8$ and $R_9$ is not hydrogen;

when $R_1$-$R_8$ and $R_{12}$ are H, $R_{10}$ and $R_{11}$ are $CH_3$, $R_9$ is other than $=O$ or spiroepoxide;

when $R_1$-$R_8$ and $R_{11}$-$R_{12}$ are H, $R_{10}$ is $CH_3$, and the $C_5$—H is in the alpha position, $R_9$ is other than $=O$.

* * * * *

UNITED STATES PATENT AND TRADEMARK OFFICE
CERTIFICATE OF CORRECTION

| | | |
|---|---|---|
| PATENT NO. | : 10,202,413 B2 | Page 1 of 1 |
| APPLICATION NO. | : 14/767235 | |
| DATED | : February 12, 2019 | |
| INVENTOR(S) | : Douglas Covey | |

It is certified that error appears in the above-identified patent and that said Letters Patent is hereby corrected as shown below:

In the Specification

Column 1, Lines 19-22, delete "The claimed subject matter was developed with Government support under NIH Grant #GM47969, awarded by the National Institute of Health. Accordingly, the Government has certain rights in the claimed subject matter." and insert therefor -- This invention was made with government support under GM047967 awarded by the National Institutes of Health. The government has certain rights in the invention. --.

Signed and Sealed this
Seventh Day of April, 2020

Andrei Iancu
*Director of the United States Patent and Trademark Office*